(12) United States Patent
Ravanello et al.

(10) Patent No.: US 7,179,956 B2
(45) Date of Patent: Feb. 20, 2007

(54) ELEVATION OF OIL LEVELS IN PLANTS

(75) Inventors: Monica P. Ravanello, Vacaville, CA (US); Terry J. Foley, Williamsburg, IA (US); John R. LeDeaux, St. Louis, MO (US); Annette E. Wyrick, Vacaville, CA (US); Thomas J. Savage, Sacramento, CA (US)

(73) Assignee: Monsanto Technology LLC, St. Louis, MO (US)

( * ) Notice: Subject to any disclaimer, the term of this patent is extended or adjusted under 35 U.S.C. 154(b) by 199 days.

(21) Appl. No.: 10/877,645

(22) Filed: Jun. 25, 2004

(65) Prior Publication Data

US 2005/0005327 A1 Jan. 6, 2005

Related U.S. Application Data

(60) Provisional application No. 60/483,491, filed on Jun. 27, 2003.

(51) Int. Cl.
| C12N 15/82 | (2006.01) |
| C12N 15/63 | (2006.01) |
| C12N 15/52 | (2006.01) |
| C12N 5/04  | (2006.01) |
| A01H 5/00  | (2006.01) |
| A01H 5/10  | (2006.01) |

(52) U.S. Cl. .................. 800/281; 800/278; 800/320.1; 800/300.1; 800/287; 435/320.1; 435/419; 536/23.2; 536/23.6

(58) Field of Classification Search ..................... None
See application file for complete search history.

(56) References Cited

U.S. PATENT DOCUMENTS

| 6,268,550 B1 * | 7/2001 | Gengenbach et al. ....... 800/298 |
| 2003/0154524 A1 | 8/2003 | Foley |
| 2003/0172416 A1 | 9/2003 | Foley |

FOREIGN PATENT DOCUMENTS

| WO | WO9710328    | * 3/1997 |
| WO | WO 02/062129 |   8/2002 |

OTHER PUBLICATIONS

Echt et al., "Evidence for the Inclusion of Controlling Elements Within the Structural Gene at the Waxy Locus in Maize", Genetics, 99:275-284, 1981.
Ernst et al., "Identification of a Major QTL Affecting Oil Concentration in Maize", Trait Development, Dow AgroSciences, LLC, 156:121.
Guan et al., "Starch Biosynthesis: Understanding the Functions and Interactions of Multiple Isozymes of Starch Synthase and Branching Enzyme", Trends in Glycoscience and Glycotechnology, 10(54):307-319, 1998.
Han et al., "Location of Starch Granule-Associated Proteins Revealed by Confocal Laser Scanning Microscopy", Journal of Cereal Science, 35:109-116, 2002.
Okagaki et al., "Comparison of Non-Mutant and Mutant Waxy Genes in Rice and Maize", Genetics, 120:1137-1143, 1988.
Pfahler et al., "Biochemical Composition of Maize (Zea mays L.) Pollen", Theoretical and Applied Genetics, 41:2-4, 1971.
Renessen Argentine Brochure, "Renessen es realidad en Argentine" concerning "Maiz Alto Valor", a corn hybrid produced from a cross of variety HO1001 and a second corn variety. The crossing was done outside of the U.S. Corn see of the aforementioned corn hybrid produced as a pollinator was sold in Argentina more than one year before the priority date of the application. HO1001 itself was not sold or offered for sale.
Shure et al., "Molecular Identification and Isolation of the Waxy Locus in Maize", Cell, 35:225-233, 1983.
Voelker et al., "Fatty Acid Biosynthesis Redirected to Medium Chains in Transgenic Oilseed Plants", Science, 257:72-74, 1992.

* cited by examiner

*Primary Examiner*—David T. Fox
*Assistant Examiner*—Brent T Page
(74) *Attorney, Agent, or Firm*—Fulbright & Jaworski L.L.P.

(57) ABSTRACT

This present invention provides a method for increasing oil levels in corn kernel tissue by expression of an HO1001 GBSS allele. The present invention also provides isolated nucleic acid molecules encoding a HO1001 GBSS polypeptide.

16 Claims, 40 Drawing Sheets

|  | | | | | | |
|---|---|---|---|---|---|---|
| | ....1150........1160........1170........1180........1190........1200 |
| pMON72506 gDNA | ---ATCCTGT CCTTGAGTTT CGTCCAGATC CTGGCGTGTA TCTGCATGCG TGTTTGATGA |
| pMON72510 gDNA | ---ATCCTGT CCTTGAGTTT CGTCCAGATA CTGGCGTGTA TCTGC----G TGTTTGATGA |
| published cds 22509 | ---------- ---------- ---------- ---------- ---------- ---------- |
| published X03935 | CCGATCCTGT CCTTGAGTTT CGTCCAGATC CTGGCGCGTA TCTGC----G TGTTTGATGA |
| Consensus | ---ATCCTGT CCTTGAGTTT CGTCCAGATm CTGGCGYGTA TCTGC----G TGTTTGATGA |

| | ....1210........1220........1230........1240........1250........1260 |
| pMON72506 gDNA | TCCAGGTTCA TCGAAATCTAA ATCTGTCCGT GCACATGTCT TCTCTCTCTC TGTCT----- |
| pMON72510 gDNA | TCCAGGTTCT TCGAACCTAA ATCTGTCCGT GCACATGTCC TCTCTCTCTC TGTCTCTCTC |
| published cds 22509 | ---------- ---------- ---------- ---------- ---------- ---------- |
| published X03935 | TCCAGGTTCT TCGAACCTAA ATCTGTCCGT GCACACGTCT TTCTCTCTCT TC-------- |
| Consensus | TCCAGGTTCw TCGAAYCTAA ATCTGTCCGT GCACAyGTCy TyTCTCTCTC Tsnnn----- |

| | ....1270........1280........1290........1300........1310........1320 |
| pMON72506 gDNA | -GCTATGCAG TGGATTAATC GGCATGGCGG CTCTGGCCAC GTCGCAGCTC GTCGCAACGC |
| pMON72510 gDNA | TGCTATGCAG TGGATTAATC GGCATGGCGG CTCTGGCCAC GTCGCAGCTC GTCGCAACGC |
| published cds 22509 | ---------- ---------- --ATGGGCGG CTCTGGCCAC GTCGCAGCTC GTCGCAACGC |
| published X03935 | --CTACGCAG TGGATTAATC GGCATGGCGG CTCTGGCCAC GTCGCAGCTC GTCGCAACGC |
| Consensus | -nCTAYGCAG TGGATTAATC GGCATGGCGG CTCTGGCCAC GTCGCAGCTC GTCGCAACGC |

|  | ...3310 | ...3320 | ...3330 | ...3340 | ...3350 | ...3360 |
|---|---|---|---|---|---|---|
| pMON72506 gDNA | ..CCGGTTCAGG | CCGTGGAGGC | CAAGGCGCTG | AACAAGGAGG | CGCTGCAGGC | GGAGGTCGGG |
| pMON72510 gDNA | CCGGTTCAGG | CCGTGGAGGC | CAAGGCGCTG | AACAAGGAGG | CGCTGCAGGC | GGAGGTCGGG |
| published cds 22509 | ---------- | ---------- | ---------- | ---------- | ---------- | ---------- |
| published X03935 | CCGGTTCAGG | CCGTGGAGGC | CAAGGCGCTG | AACAAGGAGG | CGCTGCAGGC | GGAGGTCGGG |
| Consensus | CCGGTTCAGG | CCGTGGAGGC | CAAGGCGCTG | AACAAGGAGG | CGCTGCAGGC | GGAGGTCGGG |

|  | ...3370 | ...3380 | ...3390 | ...3400 | ...3410 | ...3420 |
|---|---|---|---|---|---|---|
| pMON72506 gDNA | CTCCCGGTGG | ACCGGAACAT | CCCGCTGGTG | GCGTTCATCG | GCAGGCTGGA | AGAGCAGAAG |
| pMON72510 gDNA | CTCCCGGTGG | ACCGGAACAT | CCCGCTGGTG | GCGTTCATCG | GCAGGCTGGA | AGAGCAGAAG |
| published cds 22509 | CTCCCGGTGG | ACCGGAACAT | CCCGCTGGTG | GCGTTCATCG | GCAGGCTGGA | AGAGCAGAAG |
| published X03935 | CTCCCGGTGG | ACCGGAACAT | CCCGCTGGTG | GCGTTCATCG | GCAGGCTGGA | AGAGCAGAAG |
| Consensus | CTCCCGGTGG | ACCGGAACAT | CCCGCTGGTG | GCGTTCATCG | GCAGGCTGGA | AGAGCAGAAG |

|  | ...3430 | ...3440 | ...3450 | ...3460 | ...3470 | ...3480 |
|---|---|---|---|---|---|---|
| pMON72506 gDNA | GGCCCCGACG | TCATGGCGGC | CAGCTCATGG | AGATGGTGGA | GGACGTGCAG |  |
| pMON72510 gDNA | GGCCCCGACG | TCATGGCGGC | CAGCTCATGG | AGATGGTGGA | GGACGTGCAG |  |
| published cds 22509 | GGCCCCGACG | TCATGGCGGC | CAGCTCATGG | AGATGGTGGA | GGACGTGCAG |  |
| published X03935 | GGCCCCGACG | TCATGGCGGC | CAGCTCATGG | AGATGGTGGA | GGACGTGCAG |  |
| Consensus | GGCCCCGACG | TCATGGCGGC | CAGCTCATGG | AGATGGTGGA | GGACGTGCAG |  |

```
                       ....4570........  ....4580........  ....4590........  ....4600........  ....4610........  ....4620
pMON72506 gDNA         ....GATGCTTGCT    TGTGCTAGTG        TAATGTAGTG        TAGTGGTGGC        CAGTGGCACA        ACCTAATAAG
pMON72510 gDNA         
published cds 22509    
published X03935       GCTGCTTGCT        TGTGCTAGTG        TAATGTAGTG        TAGTGGTGGC        CAGTGGCACA        ACCTAATAAG Consensus              nnnnnnnnnn        nnnnnnnnnn        nnnnnnnnnn        nnnnnnnnnn        nnnnnnnnnn        nnnnnnnnnn ....4630........  ....4640........  ....4650........  ....4660........  ....4670........  ....4680
pMON72506 gDNA         CGCATGAACT        AATTGCTTGC        GTGTGTAGTT        AAGTACCGAT        CGGTAATTTT        ATATTGCGAG
pMON72510 gDNA         
published cds 22509    
published X03935       CGCATGAACT        AATTGCTTGC        GTGTGTAGTT        AAGTACCGAT        CGGTAATTTT        ATATTGCGAG Consensus              nnnnnnnnnn        nnnnnnnnnn        nnnnnnnnnn        nnnnnnnnnn        nnnnnnnnnn        nnnnnnnnnn ....4690........  ....4700........  ....4710........  ....4720........  ....4730........  ....4740
pMON72506 gDNA         TAAATAAATG        GACCTGTAGT        GGTGGAGTAA        ATAATCCC
pMON72510 gDNA         
published cds 22509    
published X03935       TAAATAAATG        GACCTGTAGT        GGTGGAGTAA        ATAATCCCTG        CTGTTCGGTG        TTCTTATCGC Consensus              nnnnnnnnnn        nnnnnnnnnn        nnnnnnnnnn        nnnnnnnn--        ----------        ----------
```

Figure 1
(25 of 26)

| | | | | |
|---|---|---|---|---|
| | 1 | 10 | 20 | 30 | 40 |
| pMON72506 prt | MAALATSQLV | ATRAGLGVPD | ASTFRRGAAQ | GLRGARASAA |
| published CAA27574 | MAALATSQLV | ATRAGLGVPD | ASTFRRGAAQ | GLRGARASAA |
| Consensus | MAALATSQLV | ATRAGLGVPD | ASTFRRGAAQ | GLRGARASAA |

| | 50 | 60 | 70 | 80 |
|---|---|---|---|---|
| pMON72506 prt | ADTLSMRTSA | RAAPRLQLHQ | QQQQARRGAR | FPSLVVCASA |
| published CAA27574 | ADTLSMRTSA | RAAP - - - - | HQQQARRGGR | FPSLVVCASA |
| Consensus | ADTLSMRTSA | RAAPxxxxxx | xQQQARRGxR | FPSLVVCASA |

| | 90 | 100 | 110 | 120 |
|---|---|---|---|---|
| pMON72506 prt | GMNVVFVGAE | MAPWSKTGGL | GDVLGGLPPA | MAANGHRVMV |
| published CAA27574 | GMNVVFVGAE | MAPWSKTGGL | GDVLGGLPPA | MAANGHRVMV |
| Consensus | GMNVVFVGAE | MAPWSKTGGL | GDVLGGLPPA | MAANGHRVMV |

| | 130 | 140 | 150 | 160 |
|---|---|---|---|---|
| pMON72506 prt | VSPRYDQYKD | AWDTSVVSEI | KMGDRYETVR | FFHCYKRGVD |
| published CAA27574 | VSPRYDQYKD | AWDTSVVSEI | KMGDGYETVR | FFHCYKRGVD |
| Consensus | VSPRYDQYKD | AWDTSVVSEI | KMGDxYETVR | FFHCYKRGVD |

Figure 2
(1 of 4)

| | | | | | |
|---|---|---|---|---|---|
| pMON72506 prt | | | | | RVFVDHPLFL | ERVWGKTEEK | IYGPVAGTDY | RDNQLRFSLL |
| published CAA27574 | RVFVDHPLFL | ERVWGKTEEK | IYGPVAGTDY | RDNQLRFSLL |
| Consensus | RVFVDHPLFL | ERVWGKTEEK | IYGPVAGTDY | RDNQLRFSLL |

| | | | | |
|---|---|---|---|---|
| pMON72506 prt | CQAALEAPRI | LSLNNNPYFS | GPYGEDVVFV | CNDWHTGPLS |
| published CAA27574 | CQAALEAPRI | LSLNNNPYFS | GPYGEDVVFV | CNDWHTGPLS |
| Consensus | CQAALEAPRI | LSLNNNPYFS | GPYGEDVVFV | CNDWHTGPLS |

| | | | | |
|---|---|---|---|---|
| pMON72506 prt | CYLKSNYQSH | GIYRDAKTAF | CIHNISYQGR | FAFSDYPELN |
| published CAA27574 | CYLKSNYQSH | GIYRDAKTAF | CIHNISYQGR | FAFSDYPELN |
| Consensus | CYLKSNYQSH | GIYRDAKTAF | CIHNISYQGR | FAFSDYPELN |

| | | | |
|---|---|---|---|
| pMON72506 prt | LPERFKSSFD | FIDGYEKPVE | GRKINWMKAG | ILEADRVLTV |
| published CAA27574 | LPERFKSSFD | FIDGYEKPVE | GRKINWMKAG | ILEADRVLTV |
| Consensus | LPERFKSSFD | FIDGYEKPVE | GRKINWMKAG | ILEADRVLTV |

Figure 2
(2 of 4)

| | | | | | |
|---|---|---|---|---|---|
| pMON72506 prt | SPYYAEELIS | GIARGCELDN | IMRLTGITGI | VNGMDVSEWD | 360 |
| published CAA27574 | SPYYAEELIS | GIARGCELDN | IMRLTGITGI | VNGMDVSEWD | |
| Consensus | SPYYAEELIS | GIARGCELDN | IMRLTGITGI | VNGMDVSEWD | |
| pMON72506 prt | PSRDKYIAVK | YDVSTAVEAK | ALNKEALQAE | VGLPVDRNIP | 400 |
| published CAA27574 | PSRDKYIAVK | YDVSTAVEAK | ALNKEALQAE | VGLPVDRNIP | |
| Consensus | PSRDKYIAVK | YDVSTAVEAK | ALNKEALQAE | VGLPVDRNIP | |
| pMON72506 prt | LVAFIGRLEE | QKGPDVMAAA | IPQLMEMVED | VQIVLLGTGK | 440 |
| published CAA27574 | LVAFIGRLEE | QKGPDVMAAA | IPQLMEMVED | VQIVLLGTGK | |
| Consensus | LVAFIGRLEE | QKGPDVMAAA | IPQLMEMVED | VQIVLLGTGK | |
| pMON72506 prt | KKFERMLMSA | EEKFPGKVRA | VVKFNAALAH | HIMAGADVLA | 480 |
| published CAA27574 | KKFERMLMSA | EEKFPGKVRA | VVKFNAALAH | HIMAGADVLA | |
| Consensus | KKFERMLMSA | EEKFPGKVRA | VVKFNAALAH | HIMAGADVLA | |

Figure 2
(3 of 4)

```
pMON72506 prt         VTSRFEPCGL    IQLQGMRYGT    PCACASTGGL    VDTIIEGKTG
published CAA27574    VTSRFEPCGL    IQLQGMRYGT    PCACASTGGL    VDTIIEGKTG Consensus             VTSRFEPCGL    IQLQGMRYGT    PCACASTGGL    VDTIIEGKTG pMON72506 prt         FHMGRLSVDC    NVVEPADVKK    VATTLQRAIK    VVGTPVYEEM
published CAA27574    FHMGRLSVDC    NVVEPADVKK    VATTLQRAIK    VVGTPAYEEM Consensus             FHMGRLSVDC    NVVEPADVKK    VATTLQRAIK    VVGTPxYEEM pMON72506 prt         VRNCMIQDLS    WKGPAKNWEN    VLLSLGVAGG    AGPLISRVVQ
published CAA27574    VRNCMIQDLS    WKGPAKNWEN    VLLSLGVAGG    EPGVEGEEIA Consensus             VRNCMIQDLS    WKGPAKNWEN    VLLSLGVAGG    xxxxxxxxxx pMON72506 prt         RCWDIFLYML    FRLCDMDKYV
published CAA27574    PLAKENVAAP Consensus             xxxxxxxxxx    xxxxxxxxxx
```

Figure 2
(4 of 4)

|  | 1 | | | 10 | | | 20 | | | 30 | | | 40 |
|---|---|---|---|---|---|---|---|---|---|---|---|---|---|
| pMON72510 prt | M A A L A T S Q L V | A T R A G L G V P D | A S T F R R G A A Q | G L R G A R A S A A |
| published CAA27574 | M A A L A T S Q L V | A T R A G L G V P D | A S T F R R G A A Q | G L R G A R A S A A |
| Consensus | M A A L A T S Q L V | A T R A G L G V P D | A S T F R R G A A Q | G L R G A R A S A A |

|  | 50 | 60 | 70 | 80 |
|---|---|---|---|---|
| pMON72510 prt | A D T L S M R T S A | R A A P R H Q Q | A R R G x R F P S L | V V C A S A G M N V |
| published CAA27574 | A D T L S M R T S A | R A A P R H Q - Q | A R R G R F P S L | V V C A S A G M N V |
| Consensus | A D T L S M R T S A | R A A P R H Q x Q Q | A R R G x R F P S L | V V C A S A G M N V |

|  | 90 | 100 | 110 | 120 |
|---|---|---|---|---|
| pMON72510 prt | V F V G A E M A P W | S K T G G L G D V L | G G L P P A M A A N | G H R V M V V S P R |
| published CAA27574 | V F V G A E M A P W | S K T G G L G D V L | G G L P P A M A A N | G H R V M V V S P R |
| Consensus | V F V G A E M A P W | S K T G G L G D V L | G G L P P A M A A N | G H R V M V V S P R |

|  | 130 | 140 | 150 | 160 |
|---|---|---|---|---|
| pMON72510 prt | Y D Q Y K D A W D T | S V V S E I K M G D | G Y E T V R F F H C | Y K R G V D R V F V |
| published CAA27574 | Y D Q Y K D A W D T | S V V S E I K M G D | G Y E T V R F F H C | Y K R G V D R V F V |
| Consensus | Y D Q Y K D A W D T | S V V S E I K M G D | G Y E T V R F F H C | Y K R G V D R V F V |

Figure 3
(1 of 4)

| | | 170 | 180 | 190 | 200 |
|---|---|---|---|---|---|
| pMON72510 prt | | DHPLFLERVW | GKTEEKIYGP | VAGTDYRDNQ | LRFSLLCQAA |
| published CAA27574 | | DHPLFLERVW | GKTEEKIYGP | VAGTDYRDNQ | LRFSLLCQAA |

Consensus        DHPLFLERVW  GKTEEKIYGP  VAGTDYRDNQ  LRFSLLCQAA

| | | 210 | 220 | 230 | 240 |
|---|---|---|---|---|---|
| pMON72510 prt | | LEAPRILSLN | NNPYFSGPYG | EDVVFVCNDW | HTGPLSCYLK |
| published CAA27574 | | LEAPRILSLN | NNPYFSGPYG | EDVVFVCNDW | HTGPLSCYLK |

Consensus        LEAPRILSLN  NNPYFSGPYG  EDVVFVCNDW  HTGPLSCYLK

| | | 250 | 260 | 270 | 280 |
|---|---|---|---|---|---|
| pMON72510 prt | | SNYQSHGIYR | DAKTAFCIHN | ISYQGRFAFS | DYPELNLPER |
| published CAA27574 | | SNYQSHGIYR | DAKTAFCIHN | ISYQGRFAFS | DYPELNLPER |

Consensus        SNYQSHGIYR  DAKTAFCIHN  ISYQGRFAFS  DYPELNLPER

| | | 290 | 300 | 310 | 320 |
|---|---|---|---|---|---|
| pMON72510 prt | | FKSSFDFIDG | YEKPVEGRKI | NWMKAGILEA | DRVLTVSPYY |
| published CAA27574 | | FKSSFDFIDG | YEKPVEGRKI | NWMKAGILEA | DRVLTVSPYY |

Consensus        FKSSFDFIDG  YEKPVEGRKI  NWMKAGILEA  DRVLTVSPYY

Figure 3
(2 of 4)

| | | | | |
|---|---|---|---|---|
| | 330 | 340 | 350 | 360 |
| pMON72510 prt | AEELISGIAR | GCELDNIMRL | TGITGIVNGM | DVSEWDPSRD |
| published CAA27574 | AEELISGIAR | GCELDNIMRL | TGITGIVNGM | DVSEWDPSRD |
| Consensus | AEELISGIAR | GCELDNIMRL | TGITGIVNGM | DVSEWDPSRD |

| | | | | |
|---|---|---|---|---|
| | 370 | 380 | 390 | 400 |
| pMON72510 prt | KYIAVKYDVS | TAVEAKALNK | EALQAEVGLP | VDRNIPLVAF |
| published CAA27574 | KYIAVKYDVS | TAVEAKALNK | EALQAEVGLP | VDRNIPLVAF |
| Consensus | KYIAVKYDVS | TAVEAKALNK | EALQAEVGLP | VDRNIPLVAF |

| | | | | |
|---|---|---|---|---|
| | 410 | 420 | 430 | 440 |
| pMON72510 prt | IGRLEEQKGP | DVMAAAIPQL | MEMVEDVQIV | LLGTGKKKFE |
| published CAA27574 | IGRLEEQKGP | DVMAAAIPQL | MEMVEDVQIV | LLGTGKKKFE |
| Consensus | IGRLEEQKGP | DVMAAAIPQL | MEMVEDVQIV | LLGTGKKKFE |

| | | | | |
|---|---|---|---|---|
| | 450 | 460 | 470 | 480 |
| pMON72510 prt | RMLMSAEEKF | PGKVRAVVKF | NAALAHHIMA | GADVLAVTSR |
| published CAA27574 | RMLMSAEEKF | PGKVRAVVKF | NAALAHHIMA | GADVLAVTSR |
| Consensus | RMLMSAEEKF | PGKVRAVVKF | NAALAHHIMA | GADVLAVTSR |

Figure 3
(3 of 4)

```
pMON72510 prt         FEPCGLIQLQ  GMRYGTPCAC  ASTGGLVDTI  IEGKTGFHMG
published CAA27574    FEPCGLIQLQ  GMRYGTPCAC  ASTGGLVDTI  IEGKTGFHMG Consensus             FEPCGLIQLQ  GMRYGTPCAC  ASTGGLVDTI  IEGKTGFHMG pMON72510 prt         RLSVDCNVVE  PADVKKVATT  LQRAIKVVGT  PAYEEMVRNC
published CAA27574    RLSVDCNVVE  PADVKKVATT  LQRAIKVVGT  PAYEEMVRNC Consensus             RLSVDCNVVE  PADVKKVATT  LQRAIKVVGT  PAYEEMVRNC pMON72510 prt         MIQDLSWKGP  AKNWENVLLS  LGVAGGEPGV  EGEEIAPLAK
published CAA27574    MIQDLSWKGP  AKNWENVLLS  LGVAGGEPGV  EGEEIAPLAK Consensus             MIQDLSWKGP  AKNWENVLLS  LGVAGGEPGV  EGEEIAPLAK pMON72510 prt         ENVAAP
published CAA27574    ENVAAP Consensus             ENVAAP
```

Figure 3
(4 of 4)

SEQUENCE LISTING

<160> NUMBER OF SEQ ID NOS: 17

<210> SEQ ID NO 1
<211> LENGTH: 4470
<212> TYPE: DNA
<213> ORGANISM: Zea mays

<400> SEQUENCE: 1

| | | | | | |
|---|---|---|---|---|---:|
| aattcgccct | ttcagccgtt | cgtgtggcag | attcatctgt | tgtctcgtct | cctgtgcttc | 60 |
| ctgggtagct | tgtgcagtgg | agctgacatg | gtctgagcag | gcttaaaatt | tgctcgtaga | 120 |
| cgaggagtac | cagcacagca | cgttgcggat | ttctctgcct | gtgaagtgca | acgtctagga | 180 |
| ttgtcacacg | ccttggtcgc | gtcgatgcgg | tggtgagcag | agcagcaaca | gctgggcgac | 240 |
| ccaaagttgg | attccgtgtc | ttcgtcgtac | gtacgcgcgc | gccggggaca | cgcagagagc | 300 |
| ggagagcgag | ccgtgcacgg | ggaggtggtg | tggaagtgaa | gccgcgcgcc | cggccgcccg | 360 |
| cgcccggtgg | gcaacccaaa | agtacccacg | acaagcgaag | gcgccaaagc | gatccaagct | 420 |
| ccggaacgca | tcagccacaa | gcagccgaga | accgaaccgg | tgggcgacgc | gtcgtgggac | 480 |
| ggacgcgggc | gacgcttcca | aacggggcca | cgtacgccgg | cgtgtgcgtg | tgtgcgtgca | 540 |
| gacgacaagc | caaggcgagg | cagccccccga | tcgggaaaag | cgtcaagtag | gtgcgccggg | 600 |
| ctttggcttt | gggcgcgagc | gctggcgtgc | gggtcagtcg | ctggtgcgca | gtgccggggc | 660 |
| gaacgggtat | cgtgggggc | gcgggcggag | gagagcgtgg | cgagggccga | gagcagcgcg | 720 |
| cggccgggtc | acgcaacgcg | ccccacgtac | agcctccccc | tccgcgcgcg | ctagaaatac | 780 |
| cgaggcctgg | accgggggcc | cccggcaca | tccatccatc | gaccgatcga | tcgatcgcca | 840 |
| cagccaacat | caccccgccga | ggcgacgcga | cagccgccag | gaggaaggaa | taaactcact | 900 |
| gccagccagt | gaaggggggag | aagtgtactg | ctccgtcgac | cagtgcgcgc | accgcccggc | 960 |
| agggctgctc | atctcgtcga | cgaccaggtt | ccgttccgtt | ccgatccgat | cctgtccttg | 1020 |
| agtttcgtcc | agatcctggc | gtgtatctgc | atgcgtgttt | gatgatccag | gttcatcgaa | 1080 |
| tctaaatctg | tccgtgcaca | tgtcttctct | ctctctgtct | gctatgcagt | ggattaatcg | 1140 |
| gcatggcggc | tctggccacg | tcgcagctcg | tcgcaacgcg | cgccggcctg | ggcgtcccgg | 1200 |
| acgcgtccac | gttccgccgc | ggcgccgcgc | agggcctgag | ggggggcccgg | gcgtcggcgg | 1260 |
| cggcggacac | gctcagcatg | cggaccagcg | cgcgcgcggc | gcccaggctc | cagctgcacc | 1320 |
| agcagcagca | gcaggcgcgc | gcgggggcca | ggttcccgtc | gctcgtcgtg | tgcgccagcg | 1380 |
| ccggcatgaa | cgtcgtcttc | gtcggcgccc | aggtggcgcc | gtggagcaag | accggcggcc | 1440 |
| tcggcgacgt | cctcggcggc | ctgccgccgg | ccatggccgt | aagcgcgcgc | accgagacat | 1500 |
| gcatccgttg | gatcgcgtct | tcttcgtgct | cttgccgcgt | gcatgatgca | tgtgtttcct | 1560 |
| cctggctcgt | gtatgtgact | gacgtgtgtg | ttcgggcatg | caatgcatgc | aggcgaatgg | 1620 |
| gcaccgtgtc | atggtcgtct | ctccccgcta | cgaccagtac | aaggacgcct | gggacaccag | 1680 |
| cgtcgtgtcc | gaagtacggc | caccgagatc | agattcagat | cacacatcac | agtcacacac | 1740 |
| accgtcatat | gaacctttct | ctgctctgat | gcctgcagat | caagatggga | gacaggtacg | 1800 |
| agacggtcag | gttcttccac | tgctacaagc | gcggagtgga | ccgcgtgttc | gttgaccacc | 1860 |
| cactgttcct | ggagagggtg | agatgagatc | tgatcactcg | atacgcaatt | accaccccat | 1920 |
| tgtaagcagt | tacagtgagc | cttttttttt | gcccccgcct | ggtcgctggt | ttcaggtttg | 1980 |
| gggaaagacc | gaggagaaga | tctacgggcc | tgtcgctgga | acggactaca | gggacaacca | 2040 |

```
gctgcggttc agcctgctat gccaggtcag gatggcttgc tactacaact tcagatcatc    2100
tgtatgcagc agtatacacc gatgagaaat gcatgctgtt ctgcaggcag cacttgaagc    2160
tccaaggatc ctgagcctca acaacaaccc atacttctcc ggaccatacg gtaagagttg    2220
tagtcttcgt atatatatct gttgagctcg agaatcttca caggaaacgg cccatcagac    2280
ggactgtctt tttatactga ctactgctgc tgctcttcgt ccatccatcc atacaagggg    2340
aggacgtcgt gttcgtctgc aacgactggc acaccggccc tctctcgtgc tacctcaaga    2400
gcaactacca gtcccacggc atctacaggg acgcaaaggt tgccttctcg gaactgaaca    2460
acgccgtttt cgttctccat gctcgtatat acctcatctg gtggtggtgc ttctctgaaa    2520
ctgaaactga aactgactgc atgtctgtct gaccatcttc acgtactacc taccagaccg    2580
ctttctgcat ccacaacatc tcctaccagg gccggttcgc cttctccgac tacccggagc    2640
tgaacctccc cgagagattc aagtcgtcct tcgatttcat cgacgggtct gttttcctgc    2700
gtgcatgtga acattcatga acggtaaccc acaactgctc gcgtcctgct ggttcattat    2760 ctggcccttga ttgcattgta gctacgagaa gcccgtggaa ggccggaaga tcaactggat    2820
gaaggccggg atcctcgagg ccgacagggt cctcaccgtc agcccctact acgccgagga    2880
gctcatctcc ggcatcgcca ggggctgcga gtcgacaac atcatgcgcc tcaccggcat    2940
caccggcatc gtcaacggca tggacgtcag cgagtgggac cccagcaggg acaagtacat    3000
cgccgtgaag tacgacgtgt cgacggtgag ctggctagct agctgattct gctgcctggt    3060
cctcctgctc atgctggttc ggttctgacg cggcaagtgt acgtacgtgc gtgcgacggt    3120
ggtgtggtgt ccggttcagg ccgtggaggc caaggcgctg aacaaggagg cgctgcaggc    3180
ggaggtcggg ctcccggtgg accggaacat cccgctggtg gcgttcatcg gcaggctgga    3240
agagcagaag ggccccgacg tcatggcggc cgccatcccg cagctcatgg agatggtgga    3300
ggacgtgcag atcgttctgc tggtacgtgt gcgccggccg ccacccggct actacatgcg    3360
tgtatcgttc gttctactgg aacatgcgtg tgagcaacgc gatggataat gctgcagggc    3420
acgggcaaga agaagttcga gcgcatgctc atgagcgccg aggagaagtt cccaggcaag    3480
gtgcgcgccg tggtcaagtt caacgcggcg ctggcgcacc acatcatggc cggcgccgac    3540
gtgctcgccg tcaccagccg cttcgagccc tgcggcctca tccagctgca ggggatgcga    3600
tacggaacgg tacgagagaa aaaaaaacat cctgaatcta tcctgacgag agggacagag    3660
acagattgat tatgaatgct tcatcgattt gaattgattg atctatgtct cccgctgcga    3720
ctcttgcagc cctgcgcctg cgcgtccacc ggtggactcg tcgacaccat catcgaaggc    3780
aagaccgggt tccacatggg ccgcctcagc gtcgacgtaa gcctacctct gccatgatct    3840
ttcttccttc tgtatgtatg tatgtatgta tgaatcagca ccgccattct tgtttcgtcg    3900
tcctctcttc ccagtgcaac gtcgtggagc cggcggacgt caagaaggtg gccaccacct    3960
tgcagcgcgc catcaaggtg gtcggcacgc cggtgtacga ggagatggtg aggaactgca    4020
tgatccagga tctctcctgg aaggtacgtt cgcccgcccc gccagagcag agcgccaaga    4080
tcgatcgatc gaccgaccac acgtacgcgc ctcgctcttg tcgctgaccg tggtttaatt    4140
tgcgaaatgc gcagggccct gccaagaact gggagaacgt gctgctcagc ctcgggtcg    4200 ccggcggtgc agggccccctg atctcgcgcg tggtgcaaag atgttgggac atcttcttat    4260
atatgctgtt tcgtttatgt gatatggaca agtatgtgta gatgcttgct tgtgctagtg    4320
taatgtagtg tagtggtggc cagtggcaca acctaataag cgcatgaact aattgcttgc    4380
```

|  |  |
|---|---:|
| gtgtgtagtt aagtaccgat cggtaatttt atattgcgag taaataaatg gacctgtagt | 4440 |
| ggtggagtaa ataatcccgc tgaaagggcg | 4470 |

<210> SEQ ID NO 2
<211> LENGTH: 1818
<212> TYPE: DNA
<213> ORGANISM: Zea mays

<400> SEQUENCE: 2

|  |  |
|---|---:|
| atggcggctc tggccacgtc gcagctcgtc gcaacgcgcg ccggcctggg cgtcccggac | 60 |
| gcgtccacgt tccgccgcgg cgccgcgcag ggcctgaggg gggcccgggc gtcggcggcg | 120 |
| gcggacacgc tcagcatgcg gaccagcgcg cgcgcggcgc ccaggcacca gcagcaggcg | 180 |
| cgccgcgggg gcaggttccc gtcgctcgtc gtgtgcgcca gcgccggcat gaacgtcgtc | 240 |
| ttcgtcggcg ccgagatggc gccgtggagc aagaccggcg gcctcggcga cgtcctcggc | 300 |
| ggcctgccgc cggccatggc cgcgaacggg caccgtgtca tggtcgtctc tccccgctac | 360 |
| gaccagtaca aggacgcctg ggacaccagc gtcgtgtccg agatcaagat gggagacggg | 420 |
| tacgagacgt tcaggttctt ccactgctac aagcgcggag tggaccgcgt gttcgttgac | 480 |
| cacccactgt tcctggagag ggtttgggga agaccgagg agaagatcta cgggcctgtc | 540 |
| gctggaacgc actacaggga caaccagctg cggttcagcc tgctatgcca ggcagcactt | 600 |
| gaagctccaa ggatcctgag cctcaacaac aacccatact ctccggacc atacggggag | 660 |
| gacgtcgtgt tcgtctgcaa cgactggcac accggccctc tctcgtgcta cctcaagagc | 720 |
| aactaccagt cccacggcat ctacagggac gcaaagaccg ctttctgcat ccacaacatc | 780 |
| tcctaccagg gccggttcgc cttctccgac tacccggagc tgaacctccc ggagagattc | 840 |
| aagtcgtcct tcgatttcat cgacggctac gagaagcccg tggaaggccg aagatcaac | 900 |
| tggatgaagg ccgggatcct cgaggccgac agggtcctca ccgtcagccc ctactacgcc | 960 |
| gaggagctca tctccggcat cgccaggggc tgcgagctcg acaacatcat cgcgcctcacc | 1020 |
| ggcatcaccg gcatcgtcaa cggcatggac gtcagcgagt gggaccccag cagggacaag | 1080 |
| tacatcgccg tgaagtacga cgtgtcgacg gccgtggagg ccaaggcgct gaacaaggag | 1140 |
| gcgctgcagg cggaggtcgg gctcccggtg gaccggaaca tcccgctggt ggcgttcatc | 1200 |
| ggcaggctgg aagagcagaa gggcccccgac gtcatggcgg ccgccatccc gcagctcatg | 1260 |
| gagatggtgg aggacgtgca gatcgttctg ctgggcacgg gcaagaagaa gttcgagcgc | 1320 |
| atgctcatga gcgccgagga gaagttccca ggcaaggtgc gcgccgtggt caagttcaac | 1380 |
| gcggcgctgg cgcaccacat catggccggc gccgacgtgc tcgccgtcac cagccgcttc | 1440 |
| gagccctgcg gcctcatcca gctgcagggg atgcgatacg aacgccctg cgcctgcgcg | 1500 |
| tccaccggtg gactcgtcga caccatcatc gaaggcaaga ccgggttcca catgggccgc | 1560 |
| ctcagcgtcg actgtaacgt cgtggagccg gcggacgtca agaaggtggc caccacattg | 1620 |
| cagcgcgcca tcaaggtggt cggcacgccg gcgtacgagg agatggtgag gaactgcatg | 1680 |
| atccaggatc tctcctggaa gggccctgcc aagaactggg agaacgtgct gctcagcctc | 1740 |
| ggggtcgccg gcggcgagcc aggggtcgaa ggcgaggaga tcgcgccgct cgccaaggag | 1800 |
| aacgtggccg cgccctga | 1818 |

<210> SEQ ID NO 3
<211> LENGTH: 620
<212> TYPE: PRT
<213> ORGANISM: Zea mays

```
<400> SEQUENCE: 3

Met Ala Ala Leu Ala Thr Ser Gln Leu Val Ala Thr Arg Ala Gly Leu
1               5                   10                  15

Gly Val Pro Asp Ala Ser Thr Phe Arg Arg Gly Ala Ala Gln Gly Leu
            20                  25                  30

Arg Gly Ala Arg Ala Ser Ala Ala Asp Thr Leu Ser Met Arg Thr
        35                  40                  45

Ser Ala Arg Ala Ala Pro Arg Leu Gln Leu His Gln Gln Gln Gln Gln
    50                  55                  60

Ala Arg Arg Gly Ala Arg Phe Pro Ser Leu Val Val Cys Ala Ser Ala
65                  70                  75                  80

Gly Met Asn Val Val Phe Val Gly Ala Glu Met Ala Pro Trp Ser Lys
                85                  90                  95

Thr Gly Gly Leu Gly Asp Val Leu Gly Gly Leu Pro Pro Ala Met Ala
            100                 105                 110

Ala Asn Gly His Arg Val Met Val Val Ser Pro Arg Tyr Asp Gln Tyr
            115                 120                 125

Lys Asp Ala Trp Asp Thr Ser Val Val Ser Glu Ile Lys Met Gly Asp
        130                 135                 140

Arg Tyr Glu Thr Val Arg Phe Phe His Cys Tyr Lys Arg Gly Val Asp
145                 150                 155                 160

Arg Val Phe Val Asp His Pro Leu Phe Leu Glu Arg Val Trp Gly Lys
                165                 170                 175

Thr Glu Glu Lys Ile Tyr Gly Pro Val Ala Gly Thr Asp Tyr Arg Asp
            180                 185                 190

Asn Gln Leu Arg Phe Ser Leu Leu Cys Gln Ala Ala Leu Glu Ala Pro
        195                 200                 205

Arg Ile Leu Ser Leu Asn Asn Asn Pro Tyr Phe Ser Gly Pro Tyr Gly
210                 215                 220

Glu Asp Val Val Phe Val Cys Asn Asp Trp His Thr Gly Pro Leu Ser
225                 230                 235                 240

Cys Tyr Leu Lys Ser Asn Tyr Gln Ser His Gly Ile Tyr Arg Asp Ala
                245                 250                 255

Lys Thr Ala Phe Cys Ile His Asn Ile Ser Tyr Gln Gly Arg Phe Ala
            260                 265                 270

Phe Ser Asp Tyr Pro Glu Leu Asn Leu Pro Glu Arg Phe Lys Ser Ser
        275                 280                 285

Phe Asp Phe Ile Asp Gly Tyr Glu Lys Pro Val Glu Gly Arg Lys Ile
    290                 295                 300

Asn Trp Met Lys Ala Gly Ile Leu Glu Ala Asp Arg Val Leu Thr Val
305                 310                 315                 320

Ser Pro Tyr Tyr Ala Glu Glu Leu Ile Ser Gly Ile Ala Arg Gly Cys
                325                 330                 335

Glu Leu Asp Asn Ile Met Arg Leu Thr Gly Ile Thr Gly Ile Val Asn
            340                 345                 350

Gly Met Asp Val Ser Glu Trp Asp Pro Ser Arg Asp Lys Tyr Ile Ala
        355                 360                 365

Val Lys Tyr Asp Val Ser Thr Ala Val Glu Ala Lys Ala Leu Asn Lys
    370                 375                 380

Glu Ala Leu Gln Ala Glu Val Gly Leu Pro Val Asp Arg Asn Ile Pro
385                 390                 395                 400

Leu Val Ala Phe Ile Gly Arg Leu Glu Glu Gln Lys Gly Pro Asp Val
```

```
                    405                 410                 415
Met Ala Ala Ile Pro Gln Leu Met Glu Met Val Glu Asp Val Gln
            420                 425                 430

Ile Val Leu Leu Gly Thr Gly Lys Lys Phe Glu Arg Met Leu Met
            435                 440                 445

Ser Ala Glu Glu Lys Phe Pro Gly Lys Val Arg Ala Val Lys Phe
    450                 455                 460

Asn Ala Ala Leu Ala His His Ile Met Ala Gly Ala Asp Val Leu Ala
465                 470                 475                 480

Val Thr Ser Arg Phe Glu Pro Cys Gly Leu Ile Gln Leu Gln Gly Met
                485                 490                 495

Arg Tyr Gly Thr Pro Cys Ala Cys Ala Ser Thr Gly Leu Val Asp
            500                 505                 510

Thr Ile Ile Glu Gly Lys Thr Gly Phe His Met Gly Arg Leu Ser Val
            515                 520                 525

Asp Cys Asn Val Val Glu Pro Ala Asp Val Lys Lys Val Ala Thr Thr
    530                 535                 540

Leu Gln Arg Ala Ile Lys Val Val Gly Thr Pro Val Tyr Glu Glu Met
545                 550                 555                 560

Val Arg Asn Cys Met Ile Gln Asp Leu Ser Trp Lys Gly Pro Ala Lys
                565                 570                 575

Asn Trp Glu Asn Val Leu Leu Ser Leu Gly Val Ala Gly Ala Gly
            580                 585                 590

Pro Leu Ile Ser Arg Val Val Gln Arg Cys Trp Asp Ile Phe Leu Tyr
            595                 600                 605

Met Leu Phe Arg Leu Cys Asp Met Asp Lys Tyr Val
    610                 615                 620

<210> SEQ ID NO 4
<211> LENGTH: 605
<212> TYPE: PRT
<213> ORGANISM: Zea mays

<400> SEQUENCE: 4

Met Ala Ala Leu Ala Thr Ser Gln Leu Val Ala Thr Arg Ala Gly Leu
1               5                   10                  15

Gly Val Pro Asp Ala Ser Thr Phe Arg Arg Gly Ala Ala Gln Gly Leu
            20                  25                  30

Arg Gly Ala Arg Ala Ser Ala Ala Ala Asp Thr Leu Ser Met Arg Thr
        35                  40                  45

Ser Ala Arg Ala Ala Pro Arg His Gln Gln Gln Ala Arg Arg Gly Gly
    50                  55                  60

Arg Phe Pro Ser Leu Val Val Cys Ala Ser Ala Gly Met Asn Val Val
65                  70                  75                  80

Phe Val Gly Ala Glu Met Ala Pro Trp Ser Lys Thr Gly Gly Leu Gly
                85                  90                  95

Asp Val Leu Gly Gly Leu Pro Pro Ala Met Ala Ala Asn Gly His Arg
            100                 105                 110

Val Met Val Val Ser Pro Arg Tyr Asp Gln Tyr Lys Asp Ala Trp Asp
        115                 120                 125

Thr Ser Val Val Ser Glu Ile Lys Met Gly Asp Gly Tyr Glu Thr Val
    130                 135                 140

Arg Phe Phe His Cys Tyr Lys Arg Gly Val Asp Arg Val Phe Val Asp
145                 150                 155                 160
```

```
His Pro Leu Phe Leu Glu Arg Val Trp Gly Lys Thr Glu Lys Ile
            165                 170                 175
Tyr Gly Pro Val Ala Gly Thr Asp Tyr Arg Asp Asn Gln Leu Arg Phe
                180                 185                 190
Ser Leu Leu Cys Gln Ala Ala Leu Glu Ala Pro Arg Ile Leu Ser Leu
            195                 200                 205
Asn Asn Asn Pro Tyr Phe Ser Gly Pro Tyr Gly Glu Asp Val Val Phe
210                 215                 220
Val Cys Asn Asp Trp His Thr Gly Pro Leu Ser Cys Tyr Leu Lys Ser
225                 230                 235                 240
Asn Tyr Gln Ser His Gly Ile Tyr Arg Asp Ala Lys Thr Ala Phe Cys
            245                 250                 255
Ile His Asn Ile Ser Tyr Gln Gly Arg Phe Ala Phe Ser Asp Tyr Pro
            260                 265                 270
Glu Leu Asn Leu Pro Glu Arg Phe Lys Ser Ser Phe Asp Phe Ile Asp
            275                 280                 285
Gly Tyr Glu Lys Pro Val Glu Gly Arg Lys Ile Asn Trp Met Lys Ala
            290                 295                 300
Gly Ile Leu Glu Ala Asp Arg Val Leu Thr Val Ser Pro Tyr Tyr Ala
305                 310                 315                 320
Glu Glu Leu Ile Ser Gly Ile Ala Arg Gly Cys Glu Leu Asp Asn Ile
            325                 330                 335
Met Arg Leu Thr Gly Ile Thr Gly Ile Val Asn Gly Met Asp Val Ser
            340                 345                 350
Glu Trp Asp Pro Ser Arg Asp Lys Tyr Ile Ala Val Lys Tyr Asp Val
            355                 360                 365
Ser Thr Ala Val Glu Ala Lys Ala Leu Asn Lys Glu Ala Leu Gln Ala
            370                 375                 380
Glu Val Gly Leu Pro Val Asp Arg Asn Ile Pro Leu Val Ala Phe Ile
385                 390                 395                 400
Gly Arg Leu Glu Glu Gln Lys Gly Pro Asp Val Met Ala Ala Ala Ile
            405                 410                 415
Pro Gln Leu Met Glu Met Val Glu Asp Val Gln Ile Val Leu Leu Gly
            420                 425                 430
Thr Gly Lys Lys Lys Phe Glu Arg Met Leu Met Ser Ala Glu Glu Lys
            435                 440                 445
Phe Pro Gly Lys Val Arg Ala Val Val Lys Phe Asn Ala Ala Leu Ala
450                 455                 460
His His Ile Met Ala Gly Ala Asp Val Leu Ala Val Thr Ser Arg Phe
465                 470                 475                 480
Glu Pro Cys Gly Leu Ile Gln Leu Gln Gly Met Arg Tyr Gly Thr Pro
            485                 490                 495
Cys Ala Cys Ala Ser Thr Gly Gly Leu Val Asp Thr Ile Ile Glu Gly
            500                 505                 510
Lys Thr Gly Phe His Met Gly Arg Leu Ser Val Asp Cys Asn Val Val
            515                 520                 525
Glu Pro Ala Asp Val Lys Lys Val Ala Thr Thr Leu Gln Arg Ala Ile
            530                 535                 540
Lys Val Val Gly Thr Pro Ala Tyr Glu Glu Met Val Arg Asn Cys Met
545                 550                 555                 560
Ile Gln Asp Leu Ser Trp Lys Gly Pro Ala Lys Asn Trp Glu Asn Val
            565                 570                 575
Leu Leu Ser Leu Gly Val Ala Gly Gly Glu Pro Gly Val Glu Gly Glu
```

```
                580             585             590
       Glu Ile Ala Pro Leu Ala Lys Glu Asn Val Ala Pro
           595             600             605

<210> SEQ ID NO 5
<211> LENGTH: 36
<212> TYPE: DNA
<213> ORGANISM: Artificial
<220> FEATURE:
<223> OTHER INFORMATION: primer sequence

<400> SEQUENCE: 5
tcagccgttc gtgtggcaag attcatctgt tgtctc                               36

<210> SEQ ID NO 6
<211> LENGTH: 38
<212> TYPE: DNA
<213> ORGANISM: Artificial
<220> FEATURE:
<223> OTHER INFORMATION: primer sequence

<400> SEQUENCE: 6
tcagcgggat tatttactcc accactacag gtccattt                             38

<210> SEQ ID NO 7
<211> LENGTH: 4207
<212> TYPE: DNA
<213> ORGANISM: Zea mays

<400> SEQUENCE: 7
gttcgtgtgg cagattcatc tgttgtctcg tctcctgtgc ttcctgggta gcttgtgtag     60
tggagctgac atggtctgag caggcttaaa atttgctcgt agacgaggag taccagcaca    120
gcacgttgcg gatttctctg cctgtgaagt gcaacgtcta ggattgtcac acgccttggt    180
cgcgtcgcgt cgatgcggtg gtgagcagag cagcaacagc tgggcggccc aacgttggct    240
tccgtgtctt cgtcgtacgt acgcgcgcgc cggggacacg cagcgagcgg agaacgagcc    300
gtgcacgggg gaggtggtgt gcaagtggag ccgcgcgccc ggccgcccgc gcccggtggg    360
caacccaaaa gtacccacga caagcgaagg cgccaaagcg atccaagctc cggaacgcat    420
cagccacaag cagccgagaa ccgaaccggt gggcgacgcg tcgtgggacg gacgcgggcg    480
acgcttccaa acgggccacg tacgccggcg tgtgcgtgcg tgcgtgcaga cgacaagcca    540
aggcgaggca gccccgatc gggaaaaaag cgtcaagtag gtgcgccggg ctttggcttt    600
gggcgcgagc gctggcgtgc gggtcagtcg ctggtgcgca gtgccggggg gaacgggtat    660
cgtgggggcg cgggcggagg agagcgtggc gagggccgag agcagcgcgc ggccgggtca    720
cgcaacgcgc cccacgtact gccctccccc tccgcgcgcg ctagaaatac cgaggcctgg    780
accgggggcc ccccggcaca tccatccatc gaccgatcga tcgatcgcca cagccaacac    840
cacccgccga ggcgacgcga cagccgccag gaggaaggaa taaactcact gccagccagt    900 gaaggggggag aagtgtactg ctccgtcgac cagtgcgcgc accgcccggc agggctgctc    960
atctcgtcga cgaccaggtt ccgttccgtt ccgatcctgt ccttgagttt cgtccagata   1020
ctggcgtgta tctgcgtgtt tgatgatcca ggttcttcga acctaaatct gtccgtgcac   1080
atgtcctctc tctctctgtc tctctctgct atgcagtgga ttaatcggca tggcggctct   1140
ggccacgtcg cagctcgtcg caacgcgcgc cggcctgggc gtcccggacg cgtccacgtt   1200
ccgccgcggc gccgcgcagg gcctgagggg ggcccggggcg tcggcggcgg cggacacgct   1260
```

```
cagcatgcgg accagcgcgc gcgcggcgcc caggcaccag caccagcagg cgcgccgcgg    1320
ggccaggttc ccgtcgctcg tcgtgtgcgc cagcgccggc atgaacgtcg tcttcgtcgg    1380
cgccgagatg gcgccgtgga gcaagaccgg aggcctcggc gacgtcctcg gcggcctgcc    1440
gccggccatg gccgtaagcg cgcgcaccga gacatgcatc cgttggatcg cgtcttcttc    1500
gtgctcttgc cgcgtgcatg atgcatgtgt ttcctcctgg cttgtgttcg tgtatgtgac    1560
gtgtttgttc gggcatgcat gcaggcgaac gggcaccgtg tcatggtcgt ctctccccgc    1620
tacgaccagt acaaggacgc ctgggacacc agcgtcgtgt ccgaggtacg gccaccgaga    1680
ccagattcag atcacagtca cacacaccgt catgtgaacc tttctctgct ctgatgcctg    1740
caactgcaaa tgcatgcaga tcaagatggg agacgggtac gagacggtca ggttcttcca    1800
ctgctacaag cgcggagtgg accgcgtgtt cgttgaccac ccactgttcc tggagagggt    1860
gagacgagat ctgatcactc gatacgcaat taccaccca ttgtaagcag ttacagtgag    1920
ctttttttcc ccccggcctg gtcgctggtt tcaggtttgg ggaaagaccg aggagaagat    1980
ctacgggcct gtcgctggaa cggactacag ggacaaccag ctgcggttca gcctgctatg    2040
ccaggtcagg atggcttgct actacaactt cagatcatct gtatgcagca gtatacaccg    2100
atgagaaatg catgctgttc tgcaggcagc acttgaagct ccaaggatcc tgagcctcaa    2160
caacaaccca tacttctccg gaccatacgg taagagttgc tgctcttcgt ccatcagacg    2220
gactgtcatt ttacactgac tactgctgct gctcttcgtc catccataca aggggaggac    2280
gtcgtgttcg tctgcaacga ctggcacacc ggccctctct cgtgctacct caagagcaac    2340
taccagtccc acggcatcta cagggacgca aaggttgcct tctctgctga actgaacaac    2400
gccgccttcg ttctccatgc tcgtatatac ctcatctggt ggtggtgctt ctctgaaact    2460
gaaactgaaa ctgactgcat gtctgtctga ccatcttcac gtactaccta ccagaccgct    2520
ttctgcatcc acaacatctc ctaccagggc cggttcgcct ctccgactac ccggagctg     2580 aacctccccg agagattcaa gtcgtccttc gatttcatcg acgggtctgt tttcctgcgt    2640
gcatgtgaac attcatgaac ggtaacccac aactgttcgc gtcctgctgg ttcattatct    2700
gacctggatt gcattgcagc tacgagaagc ccgtggaagg ccggaagatc aactggatga    2760
aggccgggat cctcgaggcc gacagggtcc tcaccgtcag cccctactac gccgaggagc    2820
tcatctccgg catcgccagg ggctgcgagc tcgacaacat catgcgcctc accggcatca    2880
ccggcatcgt caacggcatg gacgtcagcg agtgggaccc cagcagggac aagtacatcg    2940
ccgtgaagta cgacgtgtcg acggtgagct ggctggctag ctgattctgc tgcctggtcc    3000
tcctgctcat gctggttcgg ttctgacgcg gcgagtgtac gtacgtgcgt gcgacggtgg    3060
tgtggtgtcc ggttcaggcc gtggaggcca aggcgctgaa caaggaggcg ctgcaggcgg    3120
aggtcgggct cccggtggac cggaacatcc cgctggtggc gttcatcggc aggctggaag    3180
agcagaaggg ccccgacgtc atggcggccg ccatcccgca gctcatggag atggtggagg    3240
acgtgcagat cgttctgctg gtacgtgtgc gccgcccgcc acccggctac tacatgcgtg    3300
tatcgttcta ctggaacata cgtgtgagca acgcgatgga taatgctgca gggcacgggc    3360
aagaagaagt tcgagcgcat gctcatgagc gccgaggaga agttcccagg caaggtgcgc    3420
gccgtggtca agttcaacgc ggcgctggcg caccacatca tggccggcgc cgacgtgctc    3480
gccgtcacca gccgcttcga gccctgcggc ctcatccagc tgcagggat gcgatacgga     3540 acggtacgag agagaaaaaa aacatcctga atccctgacg agagggacag agacagattg    3600
attatgaatg cttcatcgat ttgaattgat tgatcgatgt ctcccgctgc gactcttgca    3660
```

-continued

```
gccctgcgcc tgcgcgtcca ccggtggact cgtcgacacc atcatcgaag gcaagaccgg    3720
gttccacatg ggccgcctca gcgtcgacgt aagcctacct ctgccatgtt ctttcttctt    3780
tctttctgta tgtatgtatg tatgtacgaa tcagcaccgc cattcttgtt tcgtcgtcct    3840
ctcttcccag tgcaacgtcg tggagccggc ggacgtcaag aaggtggcca ccaccttgca    3900
gcgcgccatc aaggtggtcg gcacgccggc gtacgaggag atggtgagga actgcatgat    3960
ccaggatctc tcctggaagg tacgtacgcc cgccccgcca gagcagagcg ccaagatcga    4020
tcgatcgacc gaccacacgt acgcgcctcg ctcttgtcgc tgaccgtggt ttaatttgcg    4080
aaatgcgcag ggccctgcca agaactggga gaacgtgctg ctcagcctcg ggtcgccgg    4140 cggcgagcca ggggttgaag gcgaggagat cgcgccgctc gccaaggaga acgtggccgc    4200
gccctga                                                              4207
```

<210> SEQ ID NO 8
<211> LENGTH: 606
<212> TYPE: PRT
<213> ORGANISM: Zea mays

<400> SEQUENCE: 8

```
Met Ala Ala Leu Ala Thr Ser Gln Leu Val Ala Thr Arg Ala Gly Leu
1               5                   10                  15

Gly Val Pro Asp Ala Ser Thr Phe Arg Arg Gly Ala Ala Gln Gly Leu
            20                  25                  30

Arg Gly Ala Arg Ala Ser Ala Ala Ala Asp Thr Leu Ser Met Arg Thr
        35                  40                  45

Ser Ala Arg Ala Ala Pro Arg His Gln His Gln Gln Ala Arg Arg Gly
    50                  55                  60

Ala Arg Phe Pro Ser Leu Val Val Cys Ala Ser Ala Gly Met Asn Val
65                  70                  75                  80

Val Phe Val Gly Ala Glu Met Ala Pro Trp Ser Lys Thr Gly Gly Leu
                85                  90                  95

Gly Asp Val Leu Gly Gly Leu Pro Pro Ala Met Ala Ala Asn Gly His
            100                 105                 110

Arg Val Met Val Val Ser Pro Arg Tyr Asp Gln Tyr Lys Asp Ala Trp
        115                 120                 125

Asp Thr Ser Val Val Ser Glu Ile Lys Met Gly Asp Gly Tyr Glu Thr
    130                 135                 140

Val Arg Phe Phe His Cys Tyr Lys Arg Gly Val Asp Arg Val Phe Val
145                 150                 155                 160

Asp His Pro Leu Phe Leu Glu Arg Val Trp Gly Lys Thr Glu Glu Lys
                165                 170                 175

Ile Tyr Gly Pro Val Ala Gly Thr Asp Tyr Arg Asp Asn Gln Leu Arg
            180                 185                 190

Phe Ser Leu Leu Cys Gln Ala Ala Leu Glu Ala Pro Arg Ile Leu Ser
        195                 200                 205

Leu Asn Asn Asn Pro Tyr Phe Ser Gly Pro Tyr Gly Glu Asp Val Val
    210                 215                 220

Phe Val Cys Asn Asp Trp His Thr Gly Pro Leu Ser Cys Tyr Leu Lys
225                 230                 235                 240

Ser Asn Tyr Gln Ser His Gly Ile Tyr Arg Asp Ala Lys Thr Ala Phe
                245                 250                 255

Cys Ile His Asn Ile Ser Tyr Gln Gly Arg Phe Ala Phe Ser Asp Tyr
            260                 265                 270
```

```
Pro Glu Leu Asn Leu Pro Glu Arg Phe Lys Ser Ser Phe Asp Phe Ile
        275                 280                 285

Asp Gly Tyr Glu Lys Pro Val Glu Gly Arg Lys Ile Asn Trp Met Lys
        290                 295                 300

Ala Gly Ile Leu Glu Ala Asp Arg Val Leu Thr Val Ser Pro Tyr Tyr
305                 310                 315                 320

Ala Glu Glu Leu Ile Ser Gly Ile Ala Arg Gly Cys Glu Leu Asp Asn
                325                 330                 335

Ile Met Arg Leu Thr Gly Ile Thr Gly Ile Val Asn Gly Met Asp Val
                340                 345                 350

Ser Glu Trp Asp Pro Ser Arg Asp Lys Tyr Ile Ala Val Lys Tyr Asp
        355                 360                 365

Val Ser Thr Ala Val Glu Ala Lys Ala Leu Asn Lys Glu Ala Leu Gln
        370                 375                 380

Ala Glu Val Gly Leu Pro Val Asp Arg Asn Ile Pro Leu Val Ala Phe
385                 390                 395                 400

Ile Gly Arg Leu Glu Glu Gln Lys Gly Pro Asp Val Met Ala Ala Ala
                405                 410                 415

Ile Pro Gln Leu Met Glu Met Val Glu Asp Val Gln Ile Val Leu Leu
                420                 425                 430

Gly Thr Gly Lys Lys Lys Phe Glu Arg Met Leu Met Ser Ala Glu Glu
        435                 440                 445

Lys Phe Pro Gly Lys Val Arg Ala Val Val Lys Phe Asn Ala Ala Leu
        450                 455                 460

Ala His His Ile Met Ala Gly Ala Asp Val Leu Ala Val Thr Ser Arg
465                 470                 475                 480

Phe Glu Pro Cys Gly Leu Ile Gln Leu Gln Gly Met Arg Tyr Gly Thr
                485                 490                 495

Pro Cys Ala Cys Ala Ser Thr Gly Gly Leu Val Asp Thr Ile Ile Glu
                500                 505                 510

Gly Lys Thr Gly Phe His Met Gly Arg Leu Ser Val Asp Cys Asn Val
        515                 520                 525

Val Glu Pro Ala Asp Val Lys Lys Val Ala Thr Thr Leu Gln Arg Ala
        530                 535                 540

Ile Lys Val Val Gly Thr Pro Ala Tyr Glu Met Val Arg Asn Cys
545                 550                 555                 560

Met Ile Gln Asp Leu Ser Trp Lys Gly Pro Ala Lys Asn Trp Glu Asn
                565                 570                 575

Val Leu Leu Ser Leu Gly Val Ala Gly Gly Glu Pro Gly Val Glu Gly
                580                 585                 590

Glu Glu Ile Ala Pro Leu Ala Lys Glu Asn Val Ala Ala Pro
        595                 600                 605

<210> SEQ ID NO 9
<211> LENGTH: 28
<212> TYPE: DNA
<213> ORGANISM: Artificial
<220> FEATURE:
<223> OTHER INFORMATION: primer sequence

<400> SEQUENCE: 9
ggatatcacc atggcggctc tggccacg                                    28

<210> SEQ ID NO 10
<211> LENGTH: 27
```

<212> TYPE: DNA
<213> ORGANISM: Artificial
<220> FEATURE:
<223> OTHER INFORMATION: primer sequence

<400> SEQUENCE: 10
gtcctgcagg ctacacatac ttgtcca                                27

<210> SEQ ID NO 11
<211> LENGTH: 1863
<212> TYPE: DNA
<213> ORGANISM: Zea mays

<400> SEQUENCE: 11

| | | | | | |
|---|---|---|---|---|---|
| atggcggctc | tggccacgtc | gcagctcgtc | gcaacgcgcg | ccggcctggg | cgtcccggac | 60 |
| gcgtccacgt | tccgccgcgg | cgccgcgcag | ggcctgaggg | gggcccgggc | gtcggcggcg | 120 |
| gcggacacgc | tcagcatgcg | gaccagcgcg | cgcgcggcgc | ccaggctcca | gctgcaccag | 180 |
| cagcagcagc | aggcgcgccg | cggggccagg | ttcccgtcgc | tcgtcgtgtg | cgccagcgcc | 240 |
| ggcatgaacg | tcgtcttcgt | cggcgccgag | atggcgccgt | ggagcaagac | cggcggcctc | 300 |
| ggcgacgtcc | tcggcggcct | gccgccggcc | atggccgcga | atgggcaccg | tgtcatggtc | 360 |
| gtctctcccc | gctacgacca | gtacaaggac | gcctgggaca | ccagcgtcgt | gtccgagatc | 420 |
| aagatgggag | acaggtacga | gacggtcagg | ttcttccact | gctacaagcg | cggagtggac | 480 |
| cgcgtgttcg | ttgaccaccc | actgttcctg | gagagggttt | ggggaaagac | cgaggagaag | 540 |
| atctacgggc | ctgtcgctgg | aacgactac | agggacaacc | agctgcggtt | cagcctgcta | 600 |
| tgccaggcag | cacttgaagc | tccaaggatc | ctgagcctca | caacaaccc | atacttctcc | 660 |
| ggaccatacg | gggaggacgt | cgtgttcgtc | tgcaacgact | ggcacaccgg | ccctctctcg | 720 |
| tgctacctca | agagcaacta | ccagtcccac | ggcatctaca | gggacgcaaa | gaccgctttc | 780 |
| tgcatccaca | acatctccta | ccagggccgg | ttcgccttct | ccgactaccc | ggagctgaac | 840 |
| ctccccgaga | gattcaagtc | gtccttcgat | tcatcgacg | gctacgagaa | gcccgtggaa | 900 |
| ggccggaaga | tcaactggat | gaaggccggg | atcctcgagg | ccgacaggg | cctcaccgtc | 960 |
| agcccctact | acgccgagga | gctcatctcc | ggcatcgcca | gggctgcga | gctcgacaac | 1020 |
| atcatgcgcc | tcaccggcat | caccggcatc | gtcaacggca | tggacgtcag | cgagtgggac | 1080 |
| cccagcaggg | acaagtacat | cgccgtgaag | tacgacgtgt | cgacggccgt | ggaggccaag | 1140 |
| gcgctgaaca | aggaggcgct | gcaggcggag | gtcgggctcc | cggtggaccg | gaacatcccg | 1200 |
| ctggtggcgt | tcatcggcag | gctggaagag | cagaagggcc | ccgacgtcat | ggcggccgcc | 1260 |
| atcccgcagc | tcatggagat | ggtggaggac | gtgcagatcg | ttctgctggg | cacgggcaag | 1320 |
| aagaagttcg | agcgcatgct | catgagcgcc | gaggagaagt | tcccaggcaa | ggtgcgcgcc | 1380 |
| gtggtcaagt | tcaacgcggc | gctggcgcac | cacatcatgg | ccggcgccga | cgtgctcgcc | 1440 |
| gtcaccagcc | gcttcgagcc | ctgcggcctc | atccagctgc | aggggatgcg | atacggaacg | 1500 |
| ccctgcgcct | cgcgtccac | cggtggactc | gtcgacacca | tcgaaggg | caagaccggg | 1560 |
| ttccacatgg | gccgcctcag | cgtcgactgc | aacgtcgtgg | agccggcgga | cgtcaagaag | 1620 |
| gtggccacca | ccttgcagcg | cgccatcaag | gtggtcggca | cgccggtgta | cgaggagatg | 1680 |
| gtgaggaact | gcatgatcca | ggatctctcc | tggaagggcc | ctgccaagaa | ctgggagaac | 1740 |
| gtgctgctca | gcctcgggt | cgccggcggt | gcaggccc | tgatctcgcg | cgtggtgcaa | 1800 |
| agatgttggg | acatcttctt | atatatgctg | tttcgtttat | gtgatatgga | caagtatgtg | 1860 |

-continued tag                                                              1863

<210> SEQ ID NO 12
<211> LENGTH: 31
<212> TYPE: DNA
<213> ORGANISM: Artificial
<220> FEATURE:
<223> OTHER INFORMATION: primer sequence

<400> SEQUENCE: 12
ggcgcgccgt cgacggtatc gataagcttg c                               31

<210> SEQ ID NO 13
<211> LENGTH: 32
<212> TYPE: DNA
<213> ORGANISM: Artificial
<220> FEATURE:
<223> OTHER INFORMATION: primer sequence

<400> SEQUENCE: 13
gcggccgccc gcttggtatc tgcattacaa tg                              32

<210> SEQ ID NO 14
<211> LENGTH: 32
<212> TYPE: DNA
<213> ORGANISM: Artificial
<220> FEATURE:
<223> OTHER INFORMATION: primer sequence

<400> SEQUENCE: 14
gatcgtttaa acgttcgtgt ggcagattca tc                              32

<210> SEQ ID NO 15
<211> LENGTH: 41
<212> TYPE: DNA
<213> ORGANISM: Artificial
<220> FEATURE:
<223> OTHER INFORMATION: primer sequence

<400> SEQUENCE: 15
gacgtggcca gagccgccat gccgattaat ccactgcata g                    41

<210> SEQ ID NO 16
<211> LENGTH: 20
<212> TYPE: DNA
<213> ORGANISM: Artificial
<220> FEATURE:
<223> OTHER INFORMATION: primer sequence

<400> SEQUENCE: 16
atcttgctcg atgccttctc                                            20

<210> SEQ ID NO 17
<211> LENGTH: 19
<212> TYPE: DNA
<213> ORGANISM: Artificial
<220> FEATURE:
<223> OTHER INFORMATION: primer sequence

<400> SEQUENCE: 17
gccttcgctt gtcgtgggt                                             19

ELEVATION OF OIL LEVELS IN PLANTS

This application claims the benefit of the filing date of the Provisional Application U.S. Ser. No. 60/483,491, filed Jun. 27, 2003, which is incorporated herein by reference.

The present invention relates to the fields of nucleic acid chemistry and agricultural biotechnology. In particular, the present invention is directed at the identification of nucleic acids that encode proteins useful for increasing oil levels in maize plants and creating maize plants that include such nucleic acids.

Plants are a major source of oils for feed, food, and industrial uses. While tissues of most plant species contain little oil, the cultivation of certain plant types, over many acres, permit large quantities of plant oils to be produced. If the oil content of these plants could be increased, then plant oils could be produced more efficiently. For example, the normal oil content of yellow #2, dent corn is about 4%. If the oil content of corn could be increased to 8% or even 12%, without significantly affecting yield, the same amount of oil could be produced from half or even one-third the number of acres.

Currently, levels of oil in oilseed crops have increased incrementally by traditional breeding and selection methods. There exist few references to transgenic plants with increased levels of oil. In contrast, increases in the proportions of some strategic fatty acids have been achieved by the introduction or manipulation of various plant fatty acid biosynthesis genes in oilseeds. For instance, Voelker et al., *Science*, 257:72–74 (1992), demonstrated that expression in *Brassicaceae* of a medium chain fatty acyl-ACP thioesterase from California Bay, increased the lauric acid (12:0) content. Hitz et al., Proc. 9$^{th}$ International Cambridge Rapeseed Congress UK, pp 470–472 (1995) increased proportions of oleic acid in *Glycine max* by co-suppression using a sense construct encoding a plant microsomal FAD-2 (Δ12) desaturase. Although the use of these plant transgenes resulted in an increased production of lauric acid in canola and altered proportions of oleic acid in soy, there was no evidence of increased total fatty acid content, or increased oil yield in these transgenics.

Certain workers have attempted to increase or modulate the oil content of plants by manipulation of oil biosynthetic pathway genes. For example, U.S. Pat. No. 6,268,550 to Gengenbach et al. provides maize acetyl CoA carboxylase nucleic acids for altering the oil content of plants. Additionally, U.S. Pat. No. 5,925,805 to Ohlrogge et al. provides an *Arabidopsis* acetyl CoA carboxylase gene that can be used to increase the oil content of plants. However, the synthesis of fatty acids requires the coordinated activity of many enzymes, none of which when solely upregulated has been found to substantially increase oil content.

A need therefore exists for an improved method to alter the oil content of plants, and in particular to increase the oil content of plants and seeds.

In addition to oil, starch from maize is also agriculturally and commercially significant. Starch comprises a major component of animal feed and human food. Starch is also used industrially in the production of paper, textiles, plastics, and adhesives, as well as providing the raw material for some bioreactors.

In higher plants, the starch consists of linear chain and branched chain glucans known as amylose and amylopectin, respectively. Starch with various amounts of amylose and amylopectin are found in different plants. Typically, maize starch contains approximately 25% amylose, the remainder being amylopectin. Amylopectin contains short chains and long chains, the short chains ranging from 5–30 glucose units and the long chains ranging from 30–100 glucose units, or more. The ratio of amylose to amylopectin, as well as the distribution of short to long chains in the amylopectin fraction, affect the physical properties of starch, (e.g., thermal stabilization, retrogradation, and viscosity).

The WAXY locus of maize determines the amylose content in pollen and in kernel endosperm, (Shure et al., *Cell*, 35(1):225–233 (1983)), resulting in starch having unique properties. Most mutations in the WAXY locus of maize, which encodes granule bound starch synthase (GBSS), result in an opaque endosperm of smooth, firm non-corneous starch comprising mostly amylopectin and a reduced amount of amylose in the endosperm, pollen and embryo sac ("WAXY phenotype") (see, Okagaki and Wessler, *Genetics*, 120(4): 1137–1143 (1988)). When no functioning GBSS is synthesized in the homozygous WAXY mutant, it also lacks amylose (Echt and Schwartz, *Genetics*, 99:275–284 (1981)).

Additionally, classic, recessive WAXY has a small (approximately 0.5% increase) effect on percent oil in the kernel when compared to yellow #2 corn (Pfahler and Linskens, *Theoretical and Applied Genetics*, 41(1):2–4 (1971)). In comparison, the inbred line HOI001, a dominant WAXY mutant inbred described in U.S. Patent Publication No. 20030172416, herein incorporated by reference, has whole kernel oil concentrations greater than four times that of yellow #2 corn.

SUMMARY OF THE INVENTION

The present invention describes and provides isolated nucleic acid molecules encoding an HOI001 GBSS polypeptide. In addition, this invention relates to nucleic acid molecules that are complementary to the nucleic acid molecule encoding an HOI001 GBSS polypeptide. In addition, this invention relates to expression cassettes comprising these nucleic acid molecules. In addition, this invention relates to transgenic maize plants containing these expression cassettes. In addition, this invention relates to the seeds of these transgenic maize plants. This invention further relates to the oil and animal feed obtained from the seeds of these transgenic maize plants.

In another embodiment, the present invention relates to a recombinant DNA construct, associated with increased oil production in plants, comprising a nucleic acid molecule encoding an HOI001 GBSS polypeptide operably linked to a promoter, which is functional in a plant cell.

The present invention describes and provides a method of increasing oil in a maize plant by expression of an HOI001 GBSS gene. This invention further provides a method of altering the kernel composition in a corn plant by expression of an HOI001 GBSS gene. This invention further describes and provides sequences of an HOI001 GBSS gene from *Zea mays*. This invention further provides vector constructs for plant transformation and tissue-specific expression of an HOI001 GBSS gene. This invention further provides maize plants transformed with the GBSS gene with higher oil levels when compared to plants with the same or similar genetic background, but not containing the inserted HOI001 GBSS gene. This invention further provides seeds from these maize plants. This invention further provides for kernels from maize plants transformed with the HOI001 GBSS gene containing a higher level of oil when compared to kernels from corn plants with the same or similar genetic background, but not containing the inserted HOI001 GBSS gene. This invention also provides oil and animal feed produced from these seeds and kernels.

The present invention further provides a method of marker-assisted breeding useful in breeding higher oil levels in maize.

BRIEF DESCRIPTION OF THE FIGURES

FIG. 2 shows the alignment of the corresponding predicted amino acid sequences from the GBSS gene isolated from HOI001 (HOI001 GBSS from pMON72506) [SEQ ID NO: 3], and the GBSS gene described in Shure et al., supra, [SEQ ID NO: 4], respectively.

FIG. 3 shows the alignment of the corresponding predicted amino acid sequences from the Zea mays GBSS gene isolated from inbred LH59 [SEQ ID NO: 10], and the Zea mays granule bound starch synthase gene described in Shure et al., supra, respectively.

BRIEF DESCRIPTION OF THE SEQUENCES

Figure 1:
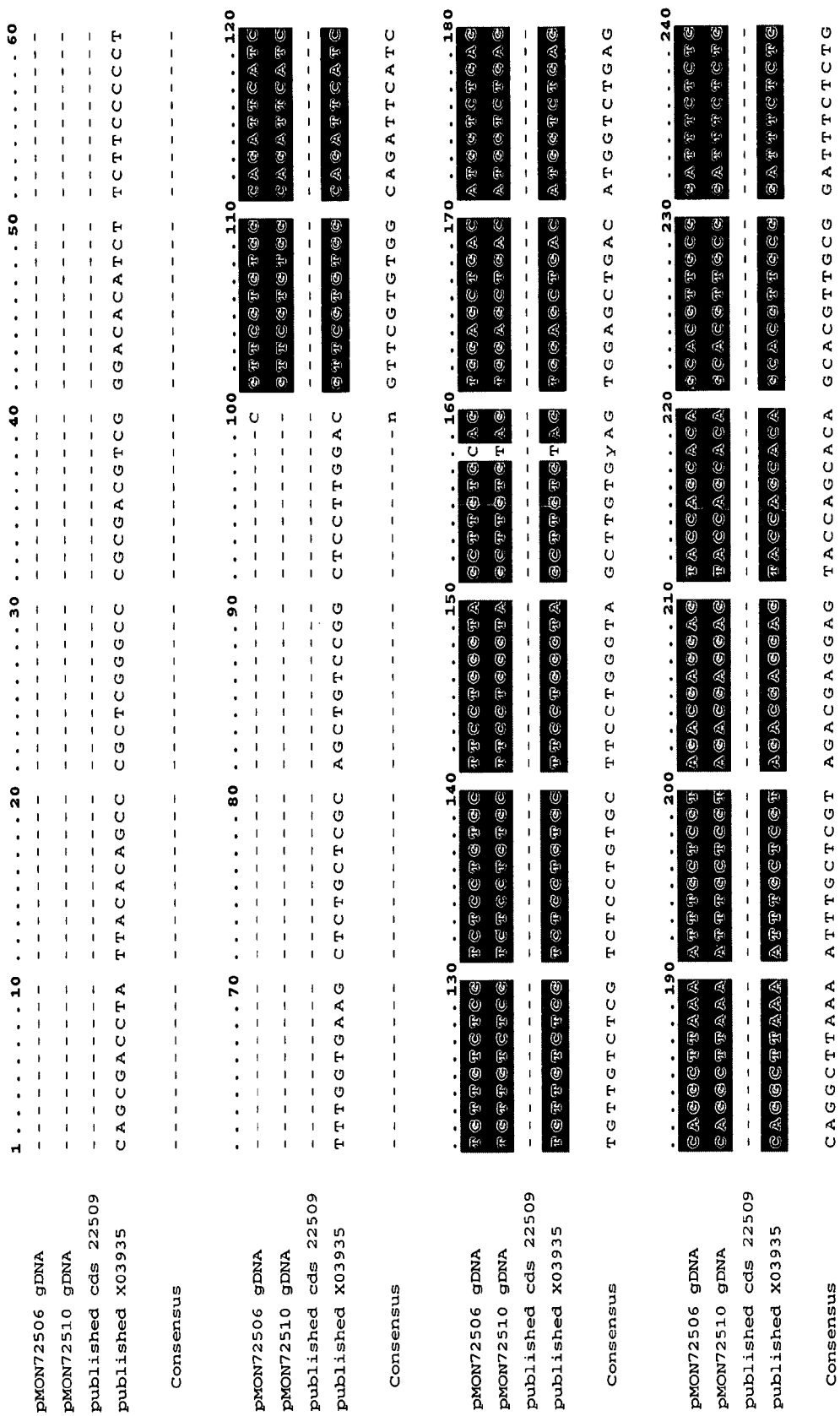
FIG. 1 shows the nucleic acid sequence alignment of the granule bound starch synthase gene isolated from HOI001 (HOI001 GBSS, pMON72506) [SEQ ID NO: 1] compared to the granule bound starch synthase (GBSS) gene from inbred LH59 (pMON72510), and published sequence of the GBSS gene described in Shure et al., supra, (X03935). For additional comparison, the coding sequence for the published GBSS gene is given (CDS22509).
Figure 1:
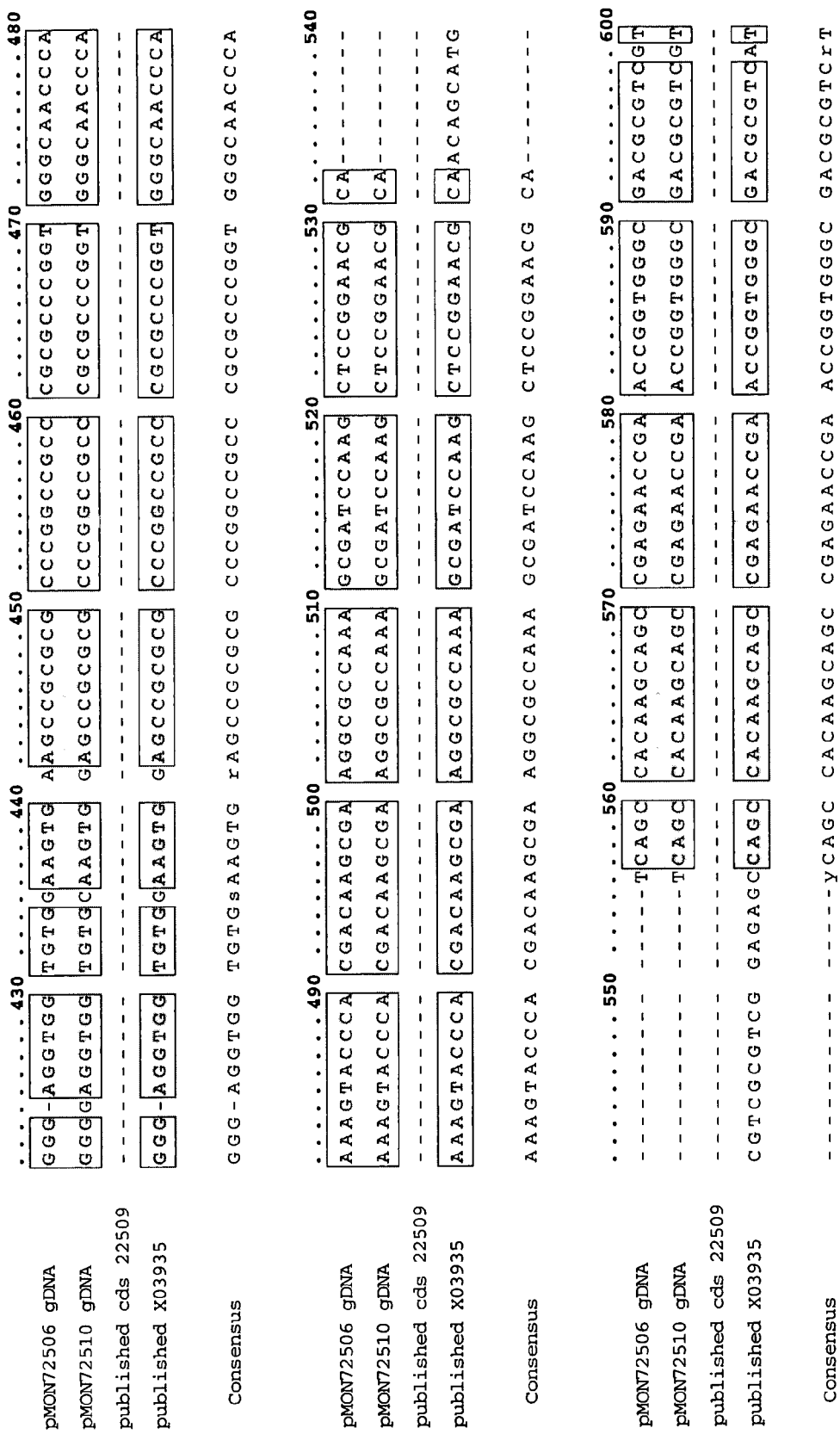
Figure 1:
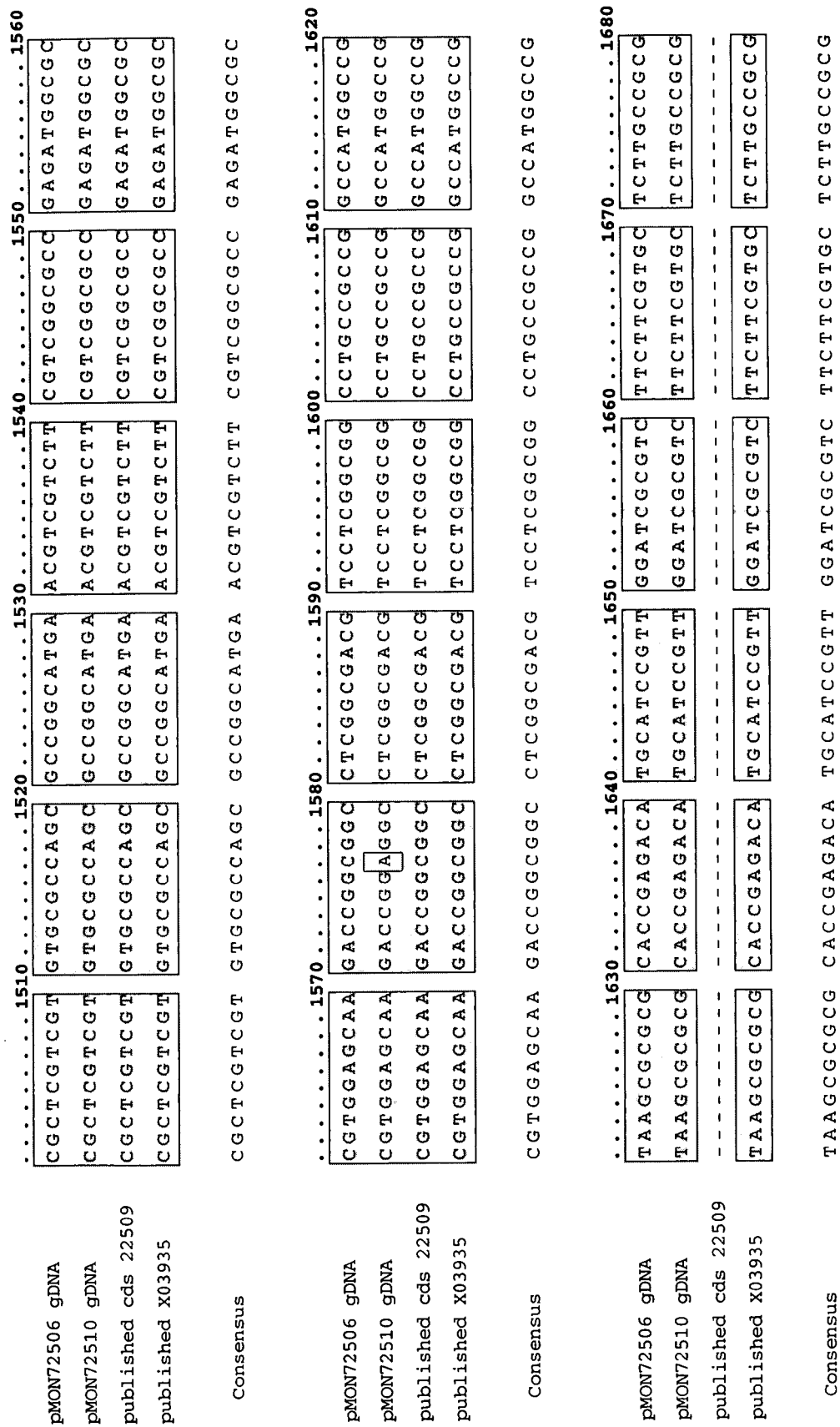
Figure 1:
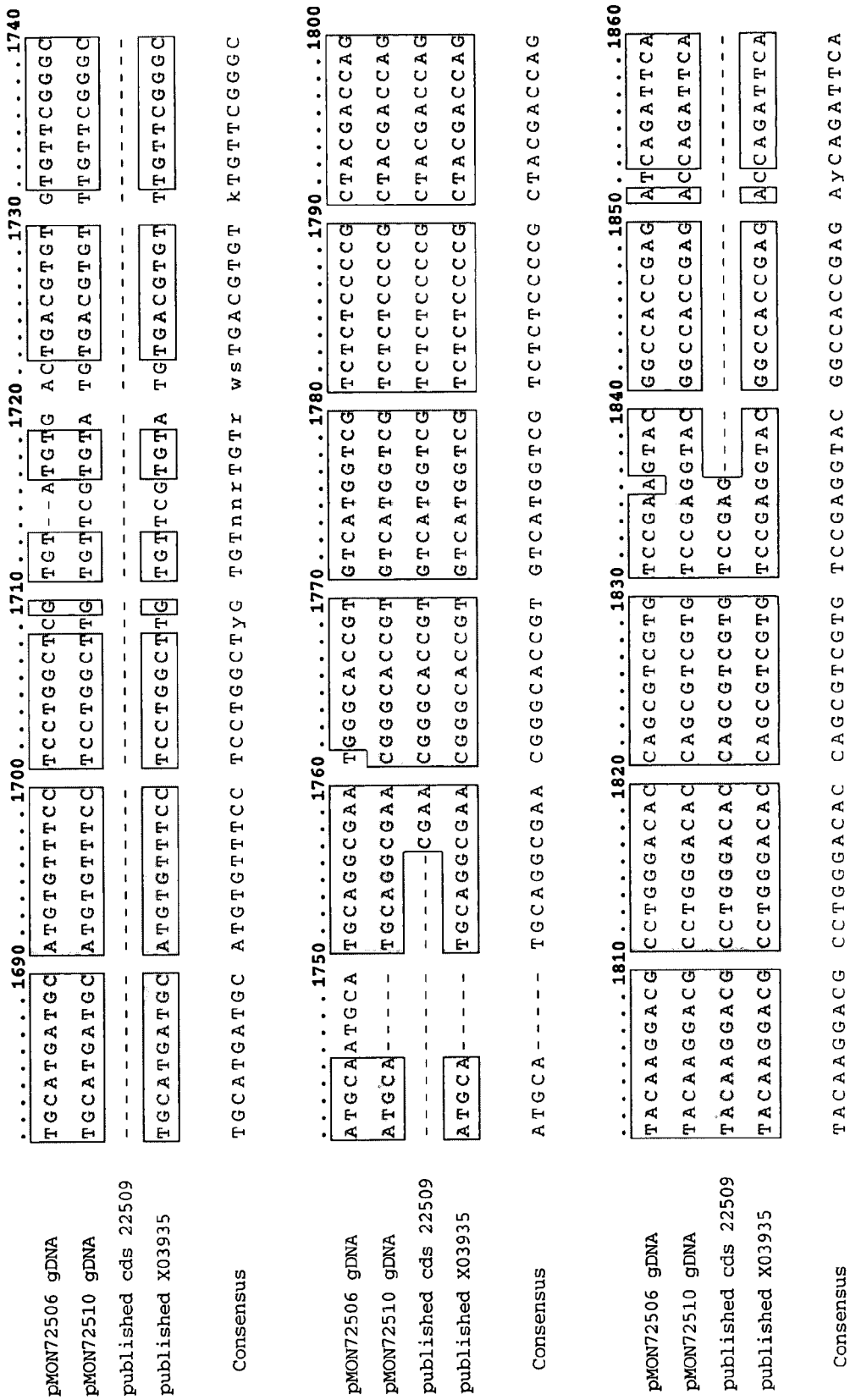
Figure 1:
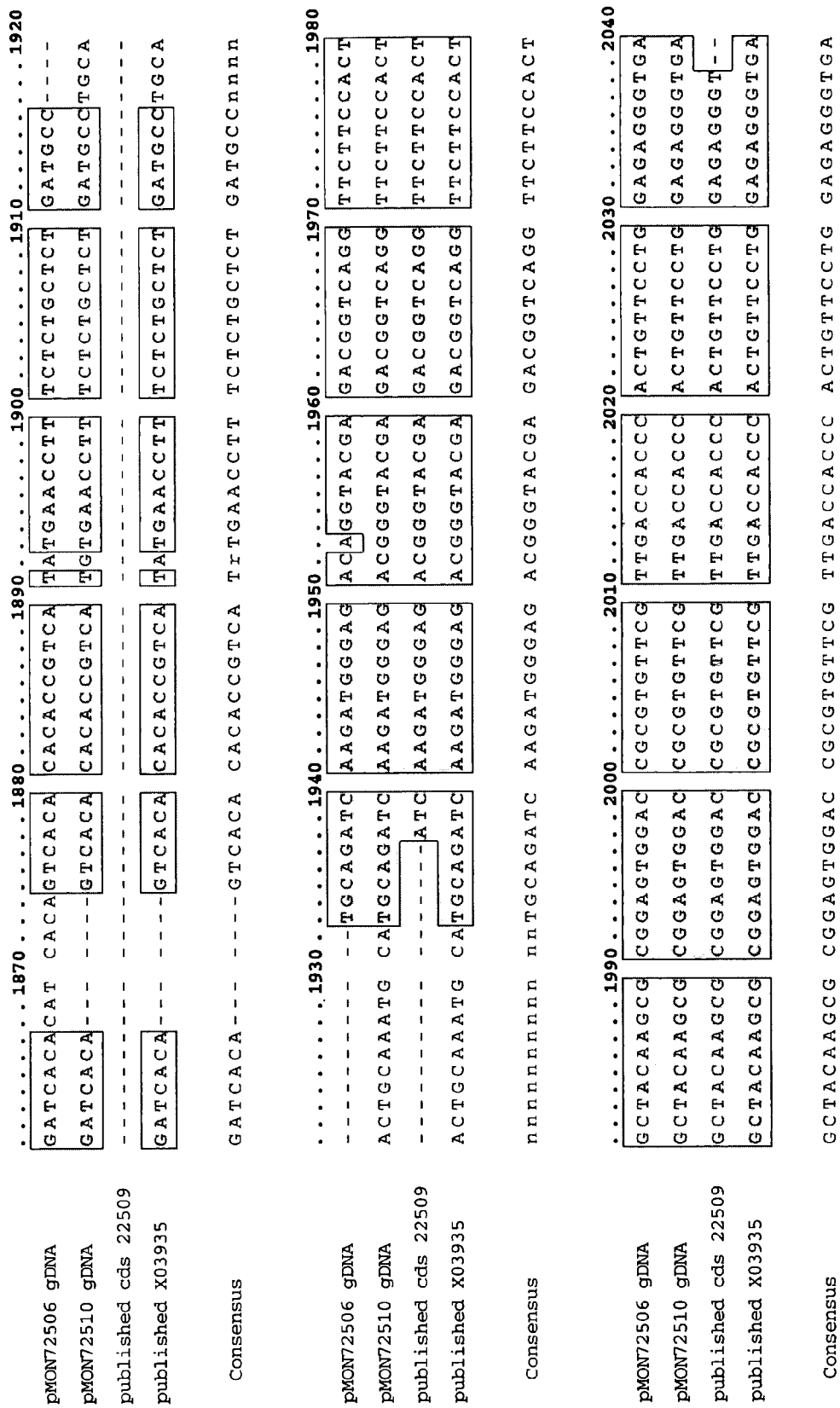
Figure 1:
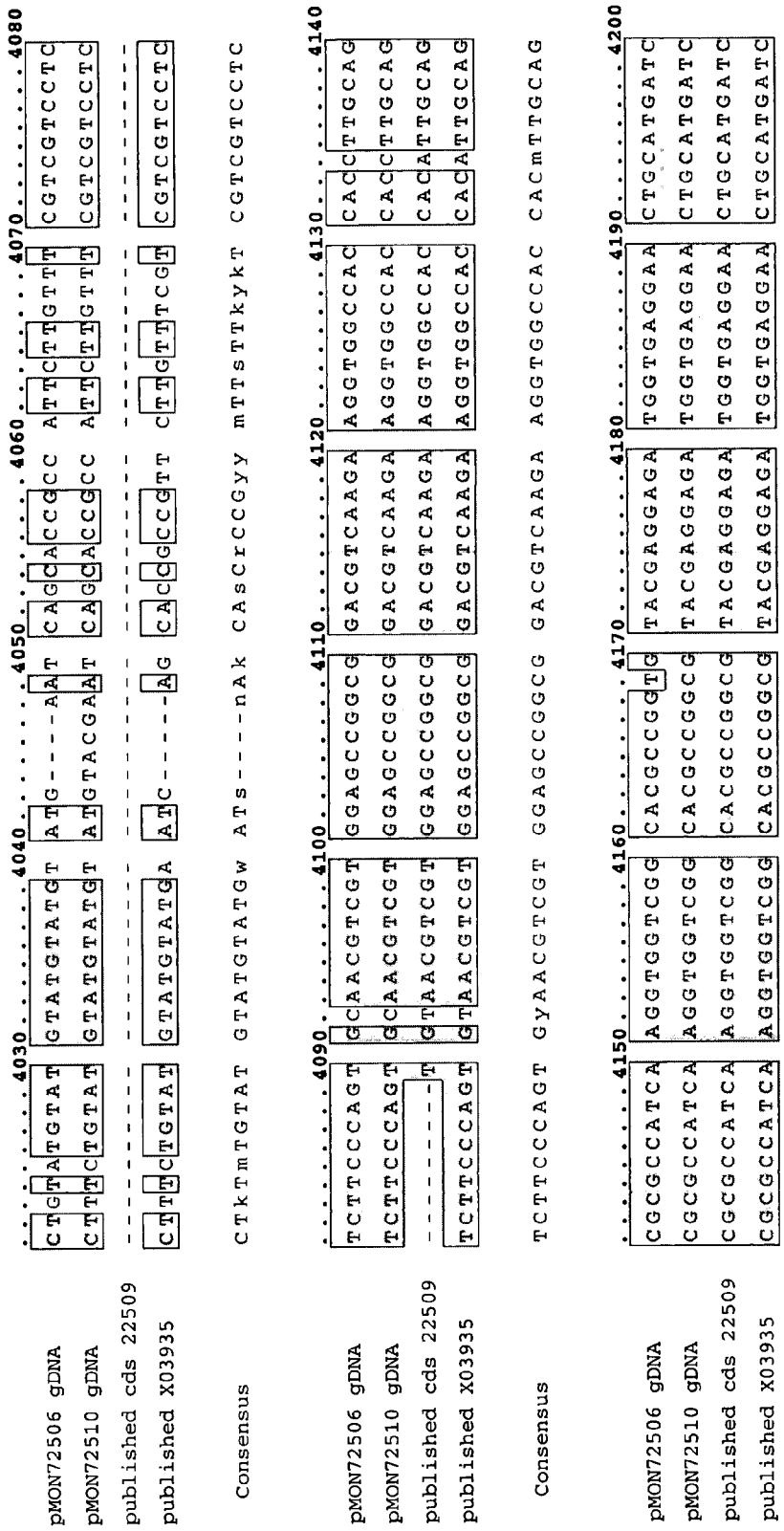
Figure 1:
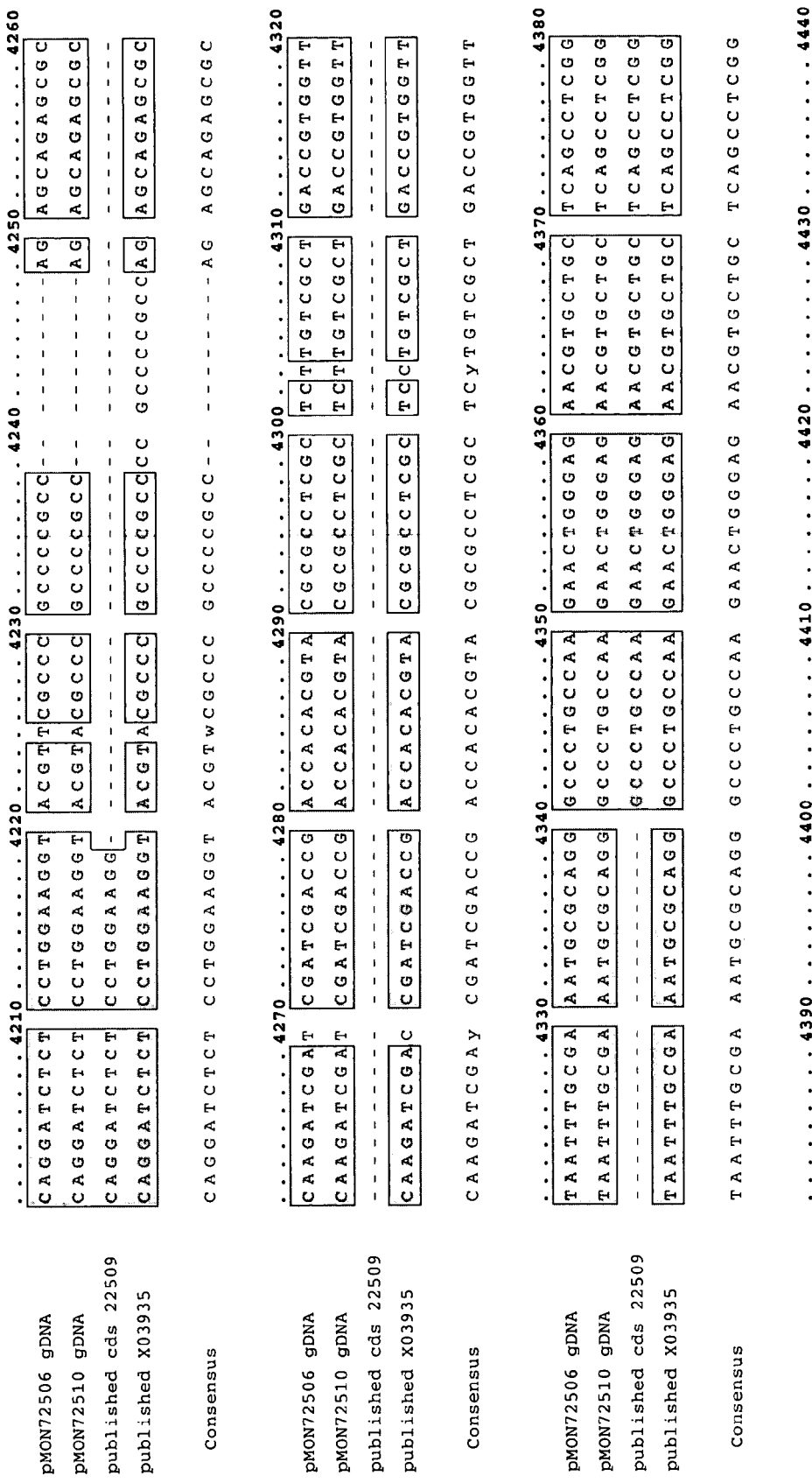

SEQ ID NO: 1 is the nucleic acid sequence of the granule bound starch synthase from HOI001 (HOI001 GBSS from pMON72506).

SEQ ID NO: 2 is the published nucleic acid sequence of Zea mays GBSS from Shure et al., supra.

SEQ ID NO: 3 sets forth the predicted amino acid sequence of HOI001 GBSS from pMON72506.

SEQ ID NO: 4 sets forth the predicted amino acid sequence from the Zea mays GBSS as published by Shure et al., supra.

SEQ ID NO: 5 is a primer sequence for Primer number 14543.

SEQ ID NO: 6 is a primer sequence for Primer number 14547.

SEQ ID NO: 7 sets forth a nucleic acid sequence of a DNA molecule that encodes a GBSS from corn line LH59.

SEQ ID NO: 8 sets forth the predicted amino acid sequence of GBSS from corn line LH59.

SEQ ID NO: 9 is a primer sequence for Primer number 20095.

SEQ ID NO: 10 is a primer sequence for Primer number 20092.

SEQ ID NO: 11 sets forth the coding region of the GBSS cDNA of HOI001.

DETAILED DESCRIPTION OF THE INVENTION

The following definitions are provided as an aid to understanding the detailed description of the present invention.

The phrases "coding sequence," "coding region," "structural sequence," and "structural nucleic acid sequence" refer to a physical structure comprising an orderly arrangement of nucleotides. The nucleotides are arranged in a series of triplets that each form a codon. Each codon encodes a specific amino acid. Thus, the coding sequence, structural sequence, and structural nucleic acid sequence encode a series of amino acids forming a protein, polypeptide, or peptide sequence. The coding sequence, structural sequence, and structural nucleic acid sequence may be contained within a larger nucleic acid molecule, vector, or the like. In addition, the orderly arrangement of nucleotides in these sequences may be depicted in the form of a sequence listing, figure, table, electronic medium, or the like.

The phrase "codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

The term "cDNA" refers to a double-stranded DNA that is complementary to and derived from mRNA.

The phrases "DNA sequence," "nucleic acid sequence," and "nucleic acid molecule" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

"Expression" refers to the transcription of a gene to produce the corresponding mRNA and translation of this mRNA to produce the corresponding gene product (i.e., a peptide, polypeptide, or protein).

"Expression of antisense RNA" refers to the transcription of a DNA to produce a first RNA molecule capable of hybridizing to a second RNA molecule, which second RNA molecule encodes a gene product that is desirably down-regulated.

As used herein, "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. An "exogenous gene" or "transgene" refer to a non-native gene that has been introduced into the genome by a transformation procedure.

"Hemizygous" refers to a diploid individual having only one copy of a particular gene (for example, because a chromosome has been lost). "Homozygous" refers to a gene pair having identical alleles in two homologous chromosomes.

"Heterologous" refers to the relationship between two or more nucleic acid or protein sequences that are derived from different sources. For example, a promoter is heterologous with respect to a coding sequence if such a combination is not normally found in nature. In addition, a particular sequence may be "heterologous" with respect to a cell or organism into which it is inserted (i.e., does not naturally occur in that particular cell or organism).

"Homology" refers to the level of similarity between two or more nucleic acid or amino acid sequences in terms of percent of positional identity (i.e., sequence similarity or identity). Homology also refers to the concept of similar functional properties among different nucleic acids or proteins.

"Hybridization" refers to the ability of a first strand of nucleic acid to join with a second strand via hydrogen bond base pairing when the two nucleic acid strands have sufficient sequence complementarity. As used herein, a nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Thus two nucleic acid strands are said to have sufficient complementarity when they can hybridize to one another with sufficient stability to permit them to remain annealed to one another under appropriate conditions.

The phrases "marker-assisted selection" or "marker-assisted breeding" refer to the use of genetic markers to identify and select plants with superior phenotypic potential. Genetic markers determined previously to be associated with a trait locus or trait loci are used to uncover the genotype at trait loci by virtue of linkage between the marker locus and the trait locus. Plants containing desired trait alleles are chosen based upon their genotypes at linked marker loci.

The phrase "breeding population" refers to a genetically heterogeneous collection of plants created for the purpose of identifying one or more individuals with desired phenotypic characteristics. The term "phenotype" refers to the observed expression of one or more plant characteristics.

A "genetic marker" is any morphological, biochemical, or nucleic acid based phenotypic difference which reveals a DNA polymorphism. Examples of genetic markers include but are not limited to RFLPs, RAPDs, allozymes, SSRs, and AFLPs.

The phrase "marker locus" refers to the genetically defined location of DNA polymorphisms as revealed by a genetic marker. A "trait locus" refers to a genetically defined location for a collection of one or more genes (alleles) which contribute to an observed characteristic.

The phrase "restriction fragment length polymorphism" (RFLP) refers to a DNA-based genetic marker in which size differences in restriction endonuclease generated DNA fragments are observed via hybridization (Botstein et al., *Am. J. Hum. Genet.*, 32:314–331 (1980)).

The phrase "random amplified polymorphic DNA" (RAPD) refers to a DNA amplification based genetic marker in which short, sequence arbitrary primers are used and the resulting amplification products are size separated and differences in amplification patterns observed (Williams et al., *Nucleic Acids Res.*, 18:6531–6535 (1990)).

The phrase "simple sequence repeat" (SSR) refers to a DNA amplification-based genetic marker in which short stretches of tandemly repeated sequence motifs are amplified and the resulting amplification products are size separated and differences in length of the nucleotide repeat are observed (Tautz, *Nucleic Acids Res.*, 112:4127–4138 (1989)).

The term "AFLP" refers to a DNA amplification-based genetic marker in which restriction endonuclease generated DNA fragments are ligated to short DNA fragments which facilitate the amplification of the restricted DNA fragments (Vos et al., *Nucleic Acids Res.*, 23:4407–4414 (1995)). The amplified fragments are size separated and differences in amplification patterns observed.

The phrase "operably linked" refers to the functional spatial arrangement of two or more nucleic acid regions or nucleic acid sequences. For example, a promoter region may be positioned relative to a nucleic acid sequence such that transcription of the nucleic acid sequence is directed by the promoter region. Thus, a promoter region is "operably linked" to the nucleic acid sequence.

The terms "promoter" or "promoter region" refer to a nucleic acid sequence, usually found upstream (5') to a coding sequence that is capable of directing transcription of a nucleic acid sequence into mRNA. The promoter or promoter region typically provides a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, and the like. The activity or strength of a promoter may be measured in terms of the amounts of RNA it produces, or the amount of protein accumulation in a cell or tissue, relative to a second promoter that is similarly measured.

The phrase "3' non-coding sequences" refers to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell*, 1:671–680 (1989).

"Translation leader sequence" or "5' untranslated region" or "5'-UTR" all refer to a nucleotide sequence located between the promoter sequence of a gene and the coding sequence. The 5'-UTR is present in the fully processed mRNA upstream of the translation start sequence. The 5'-UTR may affect processing of the primary transcript to mRNA, mRNA stability, or translation efficiency. Examples of translation leader sequences have been described (Turner and Foster, *Molecular Biotechnology*, 3:225(1995)).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into polypeptide by the cell. "Sense RNA" refers to an RNA transcript that includes the mRNA and so can be translated into a polypeptide by the cell. "Antisense RNA" refers to an RNA transcript that is complementary to a target mRNA, resulting in specific RNA:RNA duplexes being formed by base pairing between the antisense RNA substrate and the target mRNA.

"Recombinant vector" refers to any agent by or in which a nucleic acid of interest is amplified, expressed, or stored, such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source and is capable of genomic integration or autonomous replication.

"Regulatory sequence" refers to a nucleotide sequence located upstream (5'), within, or downstream (3') with respect to a coding sequence. Additionally, introns may have regulatory activity. Transcription and expression of the coding sequence is typically impacted by the presence or absence of the regulatory sequence.

"Substantially homologous" refers to two sequences that are at least about 90% identical in sequence, as measured by the CLUSTAL W method in the Omiga program, using default parameters (Version 2.0; Accelrys, San Diego, Calif.).

"Substantially purified" refers to a molecule separated from substantially all other molecules normally associated with it in its native state. More preferably, a substantially purified molecule is the predominant species present in a preparation. A substantially purified molecule may be greater than about 60% free, preferably about 75% free, more preferably about 90% free, and most preferably about 95% free from the other molecules (exclusive of solvent) present in the natural mixture. The phrase "substantially purified" is not intended to encompass molecules present in their native state.

The term "transformation" refers to the introduction of nucleic acid into a recipient host. The term "host" refers to bacteria cells, fungi, animals or animal cells, plants or seeds, or any plant parts or tissues including plant cells, protoplasts, calli, roots, tubers, seeds, stems, leaves, seedlings, embryos, and pollen.

As used herein, a "transgenic plant" is a plant having stably introduced into its genome, for example, the nuclear or plastid genomes, a nucleic acid.

The terms "seeds" and "kernels" are understood to be equivalent in meaning. The term kernel is frequently used in describing the seed of a corn or rice plant. In all plants the seed is the mature ovule consisting of a seed coat, embryo, and in plants of the present invention, an endosperm.

HOI001 GBSS Nucleic Acids

The present invention provides nucleic acids that encode polypeptides substantially homologous to a granule bound starch synthase isolated from the inbred plant HOI001 (HOI001 GBSS). In one embodiment, these nucleic acid molecules are used in the context of the present invention for increasing the oil content of plant tissues. In one embodiment, the present invention provides an isolated nucleic acid that encodes a HOI001 GBSS protein, which nucleic acid is selected from the group consisting of SEQ ID NO: 1 and complements thereof, and nucleic acids which encode polypeptides having at least about 94% sequence identity with SEQ if NO: 3. The percent sequence identity of the polypeptides encoded by nucleic acids of this invention is preferably at least about 95%; and most preferably at least about 98%.

The present invention also provides vectors containing such HOI001 GBSS nucleic acids. As set forth in further detail hereinbelow, preferred nucleic acids include appropriate regulatory elements operably linked thereto that facilitate efficient expression of the inventive nucleic acids in a host, including without limitation bacterial, fungal, or plant hosts. Vectors useful in the context of the present invention can include such regulatory elements.

The nucleic acids and vectors encompassed by the present invention need not have the exact nucleic acid sequences described herein. Instead, the sequences of these nucleic acids and vectors can vary, so long as the nucleic acid either performs the function for which it is intended or has some other utility, for example, as a nucleic acid probe for complementary nucleic acids. For example, some sequence variability in any part of a HOI001 GBSS nucleic acid is permitted so long as transformation of a plant with the mutant or variant polypeptide or polypeptides result in a phenotype substantially similar to that of HOI001 GBSS. Most preferably, the aforementioned sequence variability results in increased oil accumulation in plant tissues, as compared to plants of the same or similar genotype, but without the transgene.

Fragment and variant nucleic acids of SEQ ID NO: 1, are also encompassed by the present invention. Nucleic acid fragments encompassed by the present invention are of three general types. First, fragment nucleic acids that are not full length but do perform their intended function are encompassed within the present invention. Second, fragments of nucleic acids identified herein that are useful as hybridization probes, are also included in the invention. And, third, fragments of nucleic acids identified herein can be used in suppression technologies known in the art, such as, for example, anti-sense technology or RNA inhibition (RNAi), which provides for reducing carbon flow in a plant into oil, making more carbon available for protein or starch accumulation, for example. Thus, fragments of a nucleotide sequence, such as SEQ ID NO: 1 may range from at least about 15 nucleotides, about 17 nucleotides, about 18 nucleotides, about 20 nucleotides, about 50 nucleotides, about 100 nucleotides or more. In general, a fragment nucleic acid of the present invention can have any upper size limit so long as it is related in sequence to the nucleic acids of the present invention but does not include the full length.

As used herein, "variants" have substantially similar or substantially homologous sequences when compared to reference or wild type sequence. For nucleotide sequences that encode proteins, variants also include those sequences that, because of the degeneracy of the genetic code, encode the identical amino acid sequence of the reference protein. Variant nucleic acids also include those that encode polypeptides that do not have amino acid sequences identical to that of the proteins identified herein, but which encode an active protein with conservative changes in the amino acid sequence.

The present invention is not limited to silent changes in the present nucleotide sequences but also includes variant nucleic acid sequences that conservatively alter the amino acid sequence of a polypeptide of the present invention. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode the peptides, without appreciable loss of their biological utility or activity.

According to the present invention, then, variant and reference nucleic acids of the present invention may differ in the encoded amino acid sequence by one or more substitutions, additions, insertions, deletions, fusions, and truncations, which may be present in any combination, so long as an active HOI001 GBSS protein is encoded by the variant nucleic acid. Such variant nucleic acids will not encode exactly the same amino acid sequence as the reference nucleic acid, but have conservative sequence changes. Codons capable of coding for such conservative amino acid substitutions are well known in the art.

Another approach to identifying conservative amino acid substitutions require analysis of the hydropathic index of amino acids may be considered. The importance of the hydropathic amino acid index in conferring interactive biological function on a protein is generally understood in the art (Kyte and Doolittle, J. Mol. Biol., 157:105–132 (1982)). It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, J. Mol. Biol., 157:105–132 (1982)); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those that are within ±1 are particularly preferred, and those within ±0.5 are even more particularly preferred.

Variant nucleic acids with silent and conservative changes can be defined and characterized by the degree of homology to the reference nucleic acid. Preferred variant nucleic acids are substantially homologous to the reference nucleic acids of the present invention. As recognized by one of skill in the art, such substantially similar nucleic acids can hybridize under stringent conditions with the reference nucleic acids identified by SEQ ID NO: 1, herein. These types of substantially homologous nucleic acids are encompassed by this invention.

Variant nucleic acids can be detected and isolated by standard hybridization procedures. Hybridization to detect or isolate such sequences is generally carried out under "moderately stringent" and preferably under "stringent" conditions. Moderately stringent hybridization conditions and associated moderately stringent and stringent hybridization wash conditions used in the context of nucleic acid hybridization experiments, such as Southern and northern hybridization, are sequence dependent, and are different under different environmental parameters. Longer sequences hybridize specifically at higher temperatures. An extensive guide to the hybridization of nucleic acids is found in Tijssen, Laboratory Techniques in Biochemistry and Molecular Biology-Hybridization with Nucleic Acid Probes, page 1, Chapter 2 "Overview of principles of hybridization and the strategy of nucleic acid probe assays" Elsevier, N.Y. (1993). See also, J. Sambrook et al., Molecular Cloning: A Laboratory Manual, Cold Spring Harbor Press, NY, pp 9.31–9.58 (1989); J. Sambrook et al., Molecular Cloning: A Laboratory Manual, Cold Spring Harbor Press, NY (3rd ed. 2001).

The present invention also provides methods for detection and isolation of derivative or variant nucleic acids encoding the proteins provided herein. The methods involve hybridizing at least a portion of a nucleic acid comprising any part of SEQ ID NO: 1 with respect to HOI001 GBSS-related sequences, to a sample nucleic acid, thereby forming a hybridization complex; and detecting the hybridization complex. The presence of the complex correlates with the presence of a derivative or variant nucleic acid that can be further characterized by nucleic acid sequencing, expression of RNA and/or protein and testing to determine whether the derivative or variant retains the ability to increase oil levels in plant tissue when transformed into that plant. In general, the portion of a nucleic acid comprising any part of SEQ ID NO: 1 used for hybridization is preferably at least about fifteen nucleotides, and hybridization is under hybridization conditions that are sufficiently stringent to permit detection and isolation of substantially homologous nucleic acids; preferably, the hybridization conditions are "moderately stringent", more preferably the hybridization conditions are "stringent", as defined herein and in the context of conventional molecular biological techniques well known in the art.

Generally, highly stringent hybridization and wash conditions are selected to be about 5° C. lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or the washing conditions, nucleic acids having 100% complementary can be identified and isolated.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide, in which case hybridization temperatures can be decreased. Dextran sulfate and/or Denhardt's solution (50×Denhardt's is 5% Ficoll, 5% polyvinylpyrrolidone, 5% BSA) can also be included in the hybridization reactions.

Exemplary low stringency conditions include hybridization with a buffer solution of 30 to 50% formamide, 5×SSC (20×SSC is 3M NaCl, 0.3 M trisodium citrate), 50 mM sodium phosphate, pH7, 5 mM EDTA, 0.1% SDS (sodium dodecyl sulfate), 5×Denhardt's with 100 μg/ml denatured salmon sperm DNA at 37° C., and a wash in 1× to 5×SSC (20×SSC defined as 3.0 M NaCl and 0.3 M trisodium citrate), 0.1% SDS at 37° C. Exemplary moderate stringency conditions include hybridization in 40 to 50% formamide, 5×SSC 50 mM sodium phosphate, pH 7, 5 mM EDTA, 0.1% SDS, 5×Denhardt's with 100 μg/ml denatured salmon sperm DNA at 42° C., and a wash in 0.1× to 2×SSC, 0.1% SDS at 42 to 55° C. Exemplary high stringency conditions include hybridization in 50% formamide, 5×SSC, 50 mM sodium phosphate, pH 7.0, 5 mM EDTA, 0.1% SDS, 5×Denhardt's with 100 μg/ml denatured salmon sperm DNA at 42° C., and a wash in 0.1×SSC, 0.1% SDS at 60 to 65° C.

In another embodiment of the present invention, the inventive nucleic acids are defined by the percent identity relationship between particular nucleic acids and other members of the class using analytic protocols well known in the art. Such analytic protocols include, but are not limited to: CLUSTAL in the PC/Gene program (available from Intelligenetics, Mountain View, Calif. or in the Omiga program version 2.0 Accelrys Inc., San Diego, Calif.); the ALIGN program (Version 2.0); and GAP, BESTFIT, BLAST, FASTA, and TFASTA in the Wisconsin Genetics Software Package, Version 8 (available from Genetics Computer Group (GCG), 575 Science Drive, Madison, Wis.). Alignments using these programs can be performed using the default parameters. The CLUSTAL program is well described by Higgins et al., *Gene*, 73:237–244 (1988); Higgins et al., *CABIOS*, 5:151–153 (1989); Corpet et al., *Nucleic Acids Res.*, 16:10881–10890 (1988); Huang et al., *CABIOS*, 8:155–165 (1992); and Pearson et al., *Meth. Mol. Biol.*, 24:307–331 (1994). The ALIGN program is based on the algorithm of Meyers and Miller, *Computer Applic. Biol. Sci.*, 4:11–17 (1988). The BLAST programs of Altschul et al., *J. Mol. Biol.*, 215:403 (1990), are based on the algorithm of Karlin and Altschul, *Proc. Natl. Acad. Sci. U.S.A.*, 87:2264–2268 (1990). To obtain gapped alignments for comparison purposes, Gapped BLAST (in BLAST 2.0) can be utilized as described in Altschul et al., *Nucleic Acids Res.*, 25:3389 (1997). Alternatively, PSI-BLAST (in BLAST 2.0) can be used to perform an iterated search that detects distant relationships between molecules. See, Altschul et al., supra. When utilizing BLAST, Gapped BLAST, PSI-BLAST, the default parameters of the respective programs (e.g., BLASTN for nucleotide sequences, BLASTP for proteins) can be used. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see, Henikoff & Henikoff, *Proc. Natl. Acad. Sci. U.S.A.*, 89:10915 (1989)) (see, http://www.ncbi.nlm.nih.gov/). Alignment may also be performed manually by inspection.

For purposes of the present invention, comparison of nucleotide sequences for determination of percent sequence identity to the nucleic acid sequences disclosed herein is preferably made using the BLASTN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Expression Vectors and Cassettes

The expression vectors and cassettes of the present invention include nucleic acids encoding HOI001 GBSS. A transgene comprising a HOI001 GBSS can be subcloned into an expression vector or cassette, and HOI001 GBSS expression can be detected and/or quantified. This method of screening is useful to identify transgenes providing for an expression of a HOI001 GBSS, and expression of a HOI001 GBSS in a transformed plant cell.

Plasmid vectors that provide for easy selection, amplification, and transformation of the transgene in prokaryotic and eukaryotic cells include, for example, pUC-derived vectors, pSK-derived vectors, pGEM-derived vectors, pSP-derived vectors, pBS-derived vectors, pFastBac (Invitrogen Corporation, Carlsbad, Calif.) for baculovirus expression and pYES2 (Invitrogen) for yeast expression. Additional elements may be present in such vectors, including origins of replication to provide for autonomous replication of the vector, selectable marker genes, preferably encoding antibiotic or herbicide resistance, unique multiple cloning sites providing for multiple sites to insert DNA sequences or genes encoded in the transgene, and sequences that enhance transformation of prokaryotic and eukaryotic cells. One vector that is useful for expression in both plant and prokaryotic cells is the binary Ti plasmid (as disclosed in Schilperoot et al., U.S. Pat. No. 4,940,838), as exemplified by vector pGA582. This binary Ti plasmid vector has been previously characterized by An, *Methods in Enzymology*, 153:292 (1987). This binary Ti vector can be replicated in prokaryotic bacteria, such as *E. coli* and *Agrobacterium*. The *Agrobacterium* plasmid vectors can also be used to transfer the transgene to plant cells. The binary Ti vectors preferably include the T DNA right and left borders to provide for efficient plant cell transformation, a selectable marker gene, unique multiple cloning sites in the T border regions, the colE1 replication of origin and a wide host range replicon. The binary Ti vectors carrying a transgene of the present invention can be used to transform both prokaryotic and eukaryotic cells, but is preferably used to transform plant cells, (see, Glassman et al., U.S. Pat. No. 5,258,300). Examples of plant expression vectors include the commercial vectors pBI101, pBI101.2, pBI101.3, and pBIN19 (Clontech, Palo Alto, Calif.).

In general, the expression vectors and cassettes of the present invention contain at least a promoter capable of expressing RNA in a plant cell and a terminator, in addition to a nucleic acid encoding a HOI001 GBSS. Other elements may also be present in the expression cassettes of the present invention. For example, expression cassettes can also contain enhancers, introns, untranslated leader sequences, cloning sites, matrix attachment regions for silencing the effects of chromosomal control elements, and other elements known to one of skill in the art.

Expression cassettes have promoters that can regulate gene expression. Promoter regions are typically found in the flanking DNA sequence upstream from coding regions in both prokaryotic and eukaryotic cells. A promoter sequence provides for regulation of transcription of the downstream gene sequence and typically includes from about 50 to about 2,000 nucleotide base pairs. Promoter sequences also contain regulatory sequences, such as enhancer sequences that can influence the level of gene expression. Some isolated promoter sequences can provide for gene expression of heterologous genes, that is, a gene different from the native or homologous gene. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous genes is advantageous because it provides for a sufficient level of gene expression to allow for easy detection and selection of transformed cells and provides for a high level of gene expression when desired. Transcription initiation regions that are preferentially expressed in seed tissue, and that are undetectable in other plant parts, are considered desirable for seed oil modifications in order to minimize any disruptive or adverse effects of the gene product.

Promoters of the present invention will generally include, but are not limited to, promoters that function in bacteria, plant cells, or plastids. Useful promoters for bacterial expression are the lacZ, T7, T5, or *E. coli* glg C promoters. Useful promoters for plant cells include wheat high molecular weight glutenin promoter (bp 2647–3895 of Genbank Accession X12928, version X12928.3, originally described in Anderson et al., *Nucleic Acids Res.*, 17:461–462 (1989)), the globulin promoter (see, Belanger and Kriz, *Genet.*, 129:863–872, (1991)), gamma zein Z27 promoter (see, U.S. Ser. No. 08/763,705; also, Lopes et al., *Mol Gen Genet.*, 247:603–613 (1995)), L3 oleosin promoter (U.S. Pat. No. 6,433,252), CaMV 35S promoter (Odell et al., *Nature*, 313:810 (1985)), the CaMV 19S (Lawton et al., *Plant Mol. Biol.*, 9:31F (1987)), nos (Ebert et al., *Proc. Natl. Acad. Sci. U.S.A.*, 84:5745 (1987)), Adh (Walker et al., *Proc. Natl. Acad. Sci. U.S.A.*, 84:6624 (1987)), sucrose synthase (Yang et al., *Proc. Natl. Acad. Sci. U.S.A.*, 87:4144 (1990)), tubulin, actin (Wang et al., *Mol. Cell. Biol.*, 12:3399 (1992)), cab (Sullivan et al., *Mol. Gen. Genet.*, 215:431 (1989)), PEP-Case promoter (Hudspeth et al., *Plant Mol. Biol.*, 12:579 (1989)), or those associated with the R gene complex (Chandler et al., *The Plant Cell*, 1:1175 (1989)).

Indeed in a preferred embodiment the promoter used is highly-expressed in the endosperm. Exemplary promoters include those from the zeins which are a group of storage proteins found in maize endosperm. Genomic clones for zein genes have been isolated (Pedersen et al., *Cell*, 29:1015–1026 (1982) and Russell et al., *Transgenic Res.*, 6(2):157–168 (1997)) and the promoters from these clones, including the 15 kD, 16 kD, 19 kD, 22 kD, and 27 kD genes (Z27, U.S. Ser. No. 08/763,705; also, Reina et al., *Nucl. Acids Res.*, 18:6426 (1990), Lopes et al., *Mol. Gen. Genet.*, 247:603–613 (1995)), can also be used. Other preferred promoters, known to function in maize, and in other plants, include the promoters for the following genes: WAXY (granule bound starch synthase; Shure et al., *Cell*, 35:225–233 (1983); Russell et al., *Transgenic Res.*, 6(2): 157–168 (1997)), Brittle 2 an Shrunken 2 (ADP glucose pryophosphorylase, Anderson et al., *Gene*, 97:199–205 (1991), Russell et al., *Transgenic Res.*, 6(2):157–168 (1997)), Shrunken 1(sucrose synthase, Yang and Russell, *Proc. Natl. Acad. Sci. U.S.A.*, 87:4144–4148 (1990)), branching enzymes I and II, WAXY promoter from rice (Terada et al., *Plant Cell Physiology*, 41(7):881–888 (2000)), debranching enzymes, glutelins (Zheng et al., *Plant J.*, 4:357–366 (1993), Russell et al., *Transgenic Res.*, 6(2): 157–168 (1997)), and Bet11 (basal endosperm transfer layer; Hueros et al., *Plant Physiol.*, 121:1143–1152 (1999)). Other promoters useful in the practice of the present invention that are known by one of skill in the art are also contemplated by the invention.

Moreover, transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924). As the DNA sequence between the transcription initiation site and the start of the coding sequence, i.e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, *Nucl. Acid Res.*, 15:6643 (1987)). The choice of such sequences is at the discretion of those of skill in the art. Sequences that are derived from genes that are highly expressed in higher plants, and in soybean, corn, and canola in particular, are contemplated.

Expression cassettes of the present invention will also include a sequence near the 3' end of the cassette that acts as a signal to terminate transcription from a heterologous nucleic acid and that directs polyadenylation of the resultant mRNA. These are commonly referred to as 3' untranslated regions or 3' UTRs. Some 3' elements that can act as transcription termination signals include the wheat HSP17 3' UTR (bp532–741 of GenBank X13431, version X13431.1, McElvain and Spiker, *Nucleic Acids Res.*, 17:1764 (1989)), those from the nopaline synthase gene of *Agrobacterium tumefaciens* (Bevan et al., *Nucl. Acid Res.*, 11:369 (1983)), a napin 3' UTR (Kridl et al., *Seed Sci Res.*, 1:209–219 (1991)), a globulin 3' UTR (Belanger and Kriz, *Genetics*, 129:863–872 (1991)), or one from a zein gene, such as Z27 (Lopes et al., *Mol Gen Genet.*, 247:603–613 (1995)). Other 3' elements known by one of skill in the art also can be used in the vectors of the present invention.

Regulatory elements, such as Adh intron 1 (Callis et al., *Genes Develop.*, 1:1183 (1987)), a rice actin intron (McElroy et al., *Mol. Gen. Genet.*, 231(1):150–160 (1991)), sucrose synthase intron (Vasil et al., *Plant Physiol.*, 91:5175 (1989)), the maize HSP70 intron (Rochester et al., *EMBO J.*, 5:451–458 (1986)), or TMV omega element (Gallie et al., *The Plant Cell*, 1:301 (1989)) may further be included where desired. These 3' nontranslated regulatory sequences can be obtained as described in An, *Methods in Enzymology*, 153: 292 (1987) or are already present in plasmids available from commercial sources, such as Clontech, Palo Alto, Calif. The 3' nontranslated regulatory sequences can be operably linked to the 3' terminus of any heterologous nucleic acid to be expressed by the expression cassettes contained within the present vectors. Other such regulatory elements useful in the practice of the present invention are known by one of skill in the art and can also be placed in the vectors of the invention.

The vectors of the present invention, as well as the coding regions claimed herein, can be optimized for expression in plants by having one or more codons replaced by other codons encoding the same amino acids so that the polypeptide is optimally translated by the translation machinery of the plant species in which the vector is used.

Selectable Markers

Selectable marker genes or reporter genes are also useful in the present invention. Such genes can impart a distinct phenotype to cells expressing the marker gene and thus allow such transformed cells to be distinguished from cells that do not have the marker. Selectable marker genes confer a trait that one can "select" for by chemical means, i.e., through the use of a selective agent (e.g., a herbicide, antibiotic, or the like). Reporter genes, or screenable genes, confer a trait that one can identify through observation or testing, i.e., by "screening" (e.g., the R-locus trait). Of course, many examples of suitable marker genes are known to the art and can be employed in the practice of the present invention.

A number of selectable marker genes are known in the art and can be used in the present invention. A preferred selectable marker gene for use in the present invention would include genes that confer resistance to herbicides like glyphosate, such as EPSP (Della-Cioppa et al., Bio/Technology, 5(6):579–84 (1987)). A particularly preferred selectable marker would include a gene that encodes an altered EPSP synthase protein (Hinchee et al., Biotech., 6:915 (1988)). Other possible selectable markers for use in connection with the present invention include, but are not limited to, a neo gene (Potrykus et al., Mol. Gen. Genet., 199:183 (1985)) which codes for kanamycin resistance and can be selected for by applying kanamycin, a kanamycin analog such as geneticin (Sigma Chemical Company, St. Louis, Mo.), and the like; a bar gene that codes for bialaphos resistance; a nitrilase gene, such as bxn from *Klebsiella ozaenae*, which confers resistance to bromoxynil (Stalker et al., Science, 242:419 (1988)); a mutant acetolactate synthase gene (ALS) that confers resistance to imidazolinone, sulfonylurea or other ALS-inhibiting chemicals (EP 154 204A1 (1985)); a methotrexate-resistant DHFR gene (Thillet et al., J. Biol. Chem., 263:12500 (1988)); a dalapon dehalogenase gene that confers resistance to the herbicide dalapon. Where a mutant EPSP synthase gene is employed, additional benefit may be realized through the incorporation of a suitable plastid transit peptide (CTP).

Screenable markers that may be employed include, but are not limited to, a β-glucuronidase or uidA gene (GUS), which encodes an enzyme for which various chromogenic substrates are known; an R-locus gene, which encodes a product that regulates the production of anthocyanin pigments (red color) in plant tissues (Dellaporta et al., In Chromosome Structure and Function, pp. 263–282 (1988)); a β-lactamase gene (Sutcliffe, Proc. Natl. Acad. Sci. U.S.A., 75:3737 (1978)), which encodes an enzyme for which various chromogenic substrates are known (e.g., PADAC, a chromogenic cephalosporin); a xylE gene (Zukowsky et al., Proc. Natl. Acad. Sci. U.S.A., 80:1101 (1983)) that encodes a catechol dioxygenase that can convert chromogenic catechols; an α-amylase gene (Ikuta et al., Biotech., 8:241 (1990)); a tyrosinase gene (Katz et al., J. Gen. Microbiol., 129:2703 (1983)) that encodes an enzyme capable of oxidizing tyrosine to DOPA and dopaquinone, which in turn condenses to form the easily detectable compound melanin; a β-galactosidase gene, which encodes an enzyme for which there are chromogenic substrates; a luciferase (lux) gene (Ow et al., Science, 234:856 (1986)), which allows for bioluminescence detection; or an aequorin gene (Prasher et al., Biochem. Biophys. Res. Comm., 126:1259 (1985)), which may be employed in calcium-sensitive bioluminescence detection, or a green fluorescent protein gene (Niedz et al., Plant Cell Reports, 14:403 (1995)). In a preferred embodiment, the screenable marker gene is operably linked to an aleurone-specific promoter as described by Kriz et al., in U.S. Pat. No. 6,307,123.

In addition to nuclear plant transformation, the present invention also extends to direct transformation of the plastid genome of plants. Hence, targeting of the gene product to an intracellular compartment within plant cells may also be achieved by direct delivery of a gene to the intracellular compartment. In some embodiments, direct transformation of plastid genome may provide additional benefits over nuclear transformation. For example, direct plastid transformation of HOI001 GBSS eliminates the requirement for a plastid targeting peptide and post-translational transport and processing of the pre-protein derived from the corresponding nuclear transformants. Plastid transformation of plants has been described by P. Maliga, Current Opinion in Plant Biology, 5:164–172 (2002), Heifetz, Biochimie, 82:655–666 (2000), Bock, J. Mol. Biol., 312:425–438 (2001), and Daniell et al., Trends in Plant Science, 7:84–91 (2002), and references cited therein.

After constructing a transgene containing an HOI001 GBSS, the expression vector or cassette can then be introduced into a plant cell. Depending on the type of plant cell, the level of gene expression, and the activity of the enzyme encoded by the gene, introduction of DNA encoding an HOI001 GBSS into the plant cell can lead to increased oil content in plant tissues.

Plant Transformation

Techniques for transforming a plant cell, a plant tissue, a plant organ, or a plant with a nucleic acid construct, such as a vector are known in the art. Such methods involve plant tissue culture techniques, for example. As used herein, "transforming" refers to the introduction of nucleic acid into a recipient host and the expression therein.

The plant cell, plant tissue, plant organ, or plant can be contacted with the vector by any suitable means as known in the art. Preferably, a transgenic plant expressing the desired protein is to be produced. Various methods for the introduction of a desired polynucleotide sequence encoding the desired protein into plant cells include, but are not limited to: (1) physical methods such as microinjection (Capecchi, Cell, 22(2):479–488 (1980)), electroporation (Fromm et al., Proc. Nat. Acad. Sci. U.S.A., 82(17):5824–5828 (1985); U.S. Pat. No. 5,384,253), and microprojectile bombardment mediated delivery (Christou et al., Bio/Technology, 9:957 (1991); Fynan et al., Proc. Nat. Acad. Sci. U.S.A., 90(24):11478–11482 (1993)); (2) virus mediated delivery methods (Clapp, Clin. Perinatol., 20(1):155–168 (1993); Lu et al., J. Exp. Med., 178(6):2089–2096 (1993); Eglitis Anderson, Biotechniques, 6(7):608–614 (1988); and (3) Agrobacterium-mediated transformation methods.

The most commonly used methods for transformation of plant cells are the *Agrobacterium*-mediated DNA transfer process (Fraley et al., Proc. Nat. Acad. Sci. U.S.A., 80:4803 (1983)) and the microprojectile bombardment mediated process. Typically, nuclear transformation is desired but where it is desirable to specifically transform plastids, such as chloroplasts or amyloplasts, plant plastids may be transformed utilizing a microprojectile bombardment mediated delivery of the desired polynucleotide for certain plant species such as tobacco, Arabidopsis, potato, and Brassica species.

*Agrobacterium*-mediated transformation is achieved through the use of a genetically engineered soil bacterium belonging to the genus *Agrobacterium*. Several *Agrobacterium* species mediate the transfer of a specific DNA known as "T-DNA," which can be genetically engineered to carry any desired piece of DNA into many plant species. The major events marking the process of T-DNA mediated pathogenesis are: induction of virulence genes, processing, and transfer of T-DNA. This process is the subject of many reviews (Ream, *Ann. Rev. Phytopathol.*, 27:583–618 (1989); Howard and Citovsky, *Bioassays*, 12:103–108 (1990); Kado, *Crit. Rev. Plant Sci.*, 10: 1–32 (1991); Zambryski, *Annual Rev. Plant Physiol. Plant Mol. Biol.*, 43:465–490 (1992); Gelvin, In Transgenic Plants, Kung and Wu, (eds.), Academic Press, San Diego, Calif., pp. 49–87 (1993); Binns and Howitz, In Bacterial Pathogenesis of Plants and Animals, Dang, (ed.). Berlin: Springer Verlag, pp. 119–138 (1994); Hooykaas and Beijersbergen, *Ann. Rev. Phytopathol.*, 32:157–179 (1994); Lessl and Lanka, *Cell*, 77:321–324 (1994); Zupan and Zambryski, *Annual Rev. Phytopathol.*, 27:583–618 (1995)).

*Agrobacterium*-mediated genetic transformation of plants involves several steps. The first step, in which the virulent *Agrobacterium* and plant cells are first brought into contact with each other, is generally called "inoculation." The *Agrobacterium* containing solution is then removed from contact with the explant by draining or aspiration. Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps. Both the "delay" and "selection" steps typically include bactericidal or bacteriostatic agents to kill any remaining *Agrobacterium* cells because the growth of *Agrobacterium* cells is undesirable after the infection (inoculation and co-culture) process.

A number of wild-type and disarmed strains of *Agrobacterium tumefaciens* and *Agrobacterium rhizogenes* harboring Ti or Ri plasmids can be used for gene transfer into plants. The *Agrobacterium* hosts contain disarmed Ti and Ri plasmids that do not contain the oncogenes that cause tumorigenesis or rhizogenesis, respectfully, which are used as the vectors and contain the genes of interest that are subsequently introduced into plants. Preferred strains would include but are not limited to *Agrobacterium tumefaciens* strain C58, a nopaline-type strain that is used to mediate the transfer of DNA into a plant cell, octopine-type strains such as LBA4404 or succinamopine-type strains, e.g., EHA101 or EHA105. The nucleic acid molecule, prepared as a DNA composition in vitro, is introduced into a suitable host such as *E. coli* and mated into the *Agrobacterium*, or directly transformed into competent *Agrobacterium*. These techniques are well-known to those of skill in the art.

The *Agrobacterium* can be prepared either by inoculating a liquid such as Luria Burtani (LB) media directly from a glycerol stock or streaking the *Agrobacterium* onto a solidified media from a glycerol stock, allowing the bacteria to grow under the appropriate selective conditions, generally from about 26° C.–30° C., or about 28° C., and taking a single colony or a small loop of *Agrobacterium* from the plate and inoculating a liquid culture medium containing the selective agents. Those of skill in the art are familiar with procedures for growth and suitable culture conditions for *Agrobacterium* as well as subsequent inoculation procedures. The density of the *Agrobacterium* culture used for inoculation and the ratio of *Agrobacterium* cells to explant can vary from one system to the next, and therefore optimization of these parameters for any transformation method is expected.

Typically, an *Agrobacterium* culture is inoculated from a streaked plate or glycerol stock and is grown overnight and the bacterial cells are washed and resuspended in a culture medium suitable for inoculation of the explant.

With respect to microprojectile bombardment (U.S. Pat. Nos. 5,550,318; 5,538,880; and 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the microprojectile stopping plate.

An illustrative embodiment of a method for delivering DNA into plant cells by microprojectile bombardment is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectile aggregates and may contribute to a higher frequency of transformation by reducing the damage inflicted on the recipient cells by projectiles that are too large.

For microprojectile bombardment, one will attach (i.e., "coat") DNA to the microprojectiles such that it is delivered to recipient cells in a form suitable for transformation thereof. In this respect, at least some of the transforming DNA must be available to the target cell for transformation to occur, while at the same time during delivery the DNA must be attached to the microprojectile. Therefore, availability of the transforming DNA from the microprojectile may comprise the physical reversal of bonds between transforming DNA and the microprojectile following delivery of the microprojectile to the target cell. This need not be the case, however, as availability to a target cell may occur as a result of breakage of unbound segments of DNA or of other molecules which comprise the physical attachment to the microprojectile. Availability may further occur as a result of breakage of bonds between the transforming DNA and other molecules, which are either directly or indirectly attached to the microprojectile. It further is contemplated that transformation of a target cell may occur by way of direct recombination between the transforming DNA and the genomic DNA of the recipient cell. Therefore, as used herein, a "coated" microprojectile will be one which is capable of being used to transform a target cell, in that the transforming DNA will be delivered to the target cell, yet will be accessible to the target cell such that transformation may occur.

Any technique for coating microprojectiles, which allows for delivery of transforming DNA to the target cells, may be used. Methods for coating microprojectiles, which have been demonstrated to work well with the present invention, have been specifically disclosed herein. DNA may be bound to microprojectile particles using alternative techniques, however. For example, particles may be coated with streptavidin and DNA end labeled with long chain thiol cleavable biotinylated nucleotide chains. The DNA adheres to the particles due to the streptavidin-biotin interaction, but is released in the cell by reduction of the thiol linkage through reducing agents present in the cell.

Alternatively, particles may be prepared by functionalizing the surface of a gold oxide particle, providing free amine groups. DNA, having a strong negative charge, binds to the functionalized particles. Furthermore, charged particles may be deposited in controlled arrays on the surface of mylar flyer disks used in the PDS-1000 Biolistics device, thereby facilitating controlled distribution of particles delivered to target tissue.

As disclosed above, it further is proposed, that the concentration of DNA used to coat microprojectiles may influence the recovery of transformants containing a single copy of the transgene. For example, a lower concentration of DNA may not necessarily change the efficiency of the transformation, but may instead increase the proportion of single copy insertion events. In this regard, approximately 1 ng to 2000 ng of transforming DNA may be used per each 1.8 mg of starting microprojectiles. In other embodiments of the present invention, approximately 2.5 ng to 1000 ng, 2.5 ng to 750 ng, 2.5 ng to 500 ng, 2.5 ng to 250 ng, 2.5 ng to 100 ng, or 2.5 ng to 50 ng of transforming DNA may be used per each 1.8 mg of starting microprojectiles.

Microprojectile bombardment techniques are widely applicable, and may be used to transform virtually any plant species. Examples of species that have been transformed by microprojectile bombardment include monocot species such as maize (PCT Publication WO 95/06128), barley, wheat (U.S. Pat. No. 5,563,055, specifically incorporated herein by reference in its entirety), rice, oat, rye, sugarcane, and sorghum; as well as a number of dicots including tobacco, soybean (U.S. Pat. No. 5,322,783, specifically incorporated herein by reference in its entirety), sunflower, peanut, cotton, tomato, and legumes in general (U.S. Pat. No. 5,563,055, specifically incorporated herein by reference in its entirety).

For microprojectile bombardment transformation in accordance with the present invention, both physical and biological parameters may be optimized. Physical factors are those that involve manipulating the DNA/microprojectile precipitate or those that affect the flight and velocity of either the macro- or microprojectiles. Biological factors include all steps involved in manipulation of cells before and immediately after bombardment, such as the osmotic adjustment of target cells to help alleviate the trauma associated with bombardment, the orientation of an immature embryo or other target tissue relative to the particle trajectory, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various bombardment parameters in small scale studies to fully optimize the conditions. One may particularly wish to adjust physical parameters such as DNA concentration, gap distance, flight distance, tissue distance, and helium pressure. It further is contemplated that the grade of helium may affect transformation efficiency. One also may optimize the trauma reduction factors (TRFs) by modifying conditions which influence the physiological state of the recipient cells and which may therefore influence transformation and integration efficiencies. For example, the osmotic state, tissue hydration, and the subculture stage or cell cycle of the recipient cells may be adjusted for optimum transformation.

Other methods of cell transformation can also be used and include but are not limited to introduction of DNA into plants by direct DNA transfer into pollen (Hess et al., *Intern Rev. Cytol.*, 107:367 (1987); Luo et al., *Plant Mol. Biol. Reporter*, 6:165 (1988)), by direct injection of DNA into reproductive organs of a plant (Pena et al., *Nature*, 325:274 (1987)), or by direct injection of DNA into the cells of immature embryos followed by the rehydration of desiccated embryos (Neuhaus et al., *Theor. Appl. Genet.*, 75:30 (1987)).

The regeneration, development, and cultivation of plants from single plant protoplast transformants or from various transformed explants is well known in the art (Weissbach and Weissbach, In: *Methods for Plant Molecular Biology*, Academic Press, San Diego, Calif., (1988)). This regeneration and growth process typically includes the steps of selection of transformed cells, culturing those individualized cells through the usual stages of embryonic development through the rooted plantlet stage. The resulting transgenic rooted shoots are thereafter planted in an appropriate plant growth medium such as soil.

The development or regeneration of plants containing the exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature*, 335:454–457 (1988); Marcotte et al., *Plant Cell*, 1:523–532 (1989); McCarty et al., *Cell*, 66:895–905 (1991); Hattori et al., *Genes Dev.*, 6:609–618 (1992); Goff et al., *EMBO J.*, 9:2517–2522 (1990)). Transient expression systems may be used to functionally dissect gene constructs (see generally, Maliga et al., *Methods in Plant Molecular Biology*, Cold Spring Harbor Press (1995)).

Any of the nucleic acid molecules of the present invention may be introduced into a plant cell in a permanent or transient manner in combination with other genetic elements such as vectors, promoters, enhancers, etc. Further, any of the nucleic acid molecules of the present invention may be introduced into a plant cell in a manner that allows for expression or overexpression of the protein or fragment thereof encoded by the nucleic acid molecule.

Transgenic plants may find use in the commercial manufacture of proteins or other molecules, such as oils, where the molecules of interest are extracted or purified from plant parts, seeds, and the like. Cells or tissue from the plants may also be cultured, grown in vitro, or fermented to manufacture such molecules.

Improvements encoded by the recombinant DNA may be transferred, e.g., from cells of one species to cells of other species, e.g., by protoplast fusion. The transgenic plants may also be used in commercial breeding programs, or may be crossed or bred to plants of related crop species. For example, a nucleic acid of the present invention, operably linked to a promoter, can be introduced into a particular plant variety by crossing, without the need for ever directly transforming a plant of that given variety. Therefore the present invention not only encompasses a plant directly regenerated from cells that have been transformed in accordance with the present invention, but also the progeny of such plants.

The present invention also provides for a method of stably expressing an HOI001 GBSS of interest in a plant, which includes, contacting the plant cell with a vector of the present invention that has a nucleic acid encoding the HOI001 GBSS of interest, under conditions effective to transfer and integrate the vector into the nuclear genome of the cell. A promoter within the expression cassette can be any of the promoters provided herein, for example, a constitutive promoter, an inducible promoter, a tissue-specific promoter, or a seed specific promoter. Such promoters can provide expression of an encoded HOI001 GBSS at a desired time, or at a desired developmental stage, or in a desired tissue. The vector can also include a selectable marker gene. When using the vector with *Agrobacterium tumefaciens*, the vector can have an *Agrobacterium tumefaciens* origin of replication.

Plants

Plants for use with the vectors of the present invention preferably include monocots, especially oil producing species, most preferably corn (*Zea mays*). Other species contemplated by the present invention include alfalfa (*Medicago sativa*), rice (*Oryza sativa*), barley (*Hordeum vulgare*), millet (*Panicum miliaceum*), rye (*Secale cereale*), wheat (*Triticum aestivum*), and sorghum (*Sorghum bicolor*).

Any of the plants or parts thereof of the present invention may be processed to produce a feed, meal, protein, or oil preparation. A particularly preferred plant part for this purpose is a seed. Methods to produce feed, meal, protein, and oil preparations are known in the art. See, for example, U.S. Pat. Nos. 4,957,748; 5,100,679; 5,219,596; 5,936,069; 6,005,076; 6,146,669; and 6,156,227.

Characterization of Transformed Plants

To confirm the presence of the transgene in the regenerated plant, a variety of techniques, which are well known in the art, are available. Examples of these techniques include but are not limited to: (a) molecular assays of DNA integration or RNA expression such as Southern or northern blotting, TAQMAN® technology (Applied Biosystems, Foster City, Calif.) and PCR; (b) biochemical assays detecting the presence of the protein product such as ELISA, western blotting, or by enzymatic function; or (c) chemical analysis of the targeted plant part, such as seed tissue, for qualitative and quantitative determination of oil, protein, or starch.

The following examples are provided to illustrate the present invention and are not intended to limit the invention in any way.

EXAMPLE 1

This example describes the isolation and sequencing of the HOI001 GBSS gene from corn line HOI001. HOI001 is an inbred plant derived from MGSC 915E (Maize Genetic Stock Center, Urbana, Ill.), and is more fully described in U.S. Patent Publication Nos. 20030172416 and 20030154524, both of which are incorporated herein by reference.

Genomic DNA was extracted from corn germ tissue from HOI001, 22 days after pollination, using the following procedure. Between 50–100 mg dissected germ tissue was placed in a Bio101 Multimix tube (Qiagen, Carlsbad, Calif., Cat. No. 657-601) with extraction buffer and glass beads. The extraction buffer consisted of 100 mM Tris-HCl (pH 8.0), 50 mM EDTA, 100 mM NaCl, 5 mM DTT, and 1% SDS. The tissue was then disrupted using the Bio 101 FASTPREP® machine (Qiagen) with 3 pulses of 20 seconds each. Following a 15 minute incubation at 65° C., 330 µl of 5M potassium acetate was added to each tube. The tubes were then incubated at 0° C. for 20 minutes to precipitate the SDS, followed by centrifugation at 12,000 rpm (Eppendorf Model 54172) for 10 minutes. The supernatant was transferred to a new tube and 100 µl of 5M ammonium acetate (pH 7.0) and 700 µl of isopropanol was added to precipitate the DNA. The tubes were mixed by inversion and centrifuged at 14,000 rpm for 10 minutes. After discarding the supernatant, the pellet was resuspended in 500 µof 70% ethanol and recovered by centrifugation at 14,000 rpm for 5 minutes. The recovered pellet containing the DNA was resuspended in 50 µl of TE buffer and stored at 4° C.

The HOI001 GBSS gene was isolated from the extracted genomic DNA using PCR methodology that was adapted from Advantage GC (BD Biosciences Clontech, Palo Alto, Calif.). The following primers were designed based on the published sequence of *Zea mays* GBSS from Shure et al., *Cell*, 35(1):225–233 (1983) [SEQ ID NO: 2]:

5' primer (Primer number 14543)
5'-TCAGCCGTTCGTGTGGCAAGATTCATCTGTTGT [SEQ ID NO: 5]
CTC-3'

3' primer (Primer number 14547)
5'-TCAGCGGGATTATTTACTCCACCACTACAGGTC [SEQ ID NO: 6]
CATTT-3'.

The following PCR reaction was assembled for a total volume of 50 µl;

| | |
|---|---|
| 37 µl | PCR grade water |
| 5 µl | 5X Advantage GC PCR buffer |
| 1 µl | 50X dNTP Mix (10 mM each) |
| 1 µl | 50X Advantage GC Polymerase Mix |
| 2.5 µl | primer 14543 |
| 2.5 µl | primer 14547 |
| 1 µl | genomic DNA |

The cycle parameters were: 95° C. for 1 minute, 35 cycles of 95° C. for 30 seconds and 68° C. for 3 minutes.

The PCR products were separated by electrophoresis in agarose and a 4.7 kB fragment containing the gene of interest was observed. Five microliters of the original PCR reaction was utilized as template for additional amplification using the same primers and conditions described above. The 4.7 kB amplification products from independent amplification reactions were isolated by agarose gel electrophoresis, cloned into the PCR 2.1 cloning vector using the TOPO TA cloning kit (Invitrogen), then transformed into an *E. coli* host. Plasmid DNA was prepared from cultures grown from each colony, and then the inserts from 3 separate plasmid preparations were sequenced. Alignment of these sequences generated a consensus sequence highly homologous but not identical to the published GBSS gene, although no specific insert sequence was equivalent to the consensus. One clone (designated pCGN9480-2) had an insert sequence with the fewest sequence changes relative to the consensus. A clone containing the consensus was then generated by restriction enzyme-mediated excision of non-consensus sequence and religation with fragments containing the consensus sequence, obtained by digestion of the other clones or by PCR amplification from HOI001 genomic DNA. The consensus sequence, including 1.5 kB upstream of the transcription start site and approximately 300 base pairs downstream of the stop codon, is listed as SEQ ID NO: 1.

Figure 5:
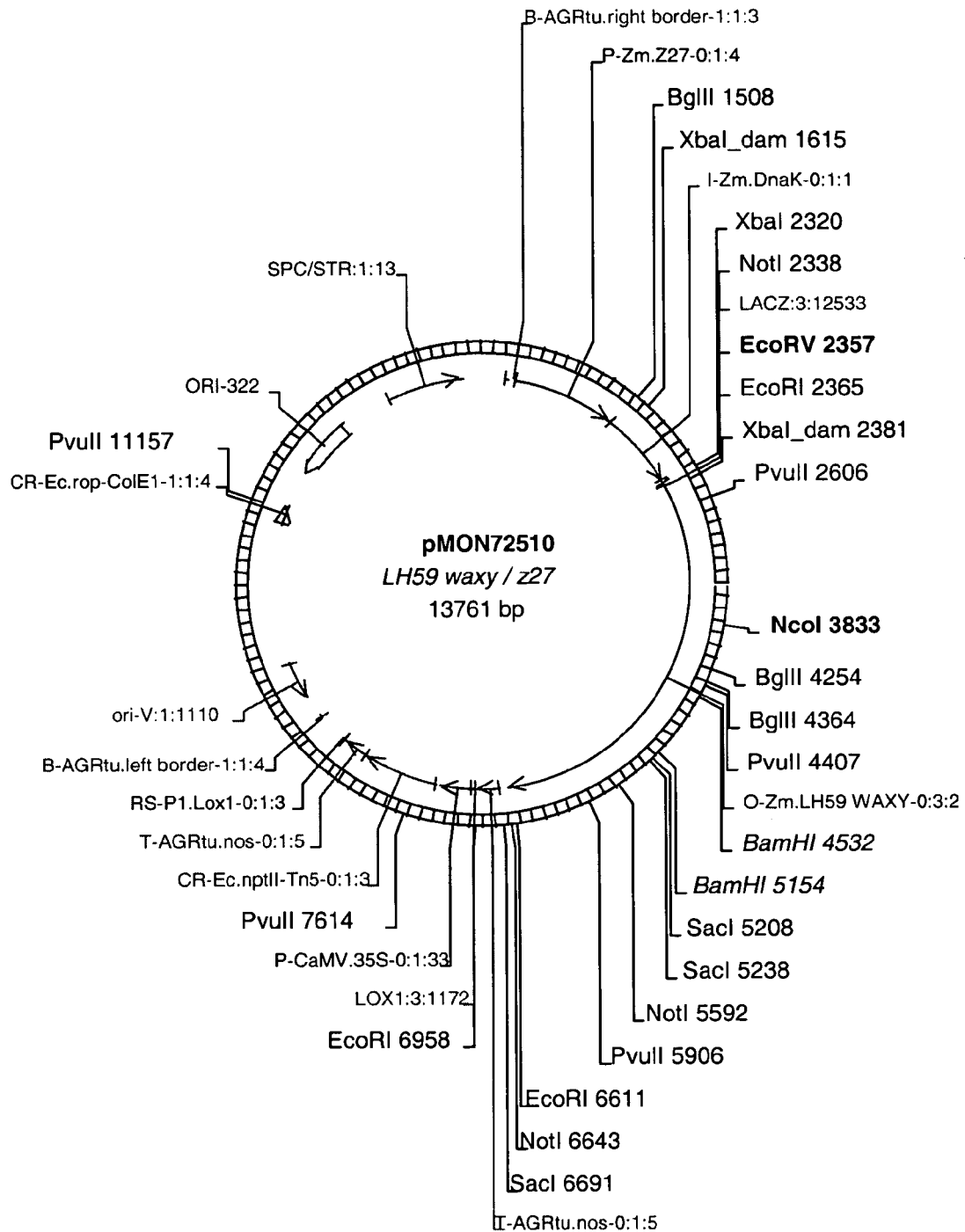
FIG. 5 depicts a plasmid map of pMON72510.
Figure 6A:
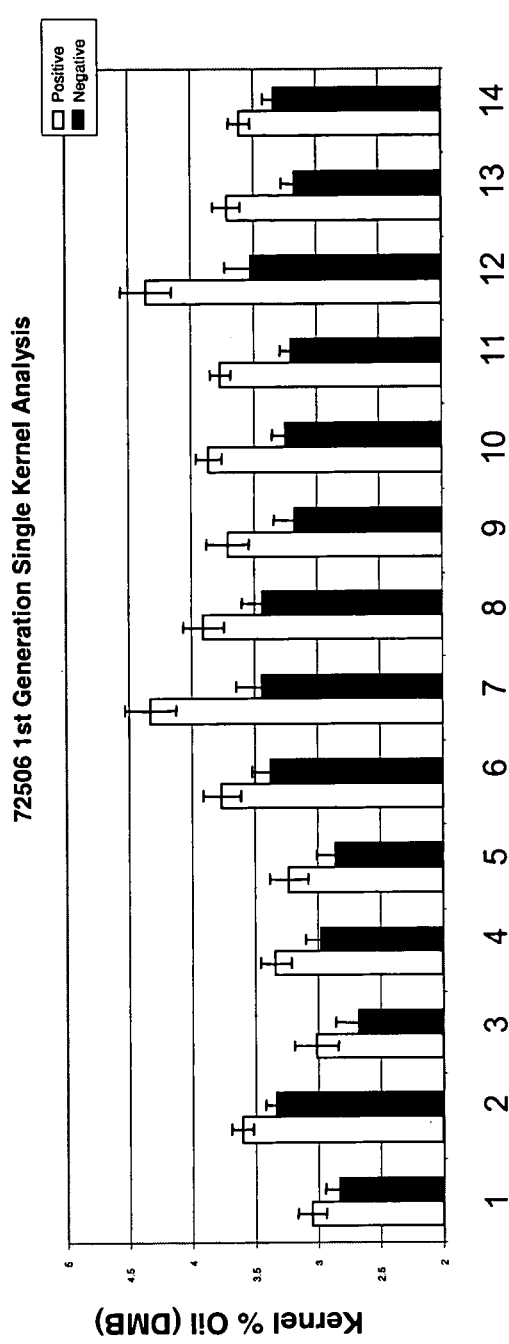
FIGS. 6A and 6B graphically depict the difference in oil levels from kernels of plants transformed with pMON72506 containing the GBSS from HOI001 (SEQ ID NO: 1, 6A) and pMON72510 containing the GBSS from LH59 (SEQ ID NO: 8, 6B). Gene positive and gene negative kernels are compared from each event. Only events with statistically significant changes in oil (14 of 29) are shown in 6A.
Figure 6B:
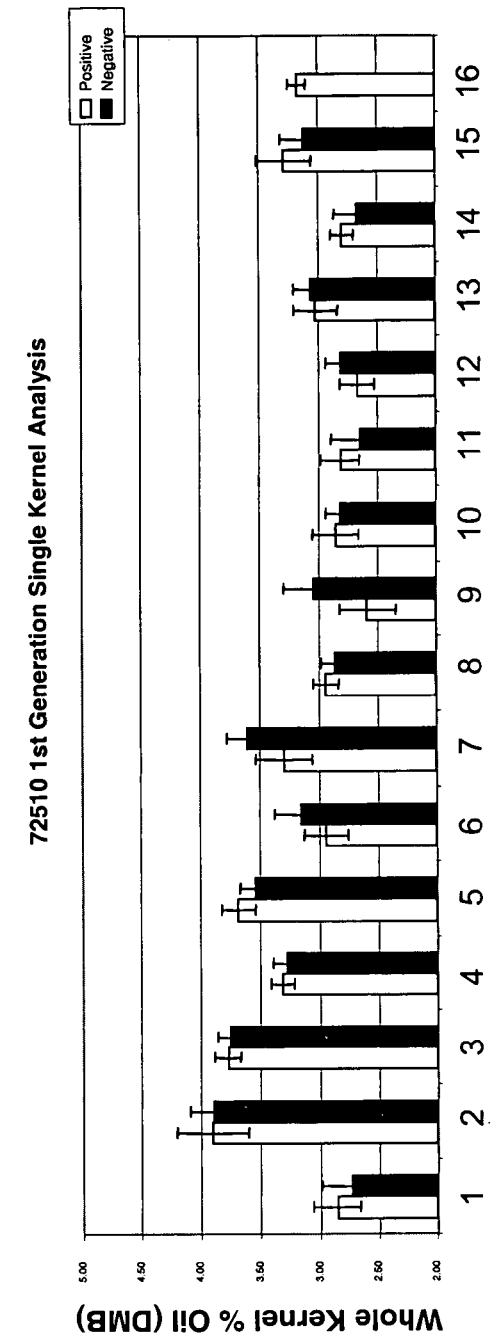

The GBSS gene from elite corn inbred line LH59 [SEQ ID NO: 7] was isolated using the procedures and primers described above, and cloned into the binary vector pMON68203. The resulting plasmid containing the LH59 GBSS is named pMON72510 (FIG. 5).

FIG. 1 shows the nucleic acid sequence alignment of the HOI001 GBSS [SEQ ID NO: 1] compared to the published sequence of Shure et al., supra [SEQ ID NO: 2] and the GBSS from LH59 [SEQ ID NO: 7], using the Omiga software package 2.0, (Accelrys Inc., San Diego, Calif.). The alignment shows there are the following polymorphisms unique to the HOI001 GBSS sequence, that is not found in either the LH59 GBSS sequence or the published sequence of Shure et al., supra:

1. Single nucleotide polymorphisms:
    a. T>C at position 158
    b. G>A at position 337
    c. C>A at position 343
    d. C>A at position 349
    e. G>A at position 441
    f. C>T at position 666
    g. G>C at position 777
    h. T>A at position 878
    i. C>T at position 980
    j. T>A at position 1210
    k. C>T at position 1216
    l. A>T at position 1450
    m. T>C at position 1709
    n. A>G at position 1720
    o. T>A at position 1721
    p. G>C at position 1722
    q. C>T at position 1761
    r. G>A at position 1836
    s. C>T at position 1852
    t. G>A at position 1953
    u. C>T at position 2043
    v. C>T at position 2109
    w. C>G at position 2110
    x. G>C at position 2115
    y. A>T at position 2448
    z. C>T at position 2454
    aa. T>G at position 2609
    bb. A>G at position 2929
    cc. G>T at position 2933
    dd. C>T at position 2946
    ee. G>T at position 3875
    ff. T>A at position 4008
    gg. T>C at position 4018
    hh. T>G at position 4023
    ii. C>A at position 4025
    jj. C>T at position 4169
    kk. A>T at position 4225
    ll. C>A at position 4562
2. Insertions:
    a. Sequence g at position 632
    b. Sequence atgc at position 1185–1189
    c. Sequence tgcaccagcagc at position 1456–1467
    d. Sequence atgca at position 1746–1750
    e. Sequence catcaca at position 1868–1874
    f. Sequence ct at position 2100–2101
    g. Sequence ccat at position 2488–2491
    h. Sequence tat at position 3810–3812
3. Deletions:
    a. Sequence cgt at position 288–290
    b. Sequence aa at position 704–705
    c. Sequence c at position 882
    d. Sequence atccg at position 1139–1143
    e. Sequence ctctctg at position 1256–1262
    f. Sequence tc at position 1714–1715
    g. Sequence tgcaactgcaaatgca at position 1917–1932
    h. Sequence g or a at position 3790
    i. Sequence cgagccaggggt(t or c)gaaggcgaggagatcgcgc-cgctcgccaagg agaacgtggccgcgccctgaagagttcggcct at position 4393–4467

FIG. 2 shows the alignment of the corresponding predicted amino acid sequences from the GBSS gene isolated from HOI001 [SEQ ID NO: 3], and the GBSS gene described in Shure et al., supra [SEQ ID NO: 4], respectively. The results indicate that there is a sequence of additional amino acid residues on the carboxy terminus of the HOI001 GBSS starting at approximately position 1441 and an area of non-alignment in the region of amino acid residue 55–60.

FIG. 3 shows the alignment of the corresponding predicted amino acid sequences from the *Zea mays* GBSS gene isolated from inbred LH59 [SEQ ID NO: 8], and the *Zea mays* granule bound starch synthase gene described in Shure et al., supra, respectively. The results indicate that there is a sequence of additional amino acid residues on the carboxy terminus of the HOI001 GBSS starting at approximately position 1441 and an area of non-alignment in the region of amino acid residue 55–60.

EXAMPLE 2

This example sets forth the construction of plant transformation vectors containing the sequences of the HOI001 GBSS and the GBSS from inbred line LH59, [SEQ ID NOs: 1 and 7, respectively].

Figure 4:
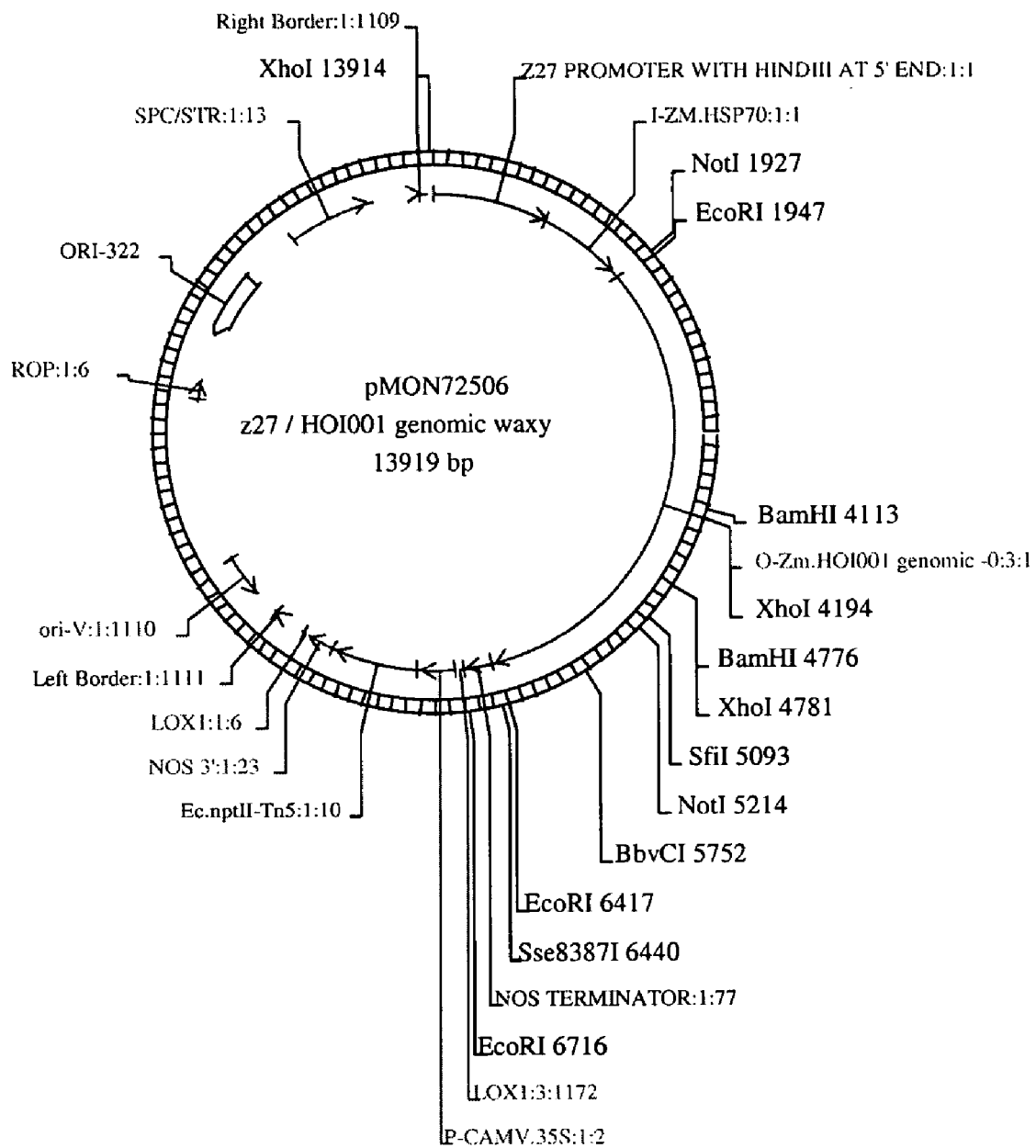
FIG. 4 depicts a plasmid map of pMON72506.

The HOI001 GBSS sequence was cut from the consensus-corrected version of pMON9480-2 using the restriction enzyme EcoR1. The resulting 4.7 kb fragment was purified following the manufacturer's protocol for the Qiagen miniprep kit (Qiagen, Inc., Valencia, Calif.). The ends of the fragment were blunted following manufacturer's protocol in the Stratagene PCR polishing kit (Stratagene, Inc., La Jolla, Calif.). The fragment was then gel purified using the Qiagen Gel Extraction kit (Qiagen), and cloned into pMON68203, a binary vector for plant transformation. The binary vector, pMON68203, contains left and right borders for T-DNA transfer, a CaMV 35S promoter::nptII::nos 3' UTR plant selectable marker element (described in U.S. Pat. No. 6,255,560), and plant expression cassette sequences which include a 1.1 kb Z27 promoter (bp 19–1117 of Accession #S78780, Lopes et al., *Mol. Gen. Genet.*, 247(5):603–613 (1995)) for endosperm expression, a corn hsp70 intron (base pairs 4–153 of the maize gene for heat shock 70 exon 2, Accession #X03679, Rochester et al., *EMBO J.*, 5:451–458 (1986)), and a nos 3' UTR, (base pairs 2924–2671 of the *Agrobacterim tumefaciens* strain C58 Ti plasmid, Accession #AE009420, Wood et al., *Science*, 294:2317–2323 (2001)). The binary vector pMON68203 was digested with Stu1, dephosphorylated by incubating with shrimp alkaline phosphatase (Roche Applied Science, Indianapolis, Ind.) at 37° C. for 60 minutes and ligated with the 4.7 kb gel purified fragment of the HOI001 GBSS, described above. The resulting plasmid was named pMON72506 (FIG. 4).

The GBSS from corn line LH59, [SEQ ID NO: 7], was similarly cloned into the binary vector pMON68203, to form pMON72510.

EXAMPLE 3

This example describes the transformation of corn with the HOI001 GBSS and the GBSS from corn line LH59, using the vectors described in Example 2.

The transformation vectors pMON72506 and pMON72510 were used to transform maize plants using the following procedure.

Corn plants are grown in a greenhouse under standard practices. Controlled pollinations were made. The ears of the plants are harvested when the resulting hybrid embryos were 1.5 to 2.0 mm in length, usually 10–15 days after pollination. After removing the husks, the kernels on the ears were surface-sterilized by spraying with or soaking in 80% ethanol.

The *Agrobacterium* strain ABI, and an *Agrobacterium tumefaciens* binary vector system were used for the transformations. Plasmids pMON72506 and pMON72510 were transformed into *Agrobacterium tumefaciens* according to methods well known in the art. Prior to inoculation of corn cells the *Agrobacterium* cells are grown overnight at room temperature in AB medium (Chilton et al., *Proc. Nat. Acad. Sci. U.S.A.*, 71:3672–3676 (1974)) comprising appropriate antibiotics for plasmid maintenance and 200 µM acetosyringone. Immediately prior to inoculation the *Agrobacterium* cells were pelleted by centrifugation, and resuspended in either CRN122 medium (2.2 g/L MS (Murashige and Skoog, *Physiol. Plant*, 15:473–497 (1962)) basal salts, 2 mg/L glycine, 0.5 mg/L niacin, 0.5 g/l L-pyridoxine-HCl, 0.1 g/L thiamine, 115 mg/L L-proline, 36 g/L glucose, and 68.5 g/L sucrose, pH 5.4) or CRN347 medium (CRN122 medium except with 0.44 g/L MS salts, 10 g/L glucose, 20 g/L sucrose, and 100 mg/L ascorbic acid) containing 200 µM acetosyringone and 20 µM AgNO$_3$.

The immature maize embryos were excised from individual kernels, immersed in an *Agrobacterium* suspension, and incubated at room temperature for 5–15 minutes. The *Agrobacterium* solution is then removed, and the inoculated immature embryos were transferred scutellum-side up from inoculation CRN122 medium to co-cultivation CRN123 medium (CRN122 medium except with 0.5 mg/L additional thiamine-HCl, 20 g/L sucrose, 10 g/L glucose and 3 mg/L 2,4 D) containing 200 µM acetosyringone and 20 µM silver nitrate and incubated at 23° C. for 1 day. Alternatively, excised embryos were cultured for 8–11 days in 211V medium (3.98 g/L Chu N6 salts (Chu, C. C., The N6 medium and its application to anther culture of cereal crops, in *Plant Tissue Culture Plant Tissue Culture. Proceedings of the Peking Symposium*, Boston, Mass. (1981), 43–50), 0.5 mg/L thiamine HCl, 0.5 mg/L nicotinic acid; 1.0 mg/L 2,4 D, 20 g/L sucrose, 0.69 g/L L-proline, 0.91 g/L L-asparagine monohydrate, 1.6 g/L MgCl$_2$ hexahydrate, 0.1 g/L casein hydrolysate, 0.5 g/L MES, 0.1 g/L myo-inositol, and 16.9 mg/L silver nitrate, pH 5.8 solidified with 2 g/L Gelgro) and calli were inoculated with *Agrobacterium* CRN347 medium suspensions at 23° C. for 3 days without adding additional media.

The embryos were then transferred to CRN220 selection medium (4.4 g/L MS salts, 1.3 mg/L nicotinic acid, 0.25 mg/L pyridoxine HCl, 0.25 mg/L thiamine HCl, 0.25 mg/L calcium pantothenate, 30 g/L sucrose, 12 mM proline, 0.05 g/L casamino acids, 500 mg/L carbenicillin, 200 mg/L paromomycin, 2.2 mg/L picloram, 0.5 mg/L 2,4 D and 3.4 mg/L silver nitrate, pH 5.6 solidified with 7 g/L Phytagar), or calli are transferred to CRN344 selection medium (3.98 g/L Chu N6 salts, 1.0 mg/L thiamine HCl, 0.5 mg/L nicotinic acid; 1.0 mg/L 2,4 D, 20 g/L sucrose, 0.69 g/L L-proline, 0.91 g/L L-asparagine monohydrate, 1.6 g/L MgCl$_2$ hexahydrate, 0.1 g/L casein hydrolysate, 0.5 g/L MES, 0.1 g/L myo-inositol, 500 mg/L carbenicillin, 200 mg/L paromomycin and 16.9 mg/L silver nitrate, pH 5.8 solidified with 6 g/L Phytagar). After 2–3 weeks at 27° C. in the dark, surviving tissues were transferred to the same selection medium and cultured for up to an additional 2 weeks or transferred to regeneration medium as described below.

Plant regeneration is achieved by transferring the putative transgenic callus from CRN220 to CRN232 medium (CRN220 medium lacking picloram, 2,4-D, and silver nitrate, and containing 3.52 mg/L benzylaminopurine (BAP) and 250 mg/L carbenicillin) or from CRN344 medium to 217A medium (211RTTV lacking silver nitrate, 2,4 D, and paromomycin and containing 3.52 mg/L BAP and 250 mg/L carbenicillin) and incubating for 5–7 days at 27° C. Tissue is then transferred from CRN232 medium to CRN264 medium (4.4 g/L MS salts, 1.3 g/L nicotinic acid, 0.25 mg/L pyridoxine HCl, 0.25 mg/L thiamine HCl, 0.25 mg/L calcium pantothenate, 10 g/L glucose, 20 g/L maltose, 1 mM L-asparagine, 0.1 g/L myo-inositol, 250 mg/L carbenicillin and 100 mg/L paromomycin, pH 5.8 solidified with 6 g/L Phytagar) or from 217A medium to CRN346 medium (4.4 g/L MS salts, MS vitamins, 60 g/L sucrose, 0.05 g/L myo-inositol, 250 mg/L carbenicillin, 75 mg/L paromomycin, pH 5.8 solidified with 6 g/L KOH) in Phytatrays, and incubated in the light at 28° C. until shoots with well-developed roots were produced (typically 2–3 weeks). These developing plantlets were then transferred to soil, hardened off in a growth chamber at 27° C., 80% humidity, and low light intensity for approximately 1 week, and then transferred to a greenhouse and the R0 plants were grown under standard greenhouse conditions. The R0 plants were reciprocally crossed and both immature/developing kernels and mature kernels were collected from each of the resulting plants for subsequent analyses. The results of the analyses are described below in Example 6.

These developing plantlets were then transferred to soil, hardened off in a growth chamber at 27° C., 80% humidity, and low light intensity for approximately 1 week, and then transferred to a greenhouse. The R0 plants were then grown under standard greenhouse conditions. Fertile R0 plants were crossed to a non-transgenic recurrent inbred, with the R0 plant serving as either the female or male (or occasionally both) in the cross. Both developing and mature F1 kernels were collected and analyzed, from each of the resulting ears as described in Example 4. The results of the analyses are reported below in Example 5.

EXAMPLE 4

This example provides the analytical procedures to determine oil, protein, and starch levels in kernels from transgenic plants containing the HOI001 GBSS gene or the LH59 GBSS gene.

Oil Content Analysis: Oil levels (on a mass basis and as a percent of tissue weight) of first generation single corn kernels and dissected germ and endosperm are determined by low-resolution $^1$H nuclear magnetic resonance (NMR) (Tiwari et al., *JAOCS*, 51:104–109 (1974); or Rubel, *JAOCS*, 71:1057–1062 (1994)), whereby NMR relaxation times of single kernel samples are measured, and oil levels are calculated based on regression analysis using a standard curve generated from analysis of corn kernels with varying oil levels as determined gravimetrically following accelerated solvent extraction.

To compare oil analyses of transgenic and non-transgenic kernels, the presence or absence of the transgene is determined by detection (or lack thereof) of a transgene-specific 517 bp PCR product, using a sequence within the Hsp70 intron as a 5' primer, and a sequence within the HOI001 GBSS gene as a 3' primer:

```
5' primer (primer number 19056):
5'-ATCTTGCTCGATGCCTTCTC-3',       [SEQ ID NO: 16]

3' primer (primer number 18986):
5'-GCCTTCGCTTGTCGTGGGT-3'.        [SEQ ID NO: 17]
```

Oil levels in advanced generation seed are determined by NIT spectroscopy, whereby NIT spectra of pooled seed samples harvested from individual plants are measured, and oil levels are calculated based on regression analysis using a standard curve generated from analysis of corn kernels with varying oil levels, as determined gravimetrically following accelerated solvent extraction or elemental (% N) analysis, respectively.

One-way analysis of variance and the Student's T-test are performed to identify significant differences in oil (% kernel weight) between seed from marker positive and marker negative plants.

Alternatively, oil levels of pooled kernels from single ears are determined by low-resolution $^1$H nuclear magnetic resonance (NMR) (Tiwari et al., *JAOCS*, 51:104–109 (1974); or Rubel, *JAOCS*, 71:1057–1062 (1994)), whereby NMR relaxation times of pools of kernels are measured, and oil levels are calculated based on regression analysis using a standard curve generated from analysis of corn kernels with varying oil levels as determined gravimetrically following accelerated solvent extraction.

Protein Analyses: For kernel protein analysis, small bulk samples consisting of 50–100 kernels for each treatment are measured using near infrared reflectance spectroscopy (InfraTec model 1221, Teccator, Hogannas Sweden). This procedure is based upon the observation that a linear relation exists between the absorption of near infrared radiation and the quantity of chemical constituents comprised in a typical grain sample. Prior to analyzing unknown samples, spectral data is collected with calibration samples that are subsequently analyzed using a nitrogen combustion analysis technique (Murray, I., and P. C. Williams, 1987, Chemical Principles of Near-infrared Technology, In Near-Infrared Technology in the Agricultural and Food Industries, P. Williams and K. Norris eds.). A multivariate model is developed using the spectral data from the spectrometer and the primary data. In the present case a PLS-1 (Partial Least Squares Regression Type I) multivariate model is constructed using 152 calibration samples. Each unknown sample is scanned on the spectrometer at least 5 times and its protein content predicted with each scan. Each time the sample is scanned it is added back to the sample cuvette to minimize multiplicative scattering effects, which are not correlated to chemical property of interest. The predicted starch is averaged for the multiple scans and then reported for each sample.

Starch analyses: For kernel starch analysis, small bulk samples consisting of 50–100 kernels for each treatment are measured using near infrared reflectance spectroscopy (InfraTec model 1221, Teccator, Hogannas Sweden). This procedure is based upon the observation that a linear relation exists between the absorption of near infrared radiation and the quantity of chemical constituents comprised in a typical grain sample. Prior to analyzing unknown samples, spectral data is collected with calibration samples that are subsequently analyzed using standard wet chemistry analytical techniques (Murray, I., and P. C. Williams, 1987, Chemical Principles of Near-infrared Technology, In Near-Infrared Technology in the Agricultural and Food Industries, P. Williams and K. Norris eds.). A multivariate model is developed using the spectral data from the spectrometer and the primary data. Each unknown sample is scanned on the spectrometer at least 5 times and its starch content predicted with each scan. Each time the sample is scanned it is added back to the sample cuvette to minimize multiplicative scattering effects, which are not correlated to chemical property of interest. The predicted starch is averaged for the multiple scans and then reported for each sample.

EXAMPLE 5

This example describes the analysis of kernels from plants transformed with the HOI001 GBSS and the GBSS from LH59.

Kernels from a total of 54 transgenic events expressing the HOI001 GBSS transgenic allele were analyzed using the procedures set forth in Example 4. Table 1 shows whole kernel oil levels of transgenic (positive) and nontransgenic (negative) F1 kernels from ears of 20 transgenic events analyzed by the single kernel NMR procedure described in Example 4. Only results from events with a statistically significant increase in oil ($p<0.05$) are shown.

The results demonstrate that transgenic kernels from ears of 20 of the 54 events had statistically significant increases in whole kernel oil content (% dry weight) relative to nontransgenic kernels on the same ear. No events had a statistically significant decrease in oil.

TABLE 1

| Pedigree | Positive | | Negative | | | |
| --- | --- | --- | --- | --- | --- | --- |
| | n | Mean | n | Mean | Delta | Prob > F |
| ZM_S67336/LH172 | 12 | 4.22 | 12 | 3.19 | 1.03 | 0.0000 |
| ZM_S66829/LH172 | 8 | 4.33 | 16 | 3.44 | 0.89 | 0.0013 |
| ZM_S67359/LH172 | 12 | 4.36 | 12 | 3.52 | 0.84 | 0.0003 |
| ZM_S71593/LH172 | 14 | 3.09 | 10 | 2.40 | 0.69 | 0.0258 |
| ZM_S67345/LH172 | 8 | 3.31 | 15 | 2.67 | 0.64 | 0.0199 |
| ZM_S67335/LH172 | 9 | 3.85 | 15 | 3.25 | 0.61 | 0.0000 |
| ZM_S71577/LH172 | 4 | 3.50 | 20 | 2.92 | 0.59 | 0.0298 |
| ZM_S66804/LH172 | 10 | 3.50 | 14 | 2.94 | 0.56 | 0.0017 |
| ZM_S67348/LH172 | 6 | 3.76 | 16 | 3.20 | 0.56 | 0.0000 |
| ZM_S67351/LH172 | 11 | 3.73 | 13 | 3.19 | 0.54 | 0.0173 |
| ZM_S69437/LH172 | 9 | 3.70 | 15 | 3.16 | 0.54 | 0.0002 |
| ZM_S67331/LH172 | 13 | 3.70 | 11 | 3.17 | 0.53 | 0.0026 |

TABLE 1-continued

| Pedigree | Positive n | Positive Mean | Negative n | Negative Mean | Delta | Prob > F |
|---|---|---|---|---|---|---|
| ZM_S67330/LH172 | 12 | 3.90 | 12 | 3.43 | 0.47 | 0.0071 |
| LH172/ZM_S71581 | 17 | 3.47 | 7 | 3.07 | 0.40 | 0.0004 |
| ZM_S66805/LH172 | 11 | 3.76 | 13 | 3.37 | 0.39 | 0.0151 |
| LH172/ZM_S69443 | 11 | 3.23 | 13 | 2.86 | 0.37 | 0.0243 |
| LH172/ZM_S67360 | 11 | 3.34 | 13 | 2.98 | 0.36 | 0.0080 |
| LH172/ZM_S67338 | 17 | 3.01 | 7 | 2.68 | 0.34 | 0.0287 |
| ZM_S71569/LH172 | 11 | 2.99 | 12 | 2.74 | 0.25 | 0.0354 |
| LH172/ZM_S66817 | 14 | 3.05 | 9 | 2.83 | 0.22 | 0.0391 |

Transgenic kernels from R0 plants pollinated by non-transgenic inbred pollen (for example, pedigree ZM_S67336/LH172, positive) had both a higher frequency of a significant oil increase (15/29 plants analyzed) and a higher average significant oil increase (0.61%) relative to kernels from non-transgenic inbred plants pollinated by transgenic pollen (for example, pedigree LH172/ZM_S66817, negative) from an R0 male parent (5/37 plants analyzed, 0.34% significant oil increase). These results suggest that the greater transgene dosage found in the endosperm of kernels from the R0 plants, due to maternal inheritance effects, may result in a greater increase in oil.

Similarly, kernels from a total of 15 transgenic events containing the LH59 GBSS transgenic allele were analyzed. None of the kernels from ears of any of the events had statistically significant increases in whole kernel oil content (% dry weight) relative to nontransgenic kernels on the same ear, indicating that the increase in oil was unique to the HOI001 GBSS allele.

EXAMPLE 6

This example describes the increase in oil levels obtained in transgenic F2 kernels from field-grown plants.

To ascertain the impact of the HOI001 GBSS gene on kernel oil levels of field-grown plants, 24–48 segregating F1 seed from each of 40 events were planted in a field nursery. Developing plants were screened for the presence of the transgenic cassette by a non-lethal kanamycin resistance assay, whereby an antibiotic solution (0.1% (w/v) kanamycin and 0.1% (w/v) paromomycin) is applied to the leaf surface and scored for the presence (nontransgenic) or absence (transgenic) of necrotic lesions 1 week after antibiotic application. Kernels were isolated from the ears of both transgenic plants and non-transgenic plants, and then were assayed for kernel oil, protein, and starch by Near-Infrared Transmittance Spectroscopy.

Table 2 shows the mean whole kernel oil levels and the increase in whole kernel oil levels (Delta) in ears from plants containing (positive) and lacking (negative) the transgenic cassette containing the selectable marker and the HOI001 GBSS gene. Oil levels were determined by the NIT procedure described in Example 4, and only events with a statistically significant increase in oil (p<0.05) are shown.

TABLE 2

| Event | Positive n | Positive Mean | Negative n | Negative Mean | Delta | Prob > F |
|---|---|---|---|---|---|---|
| ZM_S67359 | 8 | 4.76 | 7 | 3.83 | 0.93 | <.0001 |
| ZM_S71546 | 5 | 5.42 | 3 | 4.50 | 0.92 | 0.0012 |

TABLE 2-continued

| Event | Positive n | Positive Mean | Negative n | Negative Mean | Delta | Prob > F |
|---|---|---|---|---|---|---|
| ZM_S67354 | 2 | 4.85 | 13 | 4.02 | 0.83 | <.0001 |
| ZM_S66817 | 3 | 4.37 | 1 | 3.70 | 0.67 | 0.0099 |
| ZM_S71577 | 3 | 4.60 | 8 | 3.95 | 0.65 | <.0001 |
| ZM_S67343 | 5 | 4.42 | 4 | 3.78 | 0.65 | 0.0142 |
| ZM_S71555 | 5 | 5.10 | 3 | 4.47 | 0.63 | 0.0343 |
| ZM_S71551 | 9 | 4.69 | 6 | 4.07 | 0.62 | 0.041 |
| ZM_S69437 | 3 | 4.57 | 8 | 3.95 | 0.62 | 0.0002 |
| ZM_S66804 | 7 | 5.04 | 7 | 4.44 | 0.60 | 0.0016 |
| ZM_S67338 | 7 | 4.30 | 6 | 3.73 | 0.57 | 0.0068 |
| ZM_S71573 | 3 | 4.87 | 3 | 4.40 | 0.47 | 0.0405 |
| ZM_S67331 | 4 | 4.35 | 12 | 3.92 | 0.43 | 0.0025 |
| ZM_S71594 | 2 | 4.35 | 8 | 3.95 | 0.40 | 0.0037 |
| ZM_S67340 | 12 | 4.04 | 11 | 3.72 | 0.32 | 0.0115 |
| ZM_S66800 | 1 | 4.30 | 8 | 3.95 | 0.30 | 0.0398 |

The results show whole kernel oil level was increased in transgenic ears relative to nontransgenic ears (p<0.05) in 16 out of 36 events analyzed.

Table 3 shows the mean kernel starch levels (%) and the change in kernel starch levels in ears from plants containing (positive) and lacking (negative) the transgenic cassette containing the selectable marker and the HOI001 GBSS gene. Only events with a statistically significant increase in oil (p<0.05) are shown.

Table 4 shows mean kernel protein levels (%) and the change in kernel protein levels in ears from plants containing (positive) and lacking (negative) the transgenic cassette containing the selectable marker and the HOI001 GBSS gene. Only events with a statistically significant increase in oil (p<0.05) are shown.

Based on NIT analysis, starch levels in events with increases in oil were lowered slightly (Table 3), and protein levels were mostly unchanged (Table 4).

TABLE 3

| Event | Positive n | Positive Mean | Negative n | Negative Mean | Delta | Prob > F |
|---|---|---|---|---|---|---|
| ZM_S67359 | 8 | 69.15 | 7 | 70.94 | −1.79 | 0.0004 |
| ZM_S71546 | 5 | 70.10 | 3 | 71.33 | −1.23 | 0.0451 |
| ZM_S67354 | 2 | 69.50 | 13 | 71.12 | −1.62 | 0.0024 |
| ZM_S66817 | 3 | 69.73 | 1 | 70.00 | −0.27 | 0.5286 |
| ZM_S71577 | 3 | 71.47 | 8 | 71.40 | 0.07 | 0.8702 |
| ZM_S67343 | 5 | 69.92 | 4 | 71.20 | −1.28 | 0.0187 |
| ZM_S71555 | 5 | 70.30 | 3 | 71.23 | −0.93 | 0.118 |
| ZM_S71551 | 9 | 70.49 | 6 | 71.23 | −0.74 | 0.117 |
| ZM_S69437 | 3 | 69.77 | 8 | 71.40 | −1.63 | 0.0018 |
| ZM_S66804 | 7 | 71.19 | 7 | 72.27 | −1.09 | 0.0073 |
| ZM_S67338 | 7 | 69.81 | 6 | 71.25 | −1.44 | 0.0009 |
| ZM_S71573 | 3 | 69.77 | 3 | 70.67 | −0.90 | 0.1352 |
| ZM_S67331 | 4 | 70.10 | 12 | 71.23 | −1.13 | 0.0026 |
| ZM_S71594 | 2 | 70.75 | 8 | 71.40 | −0.65 | 0.1906 |
| ZM_S67340 | 12 | 70.82 | 11 | 71.35 | −0.53 | 0.0257 |
| ZM_S66800 | 1 | 70.50 | 8 | 71.40 | −0.90 | 0.16 |

TABLE 4

| Event | Positive n | Positive Mean | Negative n | Negative Mean | Delta | Prob > F |
|---|---|---|---|---|---|---|
| ZM_S67359 | 8 | 11.84 | 7 | 11.29 | 0.55 | 0.2942 |
| ZM_S71546 | 5 | 12.86 | 3 | 12.30 | 0.56 | 0.1775 |
| ZM_S67354 | 2 | 12.55 | 13 | 12.07 | 0.48 | 0.2885 |
| ZM_S66817 | 3 | 12.70 | 1 | 14.40 | −1.70 | 0.1336 |

TABLE 4-continued

| Event | Positive | | Negative | | Delta | Prob > F |
|---|---|---|---|---|---|---|
| | n | Mean | n | Mean | | |
| ZM_S71577 | 3 | 9.50 | 8 | 12.03 | −2.53 | 0.0005 |
| ZM_S67343 | 5 | 11.46 | 4 | 11.40 | 0.06 | 0.929 |
| ZM_S71555 | 5 | 12.58 | 3 | 12.43 | 0.15 | 0.6995 |
| ZM_S71551 | 9 | 12.23 | 6 | 11.97 | 0.27 | 0.4938 |
| ZM_S69437 | 3 | 11.80 | 8 | 12.03 | −0.23 | 0.7384 |
| ZM_S66804 | 7 | 12.14 | 7 | 11.07 | 1.07 | 0.0304 |
| ZM_S67338 | 7 | 12.26 | 6 | 11.87 | 0.39 | 0.452 |
| ZM_S71573 | 3 | 11.37 | 3 | 11.30 | 0.07 | 0.8416 |
| ZM_S67331 | 4 | 12.18 | 12 | 12.23 | −0.05 | 0.9133 |
| ZM_S71594 | 2 | 11.80 | 8 | 12.03 | −0.23 | 0.6682 |
| ZM_S67340 | 12 | 11.44 | 11 | 11.28 | 0.16 | 0.578 |
| ZM_S66800 | 1 | 11.40 | 8 | 12.03 | −0.63 | 0.412 |

EXAMPLE 7

This example describes the increase in oil levels obtained in transgenic F2 hybrid kernels from field-grown plants.

To ascertain the impact of the HOI001 GBSS gene on kernel oil levels of hybrid field-grown plants, 24–48 segregating F1 seed from each of 14 events, having sufficient seed, were planted in a field nursery. Developing plants were screened for the presence of the transgenic cassette by the non-lethal Kanamycin resistance assay, described above in Example 6. Pollen from transgenic plants was used to pollinate the stiff-stalk inbred LH244. The segregating F1 transgenic seed generated was then planted and the resultant plants were screened for the presence of the transgene by the non-lethal Kanamycin resistance assay. F2 hybrid kernels were isolated from ears from transgenic plants and non-transgenic plants, and assayed for kernel oil by Nuclear Magnetic Resonance Spectroscopy, as described in Example 4.

Table 5 shows mean whole kernel oil levels and the increase (Delta) in whole kernel oil levels in ears from hybrid plants containing (positive) and lacking (negative) the transgenic cassette containing the selectable marker and the HOI001 GBSS gene. Oil levels were determined by the bulk set NMR procedure described in Example 4, and only events with a statistically significant increase in oil (p<0.05) are shown. The data indicate that whole kernel oil level was increased in transgenic ears relative to nontransgenic ears (p<0.05) in 9 out of 14 events analyzed.

TABLE 5

| Event | Positive | | Negative | | Delta | Prob > F |
|---|---|---|---|---|---|---|
| | n | Mean | n | Mean | | |
| ZM_S67354 | 6 | 4.43 | 1 | 3.00 | 1.43 | 0.0431 |
| ZM_S67346 | 9 | 3.90 | 8 | 3.13 | 0.78 | 0.0003 |
| ZM_S71546 | 9 | 4.24 | 5 | 3.58 | 0.66 | 0.0016 |
| ZM_S71556 | 10 | 4.12 | 4 | 3.48 | 0.65 | 0.0044 |
| ZM_S71577 | 8 | 3.94 | 6 | 3.30 | 0.64 | 0.0047 |
| ZM_S71594 | 10 | 3.91 | 7 | 3.30 | 0.61 | 0.0041 |
| ZM_S71573 | 10 | 4.02 | 6 | 3.42 | 0.60 | 0.0001 |
| ZM_S67343 | 10 | 3.72 | 4 | 3.15 | 0.57 | 0.0009 |
| ZM_S67331 | 8 | 3.80 | 3 | 3.40 | 0.40 | 0.0281 |

EXAMPLE 8

This example describes the elevation of GBSS activity in corn endosperm tissue expressing the HOI001 GBSS gene.

Developing ears from F1 plants screened for the presence of the transgenic cassette by the non-lethal Kanamycin resistance assay were harvested and immediately frozen at 24 days post pollination. Segregating F2 kernels were removed from the ear, then dissected into germ and endosperm fractions. Individual dissected kernels were identified as transgenic or nontransgenic by screening for the ability to PCR-amplify a portion of the transgenic cassette from genomic DNA isolated from individual germs using transgene-specific primers, as described in Example 4. For each of six events, approximately 10 endosperms from the corresponding transgenic and nontransgenic kernels were pooled separately.

Each endosperm pool was ground to a fine powder with a mortar and pestle under liquid nitrogen, and starch granules were isolated in triplicate according to the procedure of Shure et al., *Cell*, 35(1):225–233 (1983). Granule-bound starch synthase activity was assayed on the isolated granules using the method of Vos-Scheperkeuter et al., *Plant Physiol.*, 82:411–416(1986).

Table 6 shows the granule-bound starch synthase activity (pmol/min/mg starch) in developing F2 endosperm containing or lacking the HOI001 GBSS transgenic cassette. Values shown are means and standard errors of triplicate assays. The data indicates that starch granules from transgenic kernels generally had elevated GBSS activity, indicating that the effect of the HOI001 allele on oil levels is not a function of reducing overall GBSS activity, but functions by the addition of an activity uniquely encoded by the HOI001 GBSS gene.

TABLE 6

| Event | Transgenic | | Non-transgenic | | p > F |
|---|---|---|---|---|---|
| | Mean | SE | mean | SE | |
| S67338 | 585 | 41 | 455 | 15 | 0.0392 |
| S67359 | 583 | 20 | 521 | 15 | 0.0665 |
| S71546 | 635 | 16 | 540 | 23 | 0.0281 |
| S66804 | 587 | 50 | 454 | 20 | 0.0702 |
| S71551 | 588 | 9 | 574 | 11 | 0.3712 |
| S71555 | 486 | 24 | 464 | 12 | 0.4641 |

EXAMPLE 9

This example describes the isolation and sequencing of the coding region of the GBSS cDNA from corn line HOI001.

mRNA was extracted from developing corn endosperm tissue from HOI001, 22 days after pollination, using a procedure adapted from Opsahl-Ferstad et al., *Plant J.*, 12(10):235–246 (1997). Briefly, developing endosperm from 3 separate kernels was pooled, frozen in liquid nitrogen, and then pulverized with a mortar and pestle. Approximately 50 mg frozen powdered endosperm was extracted with 0.5 mL buffer (0.5 M LiCl, 10 mM EDTA, 5 mM dithiothreitol, 100 mM Tris-HCl, pH 8.0, 1% (w/v) SDS). This aqueous extract was then extracted with phenol:chloroform:isoamyl alcohol (25:24:21), and the organic fraction was discarded. Nucleic acids were precipitated from the aqueous fraction by addition of an equal volume of isopropyl alcohol followed by centrifugation. The resulting supernatant was discarded. The pellet containing the mRNA was washed twice with 70% ethanol, dried, and then resuspended in 50 μL water containing 0.1% (v/v) diethylpyrocarbonate.

First-strand cDNA was synthesized from the isolated RNA using the Clontech SMART™ cDNA synthesis system (BD Biosciences). This first-strand cDNA was used as template to amplify HOI001 GBSS cDNA sequences using primers containing an EcoRV restriction site followed by 18 bp of the predicted translational start site (5' primer) and a Sse83871 restriction site followed by 17 bp of the predicted 3' end up to the translation stop site (3' primer):

```
5' Primer (primer number 20095):
5'-GGATATCACCATGGCGGCTCTGGCCACG-      [SEQ ID NO: 9]
3', 3' Primer (primer number 20092):
5'-GTCCTGCAGGCTACACATACTTGTCCA-3'.    [SEQ ID NO: 10]
```

The resulting 1.8 kB amplification products from independent amplification reactions were isolated by agarose gel electrophoresis, cloned independently into the PCR 2.1 cloning vector using the TOPO TA cloning kit (Invitrogen), and then transformed into an *E. coli* host. Multiple colonies were isolated from each transformation, plasmid DNA was prepared from cultures grown from each colony, and then the insert in each plasmid preparation was sequenced. Alignment of these sequences generated a consensus sequence containing an open reading frame equivalent to that predicted to be encoded by the HOI001 GBSS gene, although no specific insert sequence was equivalent to the consensus. One clone (designated 7345705-10) had an insert sequence with single base pair deletion relative to the consensus. This clone was used to generate a plasmid (designated pMON81463) containing the consensus sequence by inserting the additional nucleotide using the Quick-Change mutagenesis kit (Stratagene). This sequence, representing the coding region of the HOI001 GBSS cDNA, is listed in SEQ ID NO: 11.

EXAMPLE 10

This example sets forth the construction of plant transformation vectors containing the HOI001 GBSS cDNA coding region [SEQ ID NO: 11], designed to obtain different levels, timing and spatial patterns of expression, and the subsequent transformation of corn.

Figure 7:
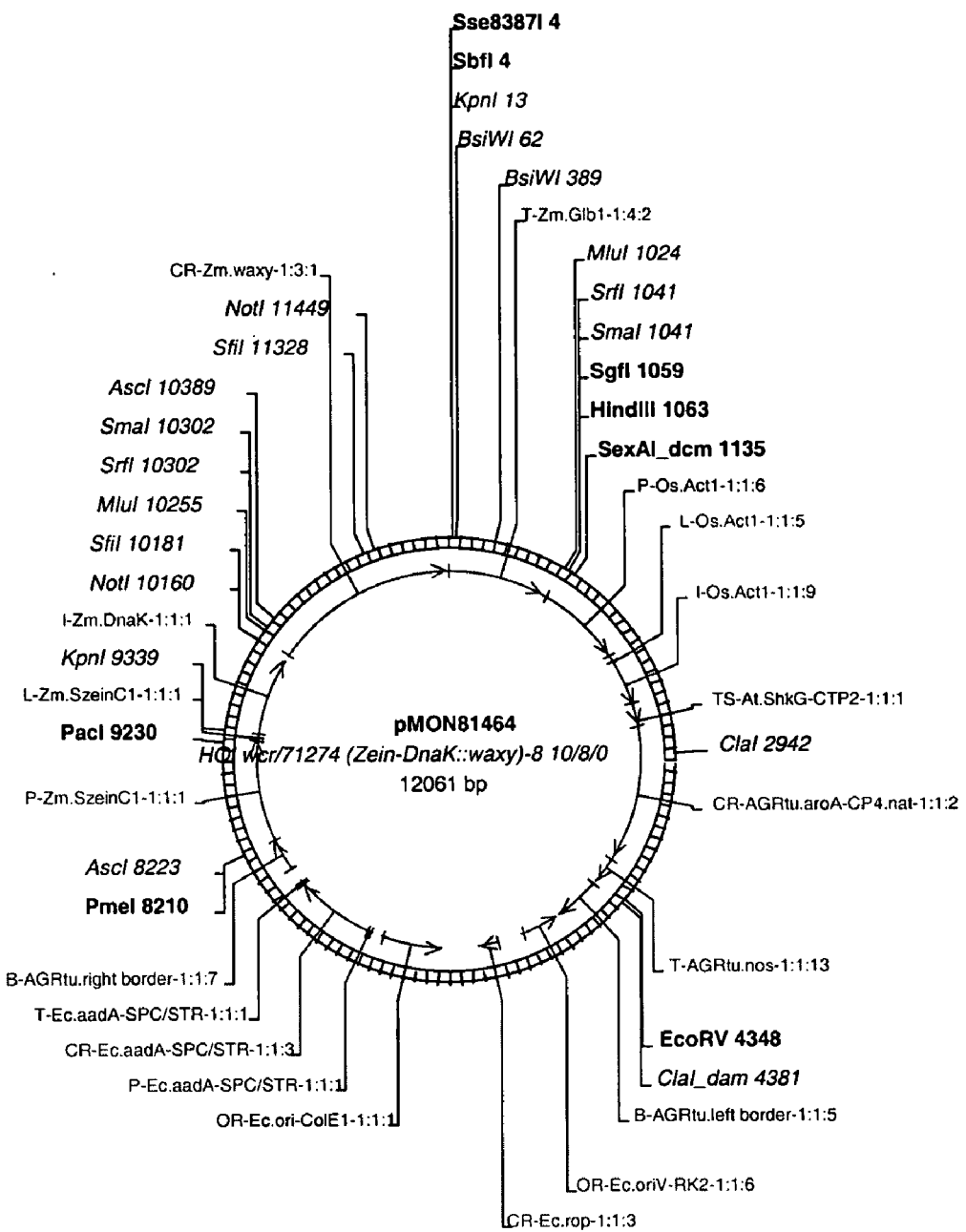
FIG. 7 depicts a plasmid map of pMON81464.

A plant transformation vector containing the HOI001 GBSS coding region driven by a Z27 promoter was constructed. The HOI001 GBSS coding region was isolated from pMON81463 by restriction digest with EcoRV and Sse83871, and cloned into the binary vector pMON71274. This binary vector contains left and right borders for T DNA transfer; a rice Actin promoter::rice Actin intron::CP4::nos 3' UTR, plant selectable marker element; and plant expression cassette sequences which include a 1.1 kb Z27 promoter (bp 19–1117 of Genbank Accession #S78780, Lopes et al., *Mol. Gen. Genet.*, 247(5):603613 (1995)) for endosperm expression; a corn hsp70 intron (base pairs 4–153 of the maize gene for heat shock 70 exon 2, Genbank Accession #X03679, Rochester et al., *EMBO J.*, 5:451–458 (1986)), and a globulin 3' UTR. The resulting plasmid was named pMON81464 (FIG. 7).

A second plant expression binary vector containing the wheat high molecular weight glutenin promoter (bp 2647–3895 of Genbank Accession X12928, version X12928.3, originally described in Anderson et al., *Nucleic Acids Res.*, 17:461–462 (1989)) and the corn hsp70 intron, fused to the GBSS coding region, fused to the wheat HSP17n3' UTR (bp532–741 of Gen Bank Accession X13431, version X13431.1, McElvain and Spiker, *Nucleic Acids Res.*, 17:1764 (1989)), was constructed. A sequence containing the wheat high molecular weight glutenin promoter fused to the corn hsp70 intron was amplified from an intermediary vector using 5' and 3' primers containing AscI and NotI restriction sites, respectively:

```
5' Primer (primer number 21084):
5'-GGCGCGCCGTCGACGGTATCGATAAGCTTG     [SEQ ID NO: 12]
C-3', 3' Primer (primer number 21085):
5'-GCGGCCGCCCGCTTGGTATCTGCATTACAA     [SEQ ID NO: 13]
TG-3'.
```

Figure 8:
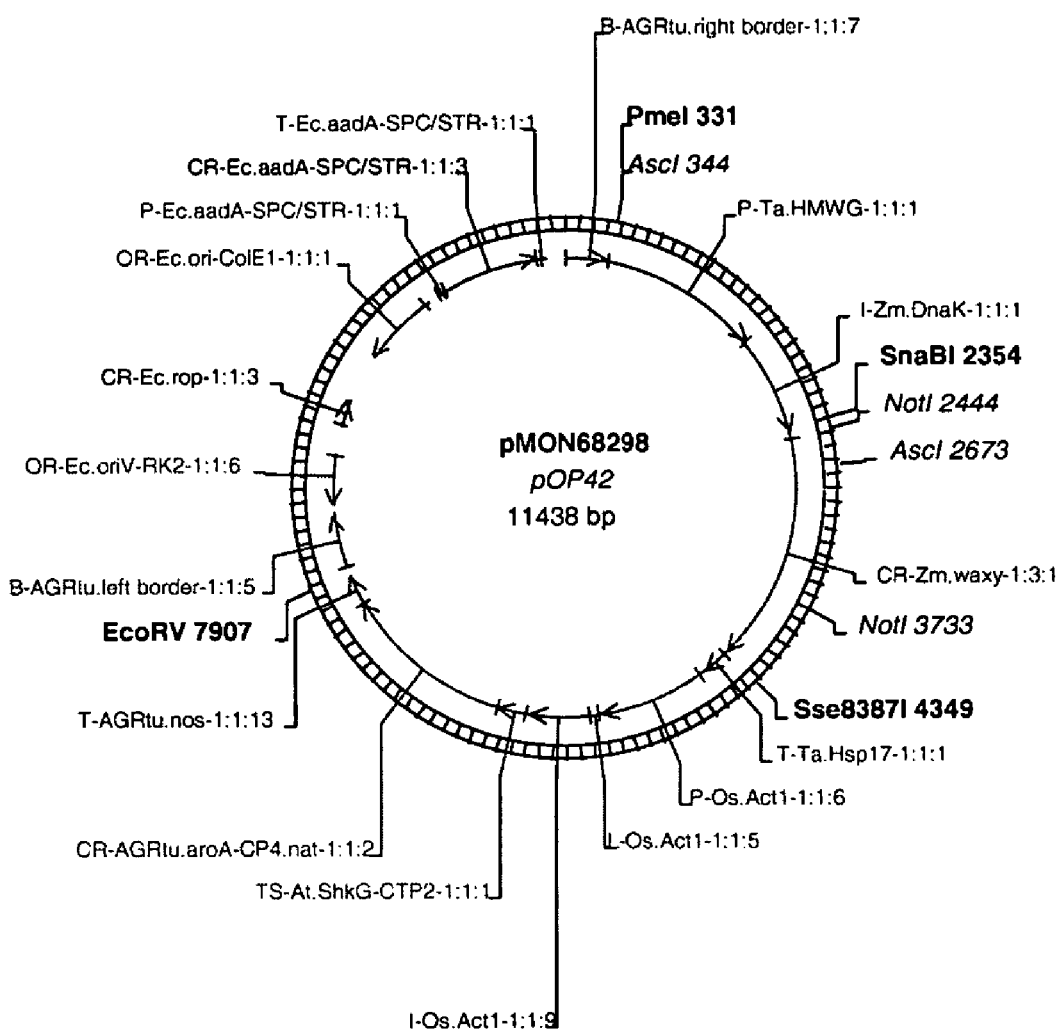
FIG. 8 depicts a plasmid map of pMON68298.

The amplification product, containing the promoter and intron fragment with the introduced restriction sites, was purified by agarose gel electrophoresis and cloned into pCR2.1 TOPO (Invitrogen) to generate a plasmid vector for *E. coli* transformation (pOP28). After transformation into an *E. coli* vector, plasmid DNA was isolated, digested with AscI and NotI, and the purified fragment was cloned into the binary vector pMON71274 to generate a vector (pOP29) containing a cassette with the wheat high molecular weight glutenin promoter fused to the corn HSP70 intron fused to the globulin 3' UTR. The HOI001 GBSS coding region was isolated by digestion of pMON81464 with NotI/Sse83871 and cloned into pOP29 to generate the binary vector pOP31 containing an expression cassette with the wheat high molecular weight glutenin promoter fused to the corn HSP70 intron fused to the HOI001 GBSS coding region fused to the globulin 3' UTR. The promoter/intron/HOI001 GBSS coding region fragment was then isolated from pOP31 by digestion with AscI/Sse83871 and then cloned into the plant binary vector pMON71290 containing a gene of interest cassette with the TR7 3' UTR to generate pOP35, containing an expression cassette with the wheat high molecular weight glutenin promoter fused to the corn HSP70 intron fused to the HOI001 GBSS coding region fused to the TR7 3' UTR. The promoter/intron/HOI001 GBSS coding region fragment was then isolated from pOP35 by digestion with AscI/Sse83871 and then cloned into the plant binary vector pMON67647, containing a gene of interest cassette with the wheat HSP17 3' UTR. The resulting plasmid contained an expression cassette with the wheat high molecular weight glutenin promoter fused to the corn HSP70 intron fused to the HOI001 GBSS coding region fused to the wheat HSP17 3' UTR. This plasmid, was named pMON68298, is shown in FIG. 8.

A third plant expression binary vector containing the promoter and 5' UTR of the HOI001 GBSS gene fused to the HOI001 GBSS coding region, fused to the corn globulin 3' UTR, was constructed. The HOI001 GBSS promoter and 5' UTR (which also contained the first predicted intron) was isolated by PCR amplification from pMON72506, using a 5' primer that contains the restriction site for PmeI:

```
5' Primer (primer number 20362):
5'-GATCGTTTAAACGTTCGTGTGGCAGATTCAT    [SEQ ID NO: 14]
C-3', 3' Primer (primer number 20363):
5'-GACGTGGCCAGAGCCGCCATGCCGATTAATC    [SEQ ID NO: 15]
CACTGCATAG-3'.
```

The amplification product, a fragment containing 1125 bp upstream of the predicted HOI001 GBSS translational start site and 20 bp of the predicted coding sequence from pMON72506 (corresponding to bp 17–1162 of SEQ ID NO: 1), was purified by agarose gel electrophoresis and cloned into pCR2.1 TOPO (Invitrogen) to generate pMON81466.

Figure 9:
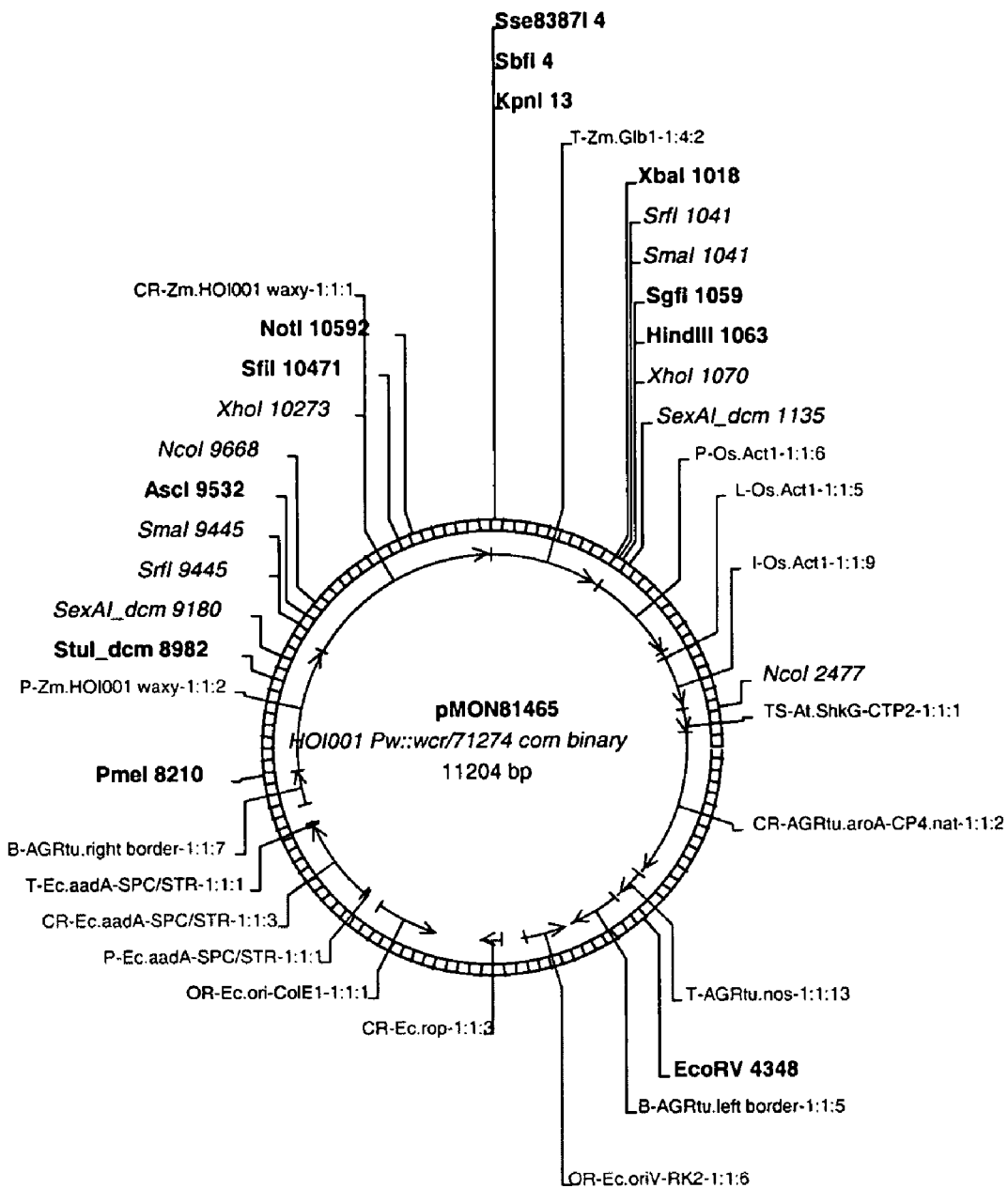
FIG. 9 depicts a plasmid map of pMON81465.

The HOI001 GBSS coding region was removed from pMON81463 and cloned into the vector pMON81466 to generate pMON81468, containing the HOI001 GBSS promoter/5' UTR fused to the HOI001 GBSS coding region, with 45 bp extraneous polylinker sequence between the promoter/UTR and coding region elements. This extraneous sequence was then deleted by digestion of pMON81468 with MluI to remove a 780 bp fragment spanning the extraneous sequence, then reannealing with the analogous 735 bp fragment (lacking the extraneous sequence), generating pMON81469. This 735 bp fragment was generated by digestion of pMON72506 with MluI and isolating the resulting fragment. This entire promoter/UTR/coding region sequence was then isolated from pMON81469 by digestion with PmeI and Sse83871, and cloned into the binary vector pMON71274 to generate the binary vector pMON81465. This vector contained an expression cassette with the promoter and 5' UTR of the HOI001 GBSS gene fused to the GBSS coding region fused to the corn globulin 3' UTR (FIG. 9).

These three plant transformation vectors are transformed into an elite corn inbred (LH244) (Corn States Hybrid Serv., LLC, Des Moines, Iowa). Briefly, ears containing immature embryos are harvested approximately 10 days after pollination and kept refrigerated at 4° C. until use (up to 5 days post-harvest). The preferred embryo size for this method of transformation is ~1.0–2.0 mm. This size is usually achieved 10 days after pollination inside the greenhouse with the growth conditions of an average temperature of 87° F., day length of 14 hours with supplemental lighting supplied by GE 1000 Watt High Pressure Sodium lamps.

Immature embryos are isolated from surface sterilized ears and directly dropped into the prepared *Agrobacterium* cell suspension in a 1.5-mL microcentrifuge tube. The isolation lasts continuously for 15 minutes. The tube is then set aside for 5 minutes, resulting in a total inoculation time for individual embryos from 5 to 20 minutes. After the *Agrobacterium* cell suspension is removed using a fine tipped sterile transfer pipette, the immature embryos are transferred onto a co-culture medium (Table 7). The embryos are then placed on the medium with the scutellum side facing up. The embryos are cultured in a dark incubator (23° C.) for approximately 24 hours.

The embryos are then transferred onto a modified MS medium (MSW50, Table 7) supplemented with 0.1 or 0.25 mM glyphosate and 250 mg/L carbenicillin to inhibit *Agrobacterium* in Petri dishes (100 mm×25 mm). The cultures are incubated in a dark culture room at 27° C. for 2–3 weeks. All the callus pieces are then transferred individually onto the first regeneration medium (MS/6BA, Table 7) supplemented with the same levels of glyphosate. The cultures are grown on this medium and in a culture room with 16 hours light/8 hours dark photoperiod and 27° C. for 5–7 days. They are then transferred onto the second 15 regeneration medium (MSOD, Table 7) in Petri dishes (100 mm×25 mm) for approximately 2 weeks. All the callus pieces with regenerating shoots and living tissue are transferred onto the same medium contained in phytatrays for shoots to grow further prior to being transferred to soil (approximately 2–4 weeks). The regeneration media (MS6BA and MSOD) are all supplemented with 250 mg/L carbenicillin and 0.1 or 0.25 mM glyphosate.

These developing plantlets are then transferred to soil, hardened off in a growth chamber at 27° C., 80% humidity, and low light intensity for approximately 1 week, and then transferred to a greenhouse and grown under standard greenhouse conditions. The resulting kernels are collected and analyzed as described in Example 4. The results indicate that the different promoters have different impacts on oil accumulation based upon the strength and timing of the expression of the HOI001 GBSS coding region.

TABLE 7

Composition of media used in corn transformation.

| Component | Co-culture Media | MSW50 | MS/6BA | MSOD |
|---|---|---|---|---|
| MS salts | 2.2 g/L | 4.4 g/L | 4.4 g/L | 4.4 g/L |
| Sucrose | 20 g/L | 30 g/L | 30 g/L | |
| Maltose | | | | 20 g/L |
| Glucose | 10 g/L | | | 10 g/L |
| l-Proline | 115 mg/L | 1.38 g/L | 1.36 g/L | |
| Casamino Acids | | 500 mg/L | 50 mg/L | |
| Glycine | 2 mg/L | 2 mg/L | | |
| l-Asparagine | | | | 150 mg/L |
| Myo-inositol | 100 mg/L | 100 mg/L | | 100 mg/L |
| Nicotinic acid | 0.5 mg/L | 0.5 mg/L | 1.3 mg/L | 1.3 mg/L |
| Pyridoxin HCl | 0.5 mg/L | 0.5 mg/L | 0.25 mg/L | 0.25 mg/L |
| Thiamine-HCl | 0.5 mg/L | 0.6 mg/L | 0.25 mg/L | 0.25 mg/L |
| Ca Pantothenate | | | 0.25 mg/L | 0.25 mg/L |
| 2,4-D | 3 mg/L | 0.5 mg/L | | |
| Picloram | | | | |
| Silver Nitrate | 1.7 mg/L | | | |
| BAP | | | 3.5 mg/L | |

Co-culture medium was solidified with 5.5 mg/l low EEO agarose. All other media were solidified with 7 g/l Phytagar for NPTII selection and with 3 g/l phytagel for glyphosate selection.

EXAMPLE 11

This example sets forth the use of the polymorphisms in the HOI001 GBSS gene as molecular markers to accelerate incorporation of HOI001 GBSS sequence polymorphisms into other corn germplasm with the result of increasing oil in the kernel.

The present invention provides a corn plant with increased kernel oil selected for by use of marker assisted breeding wherein a population of plants are selected for the presence of a polymorphism sequence unique to the HOI001 GBSS gene (SEQ ID NO: 1). Example 1, above, lists polymorphisms unique to the HOI001 GBSS sequence, that is not found in either the LH59 GBSS sequence or the published sequence (Shure et al., supra).

The selection of plants having the HOI001 GBSS gene for high oil comprises probing genomic DNA of the resulting plants, through the selection process, for the presence of the molecular marker for the HOI001 GBSS gene. The molecular marker is a DNA molecule representing a unique polymorphism in the HOI001 GBSS gene that functions as a probe or primer to a target HOI001 GBSS in a plant genome. The selected polymorphism may or may not be from a coding region of the gene. The plants containing the HOI001 GBSS gene are continued in the breeding and selection process.

What is claimed is:

1. A substantially purified nucleic acid molecule selected from the group consisting of:
   a) a nucleic acid molecule comprising SEQ ID NO: 1 or the complement thereof;
   b) a nucleic acid molecule comprising SEQ ID NO; 11 or the complement thereof; and
   c) a nucleic acid molecule which encodes a polypeptide having at least 95% amino acid identity with SEQ ID NO: 3.

2. An expression cassette comprising a nucleic acid molecule of claim 1, wherein said nucleic acid molecule is operably linked to a promoter, which is functional in a plant cell.

3. A plant cell comprising the expression cassette of claim 2.

4. A plant comprising the plant cell of claim 3.

5. A plant according to claim 4, wherein the plant is a monocot.

6. A plant according to claim 5, wherein the monocot plant is corn.

7. Seeds obtained from a corn plant, wherein the seeds comprise the nucleic acid molecule of claim 1.

8. A plant having stably incorporated into its genome a nucleic acid molecule selected from the group consisting of:
   a) a nucleic acid molecule comprising SEQ ID NO: 1 or the complement thereof;
   b) a nucleic acid molecule comprising SEQ ID NO: 11 or the complement thereof; and
   c) a nucleic acid molecule which encodes a polypeptide having at least 95% amino acid identity with SEQ ID NO: 3.

9. A transgenic plant according to claim 8, wherein the plant is a monocot.

10. The monocot plant of claim 9, wherein the plant is corn.

11. Transgenic seeds obtained from the plant of claim 10, wherein the seeds comprise said nucleic acid molecule.

12. A method of producing a plant having increased levels of oil production, wherein the method comprises:
   (a) transforming a plant with an expression cassette comprising a nucleic acid molecule selected from the group consisting of:
      i) a nucleic acid molecule comprising SEQ ID NO: 1 or the complement thereof;
      ii) a nucleic acid molecule comprising SEQ ID NO: 11 or the complement thereof; and
      iii) a nucleic acid molecule which encodes a polypeptide having at least 95% amino acid identity with SEQ ID NO: 3; wherein said expression cassette further comprises a promoter region functional in a plant cell, operably linked to said nucleic acid molecule; and
   (b) growing the transformed plant.

13. The method claim 12, wherein the plant is a monocot.

14. The method of claim 13, wherein the monocot plant is corn.

15. The method of claim 14, wherein the promoter region is an endosperm-preferred promoter region.

16. The method of claim 15, wherein the promoter region is the Z27 promoter region.

* * * * *

UNITED STATES PATENT AND TRADEMARK OFFICE
CERTIFICATE OF CORRECTION

PATENT NO. : 7,179,956 B2
APPLICATION NO. : 10/877645
DATED : February 20, 2007
INVENTOR(S) : Ravanello et al.

It is certified that error appears in the above-identified patent and that said Letters Patent is hereby corrected as shown below:

In claim 1, column 61, line 6, delete "NO;" and insert --NO:-- therefor.

Signed and Sealed this

Twenty-ninth Day of May, 2007

JON W. DUDAS
*Director of the United States Patent and Trademark Office*